(12) United States Patent
DeSimone et al.

(10) Patent No.: US 8,263,129 B2
(45) Date of Patent: Sep. 11, 2012

(54) METHODS FOR FABRICATING ISOLATED MICRO-AND NANO-STRUCTURES USING SOFT OR IMPRINT LITHOGRAPHY

(75) Inventors: Joseph M. DeSimone, Chapel Hill, NC (US); Jason P. Rolland, Durham, NC (US); Benjamin W. Maynor, Durham, NC (US); Larken E. Euliss, Chapel Hill, NC (US); Ginger Denison Rothrock, Durham, NC (US); Ansley E Dennis, Augusta, GA (US); Edward T. Samulski, Chapel Hill, NC (US); R. Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1486 days.

(21) Appl. No.: 10/583,570

(22) PCT Filed: Dec. 20, 2004

(86) PCT No.: PCT/US2004/042706
§ 371 (c)(1),
(2), (4) Date: Mar. 5, 2007

(87) PCT Pub. No.: WO2005/101466
PCT Pub. Date: Oct. 27, 2005

(65) Prior Publication Data
US 2009/0028910 A1    Jan. 29, 2009

Related U.S. Application Data

(60) Provisional application No. 60/531,531, filed on Dec. 19, 2003, provisional application No. 60/583,170, filed on Jun. 25, 2004, provisional application No. 60/604,970, filed on Aug. 27, 2004.

(51) Int. Cl.
*A61K 9/14* (2006.01)
*B28B 11/08* (2006.01)

(52) U.S. Cl. .................. 424/489; 264/293; 977/773

(58) Field of Classification Search .................. None
See application file for complete search history.

(56) References Cited

U.S. PATENT DOCUMENTS

| | | |
|---|---|---|
| 2,128,179 A | 7/1937 | Du Grenier |
| 4,065,252 A | 12/1977 | Hemsath et al. |
| 4,191,321 A | 3/1980 | Samsing |
| 4,332,887 A | 6/1982 | Gerber |
| 4,352,874 A | 10/1982 | Land et al. |
| 4,353,977 A | 10/1982 | Gerber et al. |
| 4,356,257 A | 10/1982 | Gerber |
| 4,359,525 A | 11/1982 | Gerber |
| 4,359,526 A | 11/1982 | Walworth |
| 4,362,806 A | 12/1982 | Whitmore |
| 4,366,235 A | 12/1982 | Land |
| 4,512,848 A | 4/1985 | Deckman et al. |
| 4,614,667 A | 9/1986 | Larson et al. |
| 4,663,274 A | 5/1987 | Slafer et al. |
| 4,681,925 A | 7/1987 | Strepparola et al. |
| 4,697,514 A | 10/1987 | George et al. |
| 4,818,801 A | 4/1989 | Rice et al. |
| 4,830,910 A | 5/1989 | Larson |
| 5,041,359 A | 8/1991 | Kooi |
| 5,175,030 A | 12/1992 | Lu et al. |
| 5,259,926 A | 11/1993 | Kuwabara et al. |
| 5,279,689 A | 1/1994 | Shvartsman |
| 5,294,476 A | 3/1994 | Calhoun |
| 5,368,789 A | 11/1994 | Kamitakahara et al. |
| 5,425,848 A | 6/1995 | Haisma et al. |
| 5,512,131 A | 4/1996 | Kumar et al. |
| 5,630,902 A | 5/1997 | Galarneau et al. |
| 5,772,905 A | 6/1998 | Chou |
| 5,817,242 A | 10/1998 | Biebuyck et al. |
| 5,834,025 A | 11/1998 | de Garavilla et al. |
| 5,869,103 A | 2/1999 | Yeh et al. |
| 5,994,133 A | 11/1999 | Meijs et al. |
| 6,000,603 A | 12/1999 | Koskenmaki et al. |
| 6,027,595 A | 2/2000 | Suleski |
| 6,027,630 A | 2/2000 | Cohen |
| 6,228,318 B1 | 5/2001 | Nakamae et al. |
| 6,245,849 B1 | 6/2001 | Morales et al. |
| 6,247,986 B1 | 6/2001 | Chiu et al. |
| 6,284,072 B1 | 9/2001 | Ryan et al. |
| 6,284,345 B1 | 9/2001 | Ruoff |
| 6,294,450 B1 | 9/2001 | Chen et al. |
| 6,300,042 B1 | 10/2001 | Mancini et al. |
| 6,306,563 B1 | 10/2001 | Xu et al. |
| 6,334,960 B1 | 1/2002 | Willson et al. |
| 6,355,198 B1 | 3/2002 | Kim et al. |
| 6,375,870 B1 | 4/2002 | Visovsky et al. |
| 6,402,876 B1 | 6/2002 | McArdle et al. |
| 6,422,528 B1 | 7/2002 | Domeier et al. |
| 6,507,989 B1 | 1/2003 | Bowden et al. |

(Continued)

FOREIGN PATENT DOCUMENTS

EP    0 393 263 B1    6/1997

(Continued)

OTHER PUBLICATIONS

Rothschild, M.; Bloomstein, T.M.; Fedynyshyn, T.H.; Liberman, V.; Mowers, W.; Sinta, R.; Switkes, M.; Grenville, A.; Orvek, K. Fluorine-an enabler in advanced photolithography. Journal of Fluorine Chemistry, vol. 122, 2003, pp. 3-10.*

(Continued)

*Primary Examiner* — Robert A Wax
*Assistant Examiner* — Jessica Worsham
(74) *Attorney, Agent, or Firm* — Alston & Bird LLP

(57) ABSTRACT

The presently disclosed subject matter describes the use of fluorinated elastomer-based materials, in particular perfluoropolyether (PFPE)-based materials, in high-resolution soft or imprint lithographic applications, such as micro- and nanoscale replica molding, and the first nano-contact molding of organic materials to generate high fidelity features using an elastomeric mold. Accordingly, the presently disclosed subject matter describes a method for producing freestanding, isolated nanostructures of any shape using soft or imprint lithography techniques.

32 Claims, 31 Drawing Sheets

U.S. PATENT DOCUMENTS

| | | | |
|---|---|---|---|
| 6,517,995 B1 | 2/2003 | Jacobson et al. | |
| 6,518,189 B1 | 2/2003 | Chou | |
| 6,555,221 B1 | 4/2003 | Komiyama et al. | |
| 6,589,629 B1 | 7/2003 | Bao et al. | |
| 6,607,683 B1 | 8/2003 | Harrington | |
| 6,645,432 B1* | 11/2003 | Anderson et al. | 422/502 |
| 6,649,715 B1 | 11/2003 | Smith et al. | |
| 6,653,030 B2 | 11/2003 | Mei et al. | |
| 6,656,308 B2 | 12/2003 | Hougham et al. | |
| 6,656,398 B2 | 12/2003 | Birch et al. | |
| 6,660,192 B1 | 12/2003 | Kim et al. | |
| 6,663,820 B2 | 12/2003 | Arias et al. | |
| 6,673,519 B2 | 1/2004 | Bennett et al. | |
| 6,686,184 B1 | 2/2004 | Anderson et al. | |
| 6,696,220 B2 | 2/2004 | Bailey et al. | |
| 6,699,347 B2 | 3/2004 | Lehrter et al. | |
| 6,719,868 B1 | 4/2004 | Schueller et al. | |
| 6,752,942 B2 | 6/2004 | Kim et al. | |
| 6,753,131 B1 | 6/2004 | Rogers et al. | |
| 6,755,984 B2 | 6/2004 | Lee et al. | |
| 6,759,182 B2 | 7/2004 | Ikeda et al. | |
| 6,770,721 B1 | 8/2004 | Kim | |
| 6,783,717 B2 | 8/2004 | Hougham et al. | |
| 6,808,646 B1 | 10/2004 | Jeans | |
| 6,809,356 B2 | 10/2004 | Chou | |
| 6,818,139 B1 | 11/2004 | Lee et al. | 216/41 |
| 6,828,244 B2 | 12/2004 | Chou | |
| 6,829,050 B2 | 12/2004 | Ikeda et al. | |
| 6,849,558 B2 | 2/2005 | Schaper | |
| 6,855,202 B2 | 2/2005 | Alivisatos et al. | |
| 6,860,956 B2 | 3/2005 | Bao et al. | |
| 6,869,557 B1 | 3/2005 | Wago et al. | |
| 6,872,645 B2 | 3/2005 | Duan et al. | |
| 6,900,881 B2 | 5/2005 | Sreenivasan et al. | |
| 6,923,930 B2 | 8/2005 | Ling et al. | |
| 6,932,934 B2 | 8/2005 | Choi et al. | |
| 6,936,181 B2 | 8/2005 | Bulthaup et al. | |
| 6,936,194 B2 | 8/2005 | Watts | |
| 6,964,793 B2 | 11/2005 | Willson et al. | |
| 6,976,424 B2 | 12/2005 | Bruno et al. | |
| 6,993,655 B1 | 1/2006 | Hecht et al. | |
| 7,052,618 B2 | 5/2006 | Moll et al. | |
| 7,056,409 B2 | 6/2006 | Dubrow | |
| 7,056,834 B2 | 6/2006 | Mei et al. | |
| 7,070,406 B2 | 7/2006 | Jeans | |
| 7,081,269 B2 | 7/2006 | Yang et al. | |
| 7,117,790 B2 | 10/2006 | Kendale et al. | |
| 7,122,482 B2 | 10/2006 | Xu et al. | 438/738 |
| 7,141,275 B2 | 11/2006 | Chen | |
| 7,148,142 B1 | 12/2006 | Dakshina-Murthy et al. | |
| 7,168,939 B2 | 1/2007 | Bietsch et al. | |
| 7,195,733 B2 | 3/2007 | Rogers et al. | |
| 7,235,464 B2 | 6/2007 | Bona et al. | |
| 7,254,278 B2 | 8/2007 | Jung | |
| 7,288,320 B2 | 10/2007 | Steenblik et al. | |
| 7,294,294 B1 | 11/2007 | Wago et al. | |
| 2001/0037455 A1 | 11/2001 | Lawandy et al. | |
| 2002/0172895 A1 | 11/2002 | Breen et al. | |
| 2003/0006527 A1 | 1/2003 | Rabolt et al. | |
| 2003/0062334 A1 | 4/2003 | Lee et al. | |
| 2003/0071016 A1 | 4/2003 | Shih et al. | |
| 2003/0205552 A1 | 11/2003 | Hansford et al. | |
| 2004/0028804 A1 | 2/2004 | Anderson et al. | |
| 2004/0029978 A1 | 2/2004 | Chane-Ching | |
| 2004/0046271 A1 | 3/2004 | Watts | |
| 2004/0053009 A1 | 3/2004 | Ozin et al. | |
| 2004/0065252 A1 | 4/2004 | Sreenivasan et al. | |
| 2004/0067360 A1 | 4/2004 | Steenblik et al. | |
| 2004/0097371 A1 | 5/2004 | Jangbarwala | |
| 2004/0110856 A1 | 6/2004 | Young et al. | |
| 2004/0115239 A1* | 6/2004 | Shastri et al. | 424/423 |
| 2004/0115270 A1 | 6/2004 | Jani et al. | |
| 2004/0137734 A1 | 7/2004 | Chou et al. | |
| 2004/0169791 A1 | 9/2004 | Nilsen et al. | |
| 2004/0182820 A1 | 9/2004 | Motowaki et al. | |
| 2004/0202865 A1 | 10/2004 | Homola et al. | |
| 2004/0217085 A1 | 11/2004 | Jeans | |
| 2004/0219246 A1 | 11/2004 | Jeans | |
| 2005/0038180 A1 | 2/2005 | Jeans | |
| 2005/0061773 A1 | 3/2005 | Choi et al. | |
| 2005/0064209 A1 | 3/2005 | Haines et al. | |
| 2005/0064452 A1 | 3/2005 | Schmid et al. | |
| 2005/0104756 A1 | 5/2005 | Tazartes et al. | |
| 2005/0120902 A1 | 6/2005 | Adams et al. | |
| 2005/0133943 A1 | 6/2005 | Akutsu et al. | |
| 2005/0176182 A1 | 8/2005 | Me et al. | |
| 2005/0196702 A1 | 9/2005 | Bryant et al. | |
| 2005/0202350 A1 | 9/2005 | Colburn et al. | |
| 2005/0214661 A1 | 9/2005 | Stasiak et al. | |
| 2006/0021533 A1 | 2/2006 | Jeans | |
| 2006/0068128 A1 | 3/2006 | Greener et al. | |
| 2006/0096477 A1 | 5/2006 | Bietsch et al. | |
| 2006/0096949 A1 | 5/2006 | Watts et al. | |
| 2006/0188598 A1 | 8/2006 | Jeans | |
| 2006/0214326 A1 | 9/2006 | Kim et al. | |
| 2007/0269747 A1 | 11/2007 | Bahadur et al. | |
| 2008/0038398 A1 | 2/2008 | Wago et al. | |

FOREIGN PATENT DOCUMENTS

| | | |
|---|---|---|
| EP | 1 473 594 A2 | 11/2004 |
| EP | 1 517 181 A1 | 3/2005 |
| EP | 1 533 657 A1 | 5/2005 |
| EP | 1 551 066 A1 | 7/2005 |
| KR | 2003-0075971 | 9/2003 |
| WO | WO 96/17266 | 6/1996 |
| WO | WO 96/20698 | 7/1996 |
| WO | WO 96/31548 | 10/1996 |
| WO | WO 02/14078 A2 | 2/2002 |
| WO | WO 02/24604 A1 | 3/2002 |
| WO | WO 02/29397 A2 | 4/2002 |
| WO | WO 03/005124 A1 | 1/2003 |
| WO | WO 03/031096 A2 | 4/2003 |
| WO | WO 03/098188 A2 | 11/2003 |
| WO | WO 2004/033189 A1 | 4/2004 |
| WO | WO 2004/096896 A2 | 11/2004 |
| WO | WO 2004/097371 A2 | 11/2004 |
| WO | WO 2005/047575 A1 | 5/2005 |
| WO | WO 2005/059952 A2 | 6/2005 |
| WO | WO 2005/089106 A2 | 9/2005 |
| WO | WO 2005/104756 A2 | 11/2005 |
| WO | WO 2006/012915 A1 | 2/2006 |
| WO | WO 2006/041645 A2 | 4/2006 |
| WO | WO 2006/071470 A2 | 7/2006 |

OTHER PUBLICATIONS

Bailey, T., et al. "Step and Flash Imprint Lithography: Template Surface Treatment and Defect Analysis," *J. Vac. Sci. Technol. B*, 2000, pp. 3572-3577, vol. 18(6).

Hirai, Y., et al., "Mold Surface Treatment for Imprint Lithography," *Journal of Photopolymer Science and Technology*, 2001, pp. 457-462, vol. 14(3).

Barton, J.E. et. al., "Mass-Limited Growth in Zeptoliter Beakers: A General Approach for the Synthesis of Nanocrystals," *Nano Lett.*, Jul. 2004, pp. 1555-1528, vol. 4(8).

Becker, H. and C. Gartner, "Polymer Microfabrication Methods for Microfluidic Analytical Applications," *Electrophoresis*, 2000, pp. 12-26, vol. 21.

Choi, S-J., et al., "An Ultraviolet-Curable Mold for Sub-100-NM Lithography," *J. Am. Chem. Soc.*, 2004, pp. 7744-7745, vol. 126.

Choi, W.M. and O.O. Park, "A Soft-Imprint Technique for Direct Fabrication of Submicron Scale Patterns Using a Surface-Modified PDMS Mold," *Microelect. Eng.*, 2003, pp. 131-136, vol. 70, Elsevier.

Chou, S.Y. and P.R. Krauss, "Imprint Lithography with Sub-10 nm Feature Size and High Throughput," *Microelect. Eng.*, 1997, pp. 237-240, vol. 35.

Chou, S.Y., et al., "Imprint of Sub-25 nm Vias and Trenches in Polymers," *Appl. Phys. Lett.*, 1995, pp. 3114-3116, vol. 67(21).

Colburn, M., "Capillary Fill Time & Meniscus Shape: An Asymmetric, Nonequal Contact Angle, Coplanar Cavity Study," *ChE 385 Project Report*, Available Online at Willson.cm.utexas.edu- ...-Surface_Phenomena-Spring1999 Asymetric_Noon_equal_contact_angle_capillary_study, Dec. 3, 1998.

Cooper, K.P., "Layered Manufacturing: Challenges and Opportunities," *Mat. Res. Soc. Symp. Proc*, 2003, pp. LL1.4.1- LL1.4.12.

El-Sayed, M.A., "Some Interesting Properties of Metals Confined in Time and Nanometer Space of Different Shapes," *Accts. Chem. Res.*, 2001, pp. 257-264, vol. 34(4).

Gadegaard, N., et al., "Biomimetic Polymer Nanostructures by Injection Molding," *Macromol. Mater. Eng.*, 2003, pp. 76-83, vol. 288(1).

Gates, B., et al., "New Approaches to Nanofabrication: Molding, Printing and Other Techniques," *Chem. Rev.*, 2005, pp. 1171-1196, vol. 105(4).

Haatainen, T and J. Ahopelto, "Step & Stamp Imprint Lithography: A Versatile Method for Nanoimprinting," presented at the NNT Conference, Dec. 11-13, 2002 at San-Francisco, CA.

Haatainen, T., and J. Ahopelto, "Pattern Transfer Using Step & Stamp Imprint Lithography," *Physica. Scripta.*, 2003, pp. 357-360, vol. 67.

Haatainen, T., et. al., "Step & Stamp Imprint Lithography Using a Commercial Flip Chip Bonder," *Proceeding of SPIE's 25th Annual International Symposium of Microlithography, Emerging Lithographic Technologies IV* at Santa Clara, CA, 2000, pp. 1-10.

Haisma, J., et al., "Mold-Assisted Nanolithography: A Process for Reliable Pattern Replication," *J. Vac. Sci. Technol.*, 1996, pp. 4124-4128, vol. B14(6).

Hua, F., et al., "Polymer Imprint Lithography with Molecular-Scale Resolution," *Nano Letters*, 2004, pp. 2467-2471, vol. 4(12).

Hulteen, J.C. and C.R. Martin, "A General Template-Based Method for the Preparation of Nanomaterials," *J. Mater. Chem.*, 1997, pp. 1075-1087, vol. 7(7).

Jackman, R., et al., "Fabricating Large Arrays of Microwells with Arbitrary Dimensions and Filling Them Using Discontinuous Dewetting," *Analytical Chemistry*, 1998, pp. 2280-2287, vol. 70(11).

Jiang, P., et. al., "A Lost-Wax Approach to Monodisperse Colloids and Their Crystals," *Science*, 2001, pp. 453-457, vol. 291.

Katz, E. and I. Willner, "Integrated Nanoparticle-Biomolecule Hybrid Systems: Synthesis, Properties, and Applications," *Angew. Chem. Int. Ed.*, 2004, pp. 6042-6108, vol. 43.

Khang, D. and H.L. Hong, "Pressure-Assisted Capillary Force Lithography," *Adv. Mater.*, 2004, pp. 176-179, vol. 16(2).

Krauss, P., et al., Fabrication of Nanodevices Using Sub-25 nm Imprint Lithography, *Presented at NanoStructure Laboratory, Department of Electrical Engineering, University of Minnesota, Minneapolis, MN*, pp. 194-195.

Marzolin, C., et al., "Fabrication of Glass Microstructures by Micro-Molding of Sol-Gel Precursors," *Adv.Mater.*, 1998, pp. 571-574, vol. 10(8).

Meiring, J. E., et al., "Hydrogel Biosensor Array Platform Indexed by Shape," *Chem. Mater.*, 2004, pp. 5574-5580, vol. 16.

Moran, P. M. and C. Robert, "Microstamping of Freestanding Bipolymer Features," *American Institute of Physics*, 2001, pp. 3741-3743, vol. 78(23).

Nicewarner-Peña, S., et al., "Submicrometer Metallic Barcodes," *Science*, 2001, pp. 137-141., vol. 294.

Pileni, M., "The Role of Soft Colloidal Templates in Controlling the Size and Shape of Inorganic Nanocrystals," *Nature Materials*, 2003, pp. 145-150, vol. 2, Nature Publishing Group.

Rejman, J., et al., "Size-Dependent Internalization of Particles Via the Pathways of Clathrin-and Caveolae-Mediated Endocytosis," *Biochem. J.*, 2004, pp. 159-169., vol. 377.

Rolland, J.P., et al., "High-Resolution Soft Lithography: Enabling Materials for Nanotechnologies," *Angew. Chem. Int. Ed.*, 2004, pp. 5796-5799, vol. 43.

Rolland, J. P., et al., "Solvent-Resistant Photocurable "Liquid Teflon" for Microfluidic Device Fabrication," *J. Am. Chem. Soc.*, 2004, pp. 2322-2323, vol. 126.

Sosa, I. O., et al., "Optical Properties of Metal Nanoparticles with Arbitrary Shapes," *J Phys. Chem.*, 2003, pp. 6269-6275, vol. 107.

Suh, K.Y., et al., "Capillary Force Lithography," *Adv. Mater.*, 2001, pp. 1386-1389, vol. 13(18).

Suh, K.Y., et al., "Observation of High-Aspect-Ratio Nanostructures Using Capillary Lithography," *Adv. Mater.*, 2005, pp. 560-564, vol. 17(5).

Suh, K.Y., and H.H. Lee, "Capillary Force Lithography: Large-Area Patterning, Self-Organization, and Anisotropic Dewetting," *Adv. Funct. Mater.*, 2002, pp. 405-413, vol. 12(6+7).

Sun, Y. and Y. Xia, "Shape-Controlled Synthesis of Gold and Silver Nanoparticles," *Science*, 2002, pp. 2176-2179, vol. 298.

Tan, H., et al., "Roller Nanoimprint Lithography," *J. Vac. Sci. Technol.*, 1998, pp. 3926-3928, vol. B16(6).

Tien, J., et al., "Crystallization of Millimeter-Scale Objects with Use of Capillary Forces," *J Am. Chem. Soc.*, 1998, pp. 12670-12671, vol. 120.

Xia, Y., et al., "Complex Optical Surfaces by Replica Molding Against Elastomeric Masters," *Sci New Series*, 1996, pp. 347-349, vol. 274(5273).

Xia, Y. and G.M. Whitesides, "Soft Lithography," *Agnew. Chem. Ed.*, 1998, pp. 550-575, vol. 37.

Yin, Y. and Y. Xia, "Self-Assembly of Monodispersed Spherical Colloids into Complex Aggregates with Well-Defined Sizes, Shapes, and Structures," *Adv. Mater.*, 2001, pp. 267-271, vol. 13(4).

Zhao, X-M., et al., "Soft Lithographic Methods for Nano-Fabrication," *J. Mater. Chem.*, 1997, pp. 1069-1074, vol. 7(7).

Notification of Transmittal of International Preliminary Report on Patentability corresponding to PCT Application No. PCT/US04/42706 dated Aug. 17, 2007.

Manna, L., et al., "Synthesis of Soluble and Processable Rod-, Arrow-, Teardrop-, and Tetrapod-Shaped CdSe Nanocrystals," *J. Am. Chem. Soc.*, 2000, vol. 122, pp. 12700-12706.

Yin, Y., et al., "A Soft Lithography Approach to the Fabrication of Nanostructures of Single Crystalline Silicon with Well-Defined Dimensions and Shapes," *Adv. Mater.*, 2000, vol. 12(19), pp. 1426-1430.

\* cited by examiner

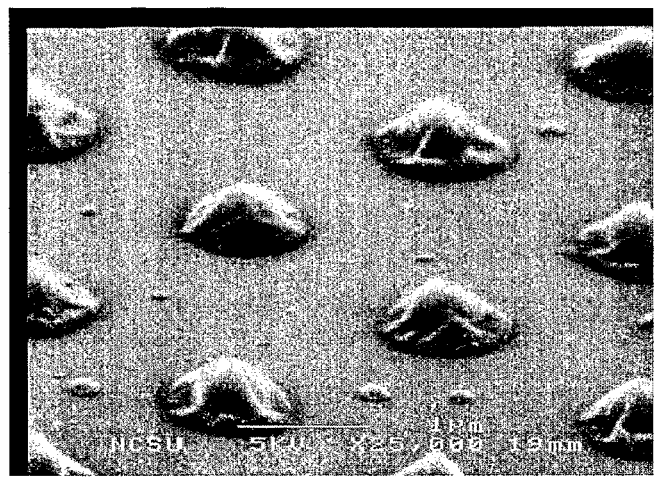
*Fig. 27*
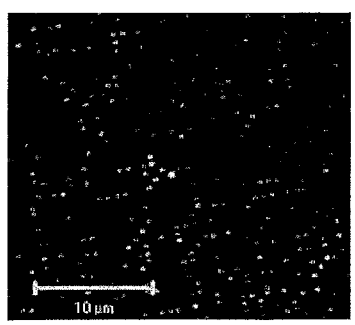 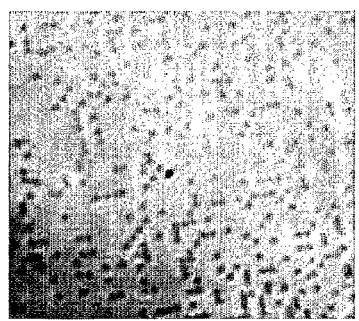 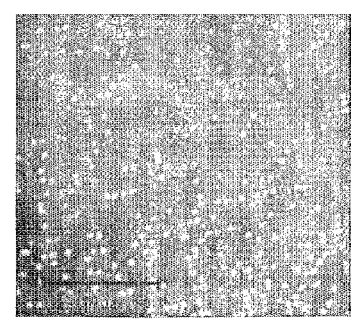
*Fig. 28A*     *Fig. 28B*     *Fig. 28C*

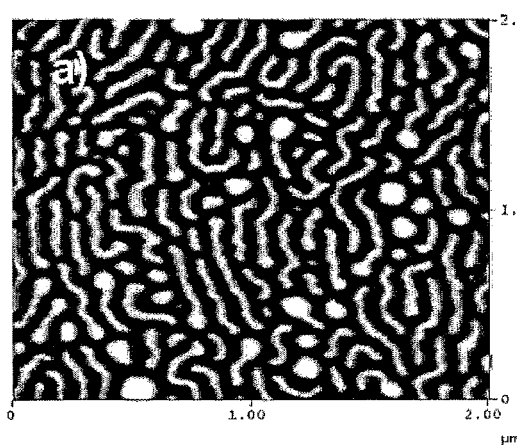 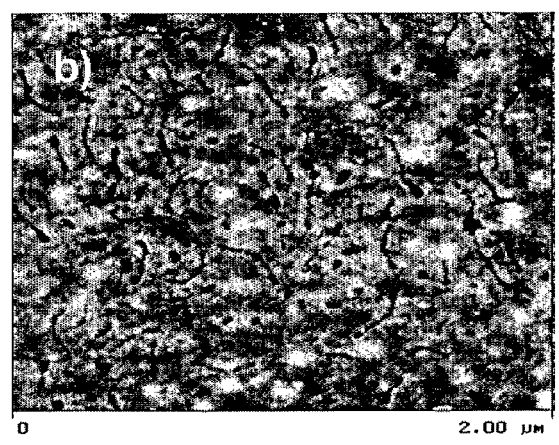
Fig. 35A                    Fig. 35B

METHODS FOR FABRICATING ISOLATED MICRO- AND NANO-STRUCTURES USING SOFT OR IMPRINT LITHOGRAPHY

CROSS REFERENCE TO RELATED APPLICATIONS

This application is based on and claims priority to U.S. Provisional Patent Application Ser. No. 60/531,531, filed Dec. 19, 2003, U.S. Provisional Patent Application Ser. No. 60/583,170, filed Jun. 25, 2004, U.S. Provisional Patent Application Ser. No. 60/604,970, filed Aug. 27, 2004, each of which is incorporated herein by reference in its entirety.

GOVERNMENT INTEREST

This invention was made with U.S. Government support from the Office of Naval Research Grant No. N00014210185 and the Science and Technology Center program of the National Science Foundation under Agreement No. CHE-9876674. The U.S. Government has certain rights in the invention.

TECHNICAL FIELD

Methods for preparing micro- and/or nanoscale particles using soft or imprint lithography. A method for delivering a therapeutic agent to a target. Methods for forming a micro- or nano-scale pattern on a substrate using soft or imprint lithography.

ABBREVIATIONS

° C. degrees Celsius
cm=centimeter
DBTDA=dibutyltin diacetate
DMA=dimethylacrylate
DMPA=2,2-dimethoxy-2-phenylacetophenone
EIM=2-isocyanatoethyl methacrylate
FEP=fluorinated ethylene propylene
Freon 113=1,1,2-trichlorotrifluoroethane
g=grams
h=hours
Hz=hertz
IL=imprint lithography
kg=kilograms
kHz=kilohertz
kPa=kilopascal
MCP=microcontact printing
MEMS=micro-electro-mechanical system
MHz=megahertz
MIMIC=micro-molding in capillaries
mL=milliliters
mm=millimeters
mmol=millimoles
mN=milli-Newton
m.p.=melting point
mW=milliwatts
NCM=nano-contact molding
NIL=nanoimprint lithography
nm=nanometers
PDMS=polydimethylsiloxane
PEG=poly(ethylene glycol)
PFPE=perfluoropolyether
PLA=poly(lactic acid)
PP=polypropylene
Ppy=poly(pyrrole)
psi=pounds per square inch
PVDF=poly(vinylidene fluoride)
PTFE=polytetrafluoroethylene
SAMIM=solvent-assisted micro-molding
SEM=scanning electron microscopy
S-FIL="step and flash" imprint lithography
Si=silicon
TMPTA=trimethylopropane triacrylate
µm=micrometers
UV=ultraviolet
W=watts
ZDOL=poly(tetrafluoroethylene oxide-co-difluoromethylene oxide)$\alpha,\omega$ diol

BACKGROUND

The availability of viable nanofabrication processes is a key factor to realizing the potential of nanotechnologies. In particular, the availability of viable nanofabrication processes is important to the fields of photonics, electronics, and proteomics. Traditional imprint lithographic (IL) techniques are an alternative to photolithography for manufacturing integrated circuits, micro- and nano-fluidic devices, and other devices with micrometer and/or nanometer sized features. There is a need in the art, however, for new materials to advance IL techniques. See Xia, Y., et al., *Angew. Chem. Int. Ed.*, 1998, 37, 550-575; Xia, Y., et al., *Chem. Rev.*, 1999, 99, 1823-1848; Resnick, D. J., et al., *Semiconductor International*, 2002, June, 71-78; Choi, K. M., et al., *J. Am. Chem. Soc.*, 2003, 125, 4060-4061; McClelland, G. M., et al., *Appl. Phys. Lett.*, 2002, 81, 1483; Chou, S. Y., et al., *J. Vac. Sci. Technol. B*, 1996, 14, 4129; Otto, M., et al., *Microelectron. Eng.*, 2001, 57, 361; and Bailey, T., et al., *J. Vac. Sci. Technol., B*, 2000, 18, 3571.

Imprint lithography comprises at least two areas: (1) soft lithographic techniques, see Xia, Y., et al., *Angew. Chem. Int. Ed.*, 1998, 37, 550-575, such as solvent-assisted micro-molding (SAMIM); micro-molding in capillaries (MIMIC); and microcontact printing (MCP); and (2) rigid imprint lithographic techniques, such as nano-contact molding (NCM), see McClelland, G. M., et al., *Appl. Phys. Lett.*, 2002, 81, 1483; Otto, M., et al., *Microelectron. Eng.*, 2001, 57, 361; "step and flash" imprint lithographic (S-FIL), see Bailey, T., et al., *J. Vac. Sci. Technol.*, B, 2000, 18, 3571; and nanoimprint lithography (NIL), see Chou, S. Y., et al., *J. Vac. Sci. Technol. B*, 1996, 14, 4129.

Polydimethylsiloxane (PDMS) based networks have been the material of choice for much of the work in soft lithography. See Quake, S. R., et al., *Science*, 2000, 290, 1536; Y. N. Xia and G. M. Whitesides, *Angew. Chem. Int. Ed. Engl.* 1998, 37, 551; and Y. N. Xia, et al., *Chem. Rev.* 1999, 99, 1823.

The use of soft, elastomeric materials, such as PDMS, offers several advantages for lithographic techniques. For example, PDMS is highly transparent to ultraviolet (UV) radiation and has a very low Young's modulus (approximately 750 kPa), which gives it the flexibility required for conformal contact, even over surface irregularities, without the potential for cracking. In contrast, cracking can occur with molds made from brittle, high-modulus materials, such as etched silicon and glass. See Bietsch, A., et al., *J. Appl. Phys.*, 2000, 88, 4310-4318. Further, flexibility in a mold facilitates the easy release of the mold from masters and replicates without cracking and allows the mold to endure multiple imprinting steps without damaging fragile features. Additionally, many soft, elastomeric materials are gas permeable, a property that can be used to advantage in soft lithography applications.

Although PDMS offers some advantages in soft lithography applications, several properties inherent to PDMS severely limit its capabilities in soft lithography. First, PDMS-based elastomers swell when exposed to most organic soluble compounds. See Lee, J. N., et al., *Anal. Chem.*, 2003, 75, 6544-6554. Although this property is beneficial in microcontact printing (MCP) applications because it allows the mold to adsorb organic inks, see Xia, Y., et al., *Angew. Chem. Int. Ed.*, 1998, 37, 550-575, swelling resistance is critically important in the majority of other soft lithographic techniques, especially for SAMIM and MIMIC, and for IL techniques in which a mold is brought into contact with a small amount of curable organic monomer or resin. Otherwise, the fidelity of the features on the mold is lost and an unsolvable adhesion problem ensues due to infiltration of the curable liquid into the mold. Such problems commonly occur with PDMS-based molds because most organic liquids swell PDMS. Organic materials, however, are the materials most desirable to mold. Additionally, acidic or basic aqueous solutions react with PDMS, causing breakage of the polymer chain.

Secondly, the surface energy of PDMS (approximately 25 mN/m) is not low enough for soft lithography procedures that require high fidelity. For this reason, the patterned surface of PDMS-based molds is often fluorinated using a plasma treatment followed by vapor deposition of a fluoroalkyl trichlorosilane. See Xia, Y., et al., *Angew. Chem. Int. Ed.*, 1998, 37, 550-575. These fluorine-treated silicones swell, however, when exposed to organic solvents.

Third, the most commonly-used commercially available form of the material used in PDMS molds, e.g., Sylgard 1840® (Dow Corning Corporation, Midland, Mich., United States of America) has a modulus that is too low (approximately 1.5 MPa) for many applications. The low modulus of these commonly used PDMS materials results in sagging and bending of features and, as such, is not well suited for processes that require precise pattern placement and alignment. Although researchers have attempted to address this last problem, see Odom, T. W., et al., *J. Am. Chem. Soc.*, 2002, 124, 12112-12113; Odom, T. W. et al., *Langmuir*, 2002, 18, 5314-5320; Schmid, H., et al., *Macromolecules*, 2000, 33, 3042-3049; Csucs, G., et al., *Langmuir*, 2003, 19, 6104-6109; Trimbach, D., et al., *Langmuir*, 2003, 19, 10957-10961, the materials chosen still exhibit poor solvent resistance and require fluorination steps to allow for the release of the mold.

Rigid materials, such as quartz glass and silicon, also have been used in imprint lithography. See Xia, Y., et al., *Angew. Chem. Int. Ed.*, 1998, 37, 550-575; Resnick, D. J., et al., *Semiconductor International*, 2002, June, 71-78; McClelland, G. M., et al., *Appl. Phys. Lett.*, 2002, 81, 1483; Chou, S. Y., et al., *J. Vac. Sci. Technol. B*, 1996, 14, 4129; Otto, M., et al., *Microelectron. Eng.*, 2001, 57, 361; and Bailey, T., et al., *J. Vac. Sci. Technol.*, B, 2000, 18, 3571; Chou, S. Y., et al., *Science*, 1996, 272, 85-87; Von Werne, T. A., et al., *J. Am. Chem. Soc.*, 2003, 125, 3831-3838; Resnick, D. J., et al., *J. Vac. Sci. Technol. B*, 2003, 21, 2624-2631. These materials are superior to PDMS in modulus and swelling resistance, but lack flexibility. Such lack of flexibility inhibits conformal contact with the substrate and causes defects in the mask and/or replicate during separation.

Another drawback of rigid materials is the necessity to use a costly and difficult to fabricate hard mold, which is typically made by using conventional photolithography or electron beam (e-beam) lithography. See Chou, S. Y., et al., *J. Vac. Sci. Technol. B*, 1996, 14, 4129. More recently, the need to repeatedly use expensive quartz glass or silicon molds in NCM processes has been eliminated by using an acrylate-based mold generated from casting a photopolymerizable monomer mixture against a silicon master. See McClelland, G. M., et al., *Appl. Phys. Lett.*, 2002, 81, 1483, and Jung, G. Y., et al., *Nanoletters*, 2004, ASAP. This approach also can be limited by swelling of the mold in organic solvents.

Despite such advances, other disadvantages of fabricating molds from rigid materials include the necessity to use fluorination steps to lower the surface energy of the mold, see Resnick, D. J., et al., *Semiconductor International*, 2002, June, 71-78, and the inherent problem of releasing a rigid mold from a rigid substrate without breaking or damaging the mold or the substrate. See Resnick, D. J., et al., *Semiconductor International*, 2002, June, 71-78; Bietsch, A., J. Appl. Phys., 2000, 88, 4310-4318. Khang, D. Y., et al., *Langmuir*, 2004, 20, 2445-2448, have reported the use of rigid molds composed of thermoformed Teflon AF® (DuPont, Wilmington, Del., United States of America) to address the surface energy problem. Fabrication of these molds, however, requires high temperatures and pressures in a melt press, a process that could be damaging to the delicate features on a silicon wafer master. Additionally, these molds still exhibit the intrinsic drawbacks of other rigid materials as outlined hereinabove.

Further, a clear and important limitation of fabricating structures on semiconductor devices using molds or templates made from hard materials is the usual formation of a residual or "scum" layer that forms when a rigid template is brought into contact with a substrate. Even with elevated applied forces, it is very difficult to completely displace liquids during this process due to the wetting behavior of the liquid being molded, which results in the formation of a scum layer. Thus, there is a need in the art for a method of fabricating a pattern or a structure on a substrate, such as a semiconductor device, which does not result in the formation of a scum layer.

The fabrication of solvent resistant, microfluidic devices with features on the order of hundreds of microns from photocurable perfluoropolyether (PFPE) has been reported. See Rolland, J. P., et al., *J. Am. Chem. Soc.*, 2004, 126, 2322-2323. PFPE-based materials are liquids at room temperature and can be photochemically cross-linked to yield tough, durable elastomers. Further, PFPE-based materials are highly fluorinated and resist swelling by organic solvents, such as methylene chloride, tetrahydrofuran, toluene, hexanes, and acetonitrile among others, which are desirable for use in microchemistry platforms based on elastomeric microfluidic devices. There is a need in the art, however, to apply PFPE-based materials to the fabrication of nanoscale devices for related reasons.

Further, there is a need in the art for improved methods for forming a pattern on a substrate, such as method employing a patterned mask. See U.S. Pat. No. 4,735,890 to Nakane et al.; U.S. Pat. No. 5,147,763 to Kamitakahara et al.; U.S. Pat. No. 5,259,926 to Kuwabara et al.; and International PCT Publication No. WO 99/54786 to Jackson et al., each of which is incorporated herein by reference in their entirety.

There also is a need in the art for an improved method for forming isolated structures that can be considered "engineered" structures, including but not limited to particles, shapes, and parts. Using traditional IL methods, the scum layer that almost always forms between structures acts to connect or link structures together, thereby making it difficult, if not impossible, to fabricate and/or harvest isolated structures.

There also is a need in the art for an improved method for forming micro- and nanoscale charged particles, in particular polymer electrets. The term "polymer electrets" refers to dielectrics with stored charge, either on the surface or in the bulk, and dielectrics with oriented dipoles, frozen-in, ferrielectric, or ferroelectric. On the macro scale, such materials are used, for example, for electronic packaging and charge electret devices, such as microphones and the like. See Kressman, R., et al., *Space-Charge Electrets*, Vol. 2, Laplacian Press, 1999; and Harrison, J. S., et al., *Piezoelectic Polymers*, NASA/CR-2001-211422, ICASE Report No. 2001-43. Poly (vinylidene fluoride) (PVDF) is one example of a polymer electret material. In addition to PVDF, charge electret materials, such as polypropylene (PP), Teflon-fluorinated ethylene propylene (FEP), and polytetrafluoroethylene (PTFE), also are considered polymer electrets.

Further, there is a need in the art for improved methods for delivering therapeutic agents, such as drugs, non-viral gene vectors, DNA, RNA, RNAi, and viral particles, to a target. See *Biomedical Polymers*, Shalaby, S. W., ed., Harner/Gardner Publications, Inc., Cincinnati, Ohio, 1994; *Polymeric Biomaterials*, Dumitrin, S., ed., Marcel Dekkar, Inc., New York, N.Y., 1994; Park, K., et al., *Biodegradable Hydrogels for Drug Delivery*, Technomic Publishing Company, Inc., Lancaster, Pa., 1993; Gumargalieva, et al., *Biodegradation and Biodeterioration of Polymers: Kinetic Aspects*, Nova Science Publishers, Inc., Commack, N.Y., 1998; *Controlled Drug Delivery*, American Chemical Society Symposium Series 752, Park, K., and Mrsny, R. J., eds., Washington, D.C., 2000; *Cellular Drug Delivery: Principles and Practices*, Lu, D. R., and Oie, S., eds., Humana Press, Totowa, N.J., 2004; and *Bioreversible Carriers in Drug Design: Theory and Applications*, Roche, E. B., ed., Pergamon Press, New York, N.Y., 1987. For a description of representative therapeutic agents for use in such delivery methods, see U.S. Pat. No. 6,159,443 to Hallahan, which is incorporated herein by reference in its entirety.

In sum, there exists a need in the art to identify new materials for use in imprint lithographic techniques. More particularly, there is a need in the art for methods for the fabrication of structures at the tens of micron level down to sub-100 nm feature sizes.

SUMMARY

In some embodiments, the presently disclosed subject matter describes a method for forming one or more particles, the method comprising:
 (a) providing a patterned template and a substrate, wherein the patterned template comprises a patterned template surface having a plurality of recessed areas formed therein;
 (b) disposing a volume of liquid material in or on at least one of:
  (i) the patterned template surface; and
  (ii) the plurality of recessed areas; and
 (c) forming one or more particles by one of:
  (i) contacting the patterned template surface with the substrate and treating the liquid material; and
  (ii) treating the liquid material.

In some embodiments of the method for forming one or more particles, the patterned template comprises a solvent resistant, low surface energy polymeric material derived from casting low viscosity liquid materials onto a master template and then curing the low viscosity liquid materials to generate a patterned template. In some embodiments, the patterned template comprises a solvent resistant elastomeric material.

In some embodiments, at least one of the patterned template and substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the presently disclosed subject matter comprises a method for delivering a therapeutic agent to a target, the method comprising:
 (a) providing a particle formed by the method described hereinabove;
 (b) admixing the therapeutic agent with the particle; and
 (c) delivering the particle comprising the therapeutic agent to the target.

In some embodiments of the method for delivering a therapeutic agent to a target, the therapeutic agent is selected from one of a drug and genetic material. In some embodiments, the genetic material is selected from the group consisting of a non-viral gene vector, DNA, RNA, RNAi, and a viral particle. In some embodiments, the particle comprises a biodegradable polymer, wherein the biodegradable polymer is selected from the group consisting of a polyester, a polyanhydride, a polyamide, a phosphorous-based polymer, a poly(cyanoacrylate), a polyurethane, a polyorthoester, a polydihydropyran, and a polyacetal.

In some embodiments, the presently disclosed subject matter describes a method for forming a pattern on a substrate, the method comprising:
 (a) providing a patterned template and a substrate, wherein the patterned template comprises a patterned template surface having a plurality of recessed areas formed therein;
 (b) disposing a volume of liquid material in or on at least one of:
  (i) the patterned template surface; and
  (ii) the plurality of recessed areas;
 (c) contacting the patterned template surface with the substrate; and
 (d) treating the liquid material to form a pattern on the substrate.

In some embodiments of the method for forming a pattern on a substrate, the patterned template comprises a solvent resistant, low surface energy polymeric material derived from casting low viscosity liquid materials onto a master template and then curing the low viscosity liquid materials to generate a patterned template. In some embodiments, the patterned template comprises a solvent resistant elastomeric material.

In some embodiments, at least one of the patterned template and substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

Accordingly, it is an object of the present invention to provide a novel method of making micro-, nano-, and sub-nanostructures. This and other objects are achieved in whole or in part by the presently disclosed subject matter.

An object of the presently disclosed subject matter having been stated hereinabove, other aspects and objects will become evident as the description proceeds when taken in connection with the accompanying Drawings and Examples as best described herein below.

BRIEF DESCRIPTION OF THE DRAWINGS

FIG. 4A represents the electrostatic charging of the molded particle during polymerization or crystallization; FIG. 4B represents a charged nano-disc; FIG. 4C represents typical random juxtapositioning of uncharged nano-discs; and FIG. 4D represents the spontaneous aggregation of charged nano-discs into chain-like structures.

FIG. 27 is a scanning electron micrograph of 500-nm conical shaped Ppy particles.

FIGS. 28A-28C are fluorescence confocal micrographs of 200-nm isolated trapezoidal particles of PEG diacrylate that contain fluorescently tagged DNA. FIG. 28A is a fluorescent confocal micrograph of 200 nm trapezoidal PEG nanoparticles which contain 24-mer DNA strands that are tagged with CY-3. FIG. 28B is optical micrograph of the 200-nm isolated trapezoidal particles of PEG diacrylate that contain fluorescently tagged DNA. FIG. 28C is the overlay of the images provided in FIGS. 28A and 28B, showing that every particle contains DNA.

FIG. 31A is a scanning electron micrograph of silicon/silicon oxide masters of 3 micron arrows. FIG. 31B is a scanning electron micrograph of silicon/silicon oxide masters of 200-nm×800-nm bars.

FIG. 32A is a SU-8 master. FIG. 32B is a PFPE-DMA mold templated from a photolithographic master.

FIG. 33A is a master. FIG. 33B is a PFPE-DMA mold templated from a virus master.

FIG. 34A is a polystyrene-polyisoprene block copolymer micelle. FIG. 34B is a PFPE-DMA mold templated from a micelle master.

FIGS. 35A and 35B are an atomic force micrograph of mold fabrication from brush polymer masters. FIG. 35A is a brush polymer master. FIG. 35B is a PFPE-DMA mold templated from a brush polymer master.

DETAILED DESCRIPTION

Figure 1A:
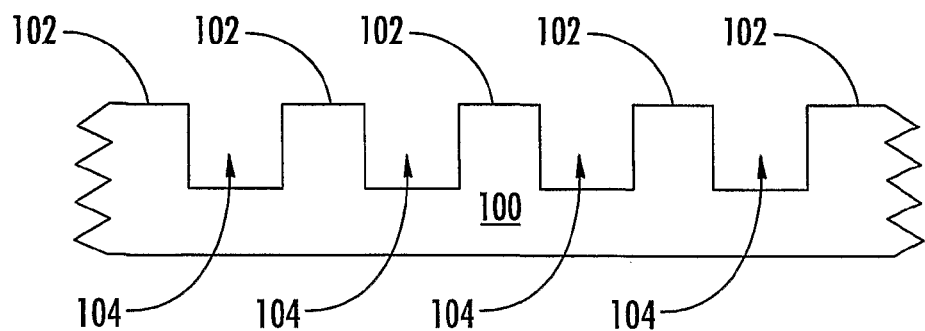
FIGS. 1A-1D are a schematic representation of an embodiment of the presently disclosed method for preparing a patterned template.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Materials

The presently disclosed subject matter broadly describes solvent resistant, low surface energy polymeric materials, derived from casting low viscosity liquid materials onto a master template and then curing the low viscosity liquid materials to generate a patterned template for use in high-resolution soft or imprint lithographic applications, such as micro- and nanoscale replica molding. In some embodiments, the patterned temp late comprises a solvent resistant, elastomer-based material, such as but not limited to a fluorinated elastomer-based material.

Further, the presently disclosed subject matter describes the first nano-contact molding of organic materials to generate high fidelity features using an elastomeric mold. Accordingly, the presently disclosed subject matter describes a method for producing free-standing, isolated micro- and nanostructures of any shape using soft or imprint lithography techniques. Representative micro- and nanostructures include but are not limited to micro- and nanoparticles, and micro- and nano-patterned substrates.

The nanostructures described by the presently disclosed subject matter can be used in several applications, including, but not limited to, semiconductor manufacturing, such as molding etch barriers without scum layers for the fabrication of semiconductor devices; crystals; materials for displays; photovoltaics; a solar cell device; optoelectronic devices; routers; gratings; radio frequency identification (RFID) devices; catalysts; fillers and additives; detoxifying agents; etch barriers; atomic force microscope (AFM) tips; parts for nano-machines; the delivery of a therapeutic agent, such as a drug or genetic material; cosmetics; chemical mechanical planarization (CMP) particles; and porous particles and shapes of any kind that will enable the nanotechnology industry.

Representative solvent resistant elastomer-based materials include but are not limited to fluorinated elastomer-based materials. As used herein, the term "solvent resistant" refers to a material, such as an elastomeric material that neither swells nor dissolves in common hydrocarbon-based organic solvents or acidic or basic aqueous solutions. Representative fluorinated elastomer-based materials include but are not limited to perfluoropolyether (PFPE)-based materials. A photocurable liquid PFPE exhibits desirable properties for soft lithography. A representative scheme for the synthesis and photocuring of functional PFPEs is provided in Scheme 1.

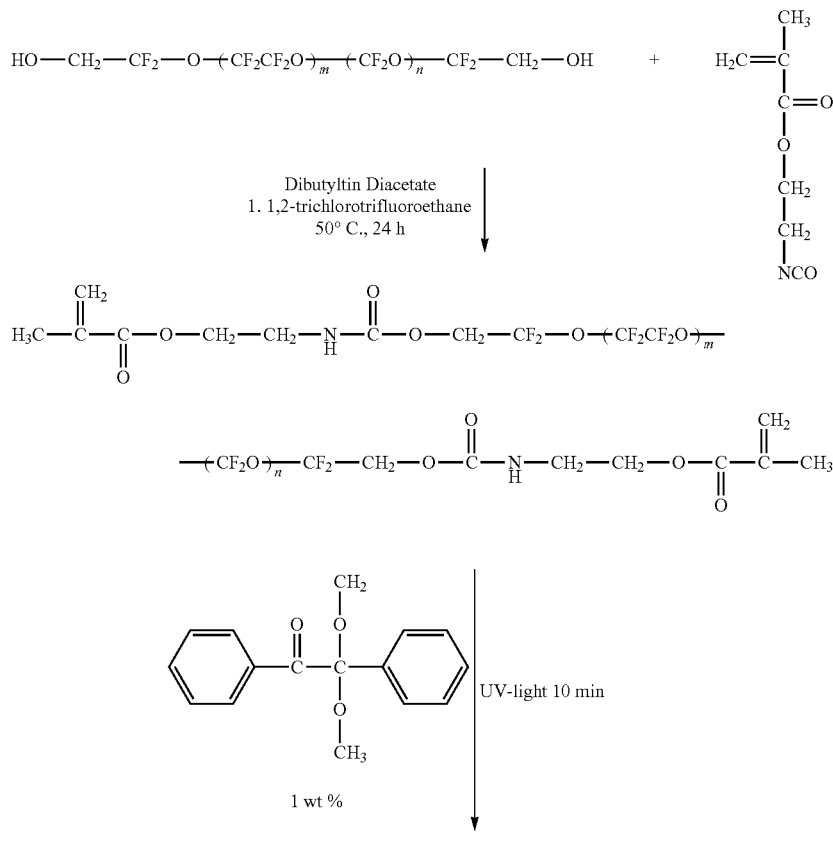

Scheme 1. Synthesis and Photocuring of Functional Perfluoropolyethers.

Additional schemes for the synthesis of functional perfluoropolyethers are provided in Examples 7.1 through 7.6.

This PFPE material has a low surface energy (for example, about 12 mN/m); is non-toxic, UV transparent, and highly gas permeable; and cures into a tough, durable, highly fluorinated elastomer with excellent release properties and resistance to

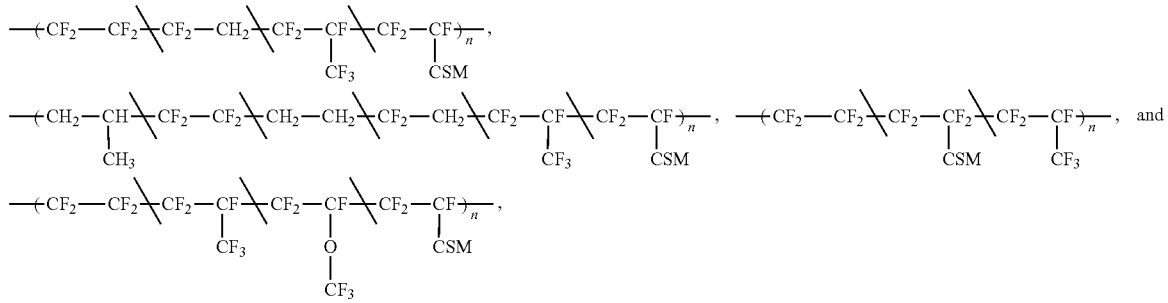

swelling. The properties of these materials can be tuned over a wide range through the judicious choice of additives, fillers, reactive co-monomers, and functionalization agents. Such properties that are desirable to modify, include, but are not limited to, modulus, tear strength, surface energy, permeability, functionality, mode of cure, solubility and swelling characteristics, and the like. The non-swelling nature and easy release properties of the presently disclosed PFPE materials allows for nanostructures to be fabricated from any material. Further, the presently disclosed subject matter can be expanded to large scale rollers or conveyor belt technology or rapid stamping that allow for the fabrication of nanostructures on an industrial scale.

In some embodiments, the patterned template comprises a solvent resistant, low surface energy polymeric material derived from casting low viscosity liquid materials onto a master template and then curing the low viscosity liquid materials to generate a patterned template. In some embodiments, the patterned template comprises a solvent resistant elastomeric material.

In some embodiments, at least one of the patterned template and substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material comprises a backbone structure selected from the group consisting of:

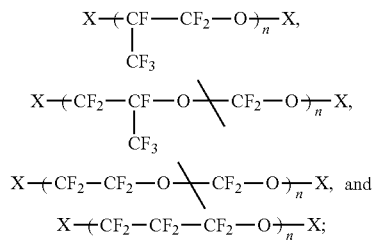

wherein X is present or absent, and when present comprises an endcapping group.

In some embodiments, the fluoroolefin material is selected from the group consisting of:

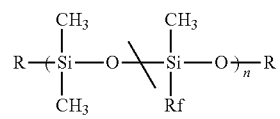

wherein CSM comprises a cure site monomer.

In some embodiments, the fluoroolefin material is made from monomers which comprise tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material comprises a fluoroalkyl functionalized polydimethylsiloxane (PDMS) having the following structure:

$$R\text{---}(\text{Si}(CH_3)_2\text{---}O\text{---}\text{Si}(CH_3)(Rf)\text{---}O)_n\text{---}R$$

wherein:

R is selected from the group consisting of an acrylate, a methacrylate, and a vinyl group; and Rf comprises a fluoroalkyl chain.

In some embodiments, the styrenic material comprises a fluorinated styrene monomer selected from the group consisting of:

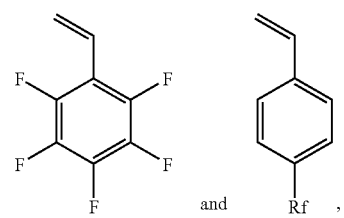

wherein Rf comprises a fluoroalkyl chain.

In some embodiments, the acrylate material comprises a fluorinated acrylate or a fluorinated methacrylate having the following structure:

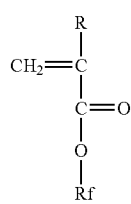

wherein:

R is selected from the group consisting of H, alkyl, substituted alkyl, aryl, and substituted aryl; and Rf comprises a fluoroalkyl chain.

In some embodiments, the triazine fluoropolymer comprises a fluorinated monomer. In some embodiments, the fluorinated monomer or fluorinated oligomer that can be polymerized or crosslinked by a metathesis polymerization reaction comprises a functionalized olefin. In some embodiments, the functionalized olefin comprises a functionalized cyclic olefin.

In some embodiments, at least one of the patterned template and the substrate has a surface energy lower than 18 mN/m. In some embodiments, at least one of the patterned template and the substrate has a surface energy lower than 15 mN/m.

From a property point of view, the exact properties of these molding materials can be adjusted by adjusting the composition of the ingredients used to make the materials. In particular the modulus can be adjusted from low (approximately 1 MPa) to multiple GPa.

II. Formation of Isolated Micro- and/or Nanoparticles

In some embodiments, the presently disclosed subject matter provides a method for making isolated micro- and/or nanoparticles. In some embodiments, the process comprises initially forming a patterned substrate. Turning now to FIG. 1A, a patterned master 100 is provided. Patterned master 100 comprises a plurality of non-recessed surface areas 102 and a plurality of recesses 104. In some embodiments, patterned master 100 comprises an etched substrate, such as a silicon wafer, which is etched in the desired pattern to form patterned master 100.

Figure 1B:
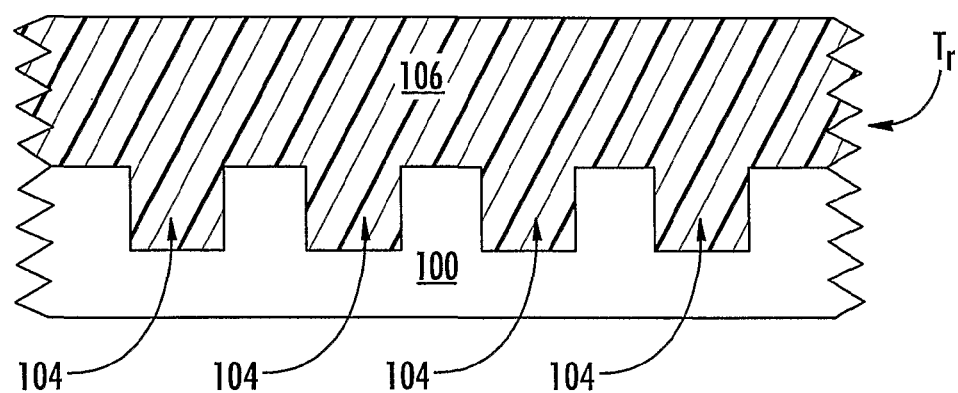

Referring now to FIG. 1B, a liquid material 106, for example, a liquid fluoropolymer composition, such as a PFPE-based precursor, is then poured onto patterned master 100. Liquid material 106 is treated by treating process $T_r$, for example exposure to UV light, thereby forming a treated liquid material 108 in the desired pattern.

Figure 1C:
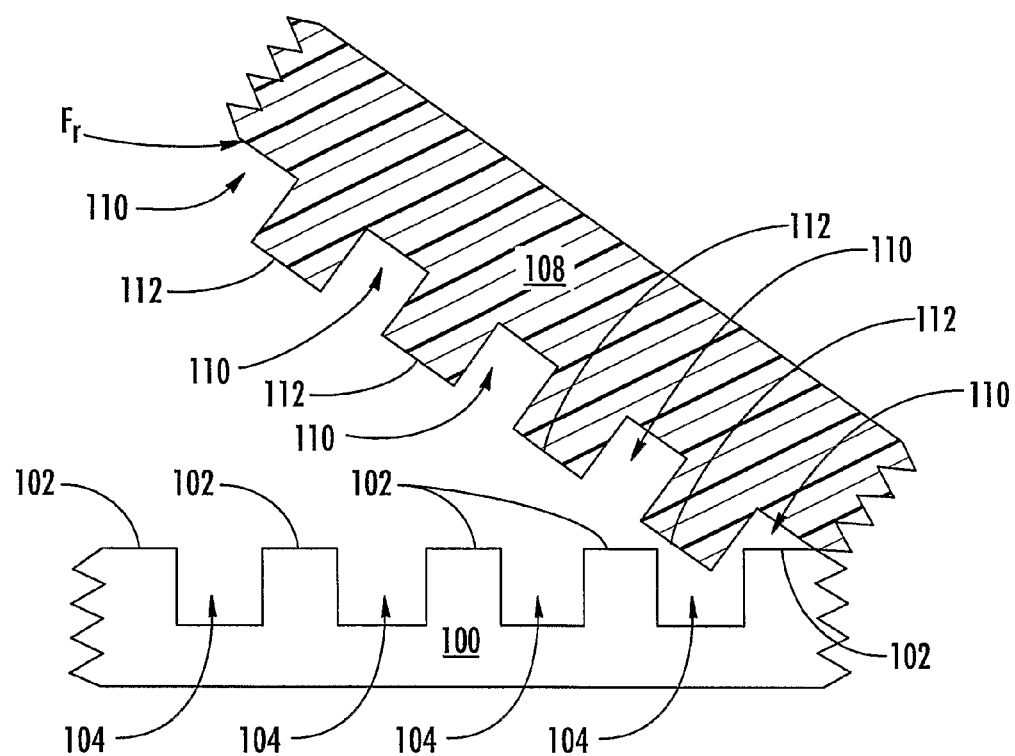
Figure 1D:
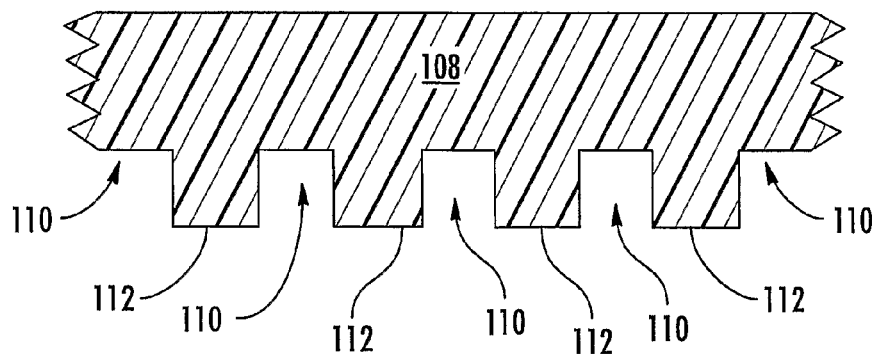

Referring now to FIGS. 1C and 1D, a force $F_r$ is applied to treated liquid material 108 to remove it from patterned master 100. As shown in FIGS. 1C and 1D, treated liquid material 108 comprises a plurality of recesses 110, which are mirror images of the plurality of non-recessed surface areas 102 of patterned master 100. Continuing with FIGS. 1C and 1D, treated liquid material 108 comprises a plurality of first patterned surface areas 112, which are mirror images of the plurality of recesses 104 of patterned master 100. Treated liquid material 108 can now be used as a patterned template for soft lithography and imprint lithography applications. Accordingly, treated liquid material 108 can be used as a patterned template for the formation of isolated micro- and nanoparticles. For the purposes of FIGS. 1A-1D, 2A-2E, and 3A-3F, the numbering scheme for like structures is retained throughout.

Figure 2A:
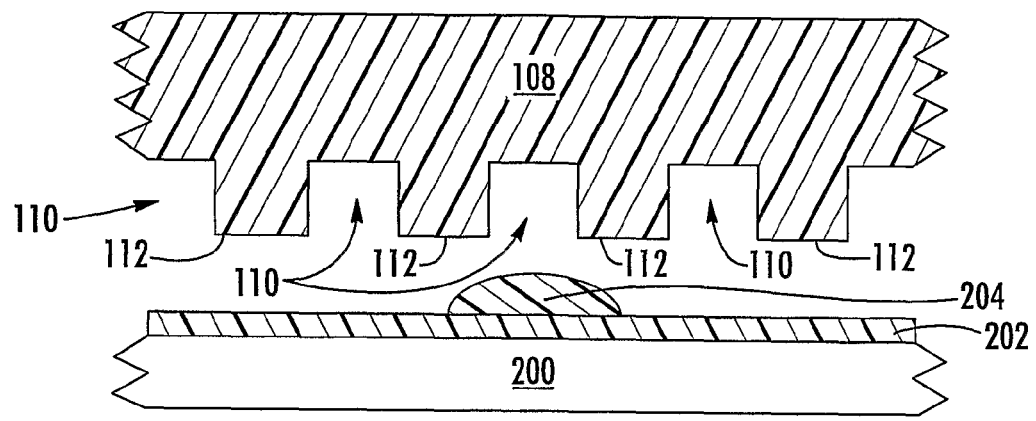
FIGS. 2A-2F are a schematic representation of the presently disclosed method for forming one or more micro- and/or nanoscale particles.

Referring now to FIG. 2A, in some embodiments, a substrate 200, for example, a silicon wafer, is treated or is coated with a non-wetting material 202. In some embodiments, non-wetting material 202 comprises an elastomer (such a solvent resistant elastomer, including but not limited to a PFPE elastomer) that can be further exposed to UV light and cured to form a thin, non-wetting layer on the surface of substrate 200. Substrate 200 also can be made non-wetting by treating substrate 200 with non-wetting agent 202, for example a small molecule, such as an alkyl- or fluoroalkyl-silane, or other surface treatment. Continuing with FIG. 2A, a droplet 204 of a curable resin, a monomer, or a solution in which the desired particles will be formed is then placed on the coated substrate 200.

Figure 2B:
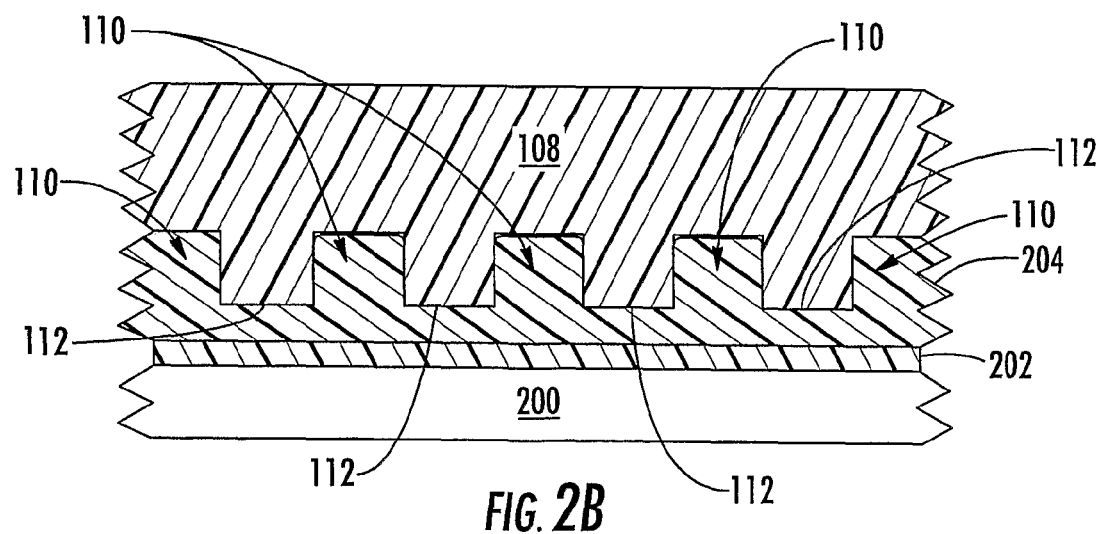

Referring now to FIG. 2A and FIG. 2B, patterned template 108 (as shown in FIG. 1D) is then contacted with droplet 204 so that droplet 204 fills the plurality of recessed areas 110 of patterned template 108.

Figure 2C:
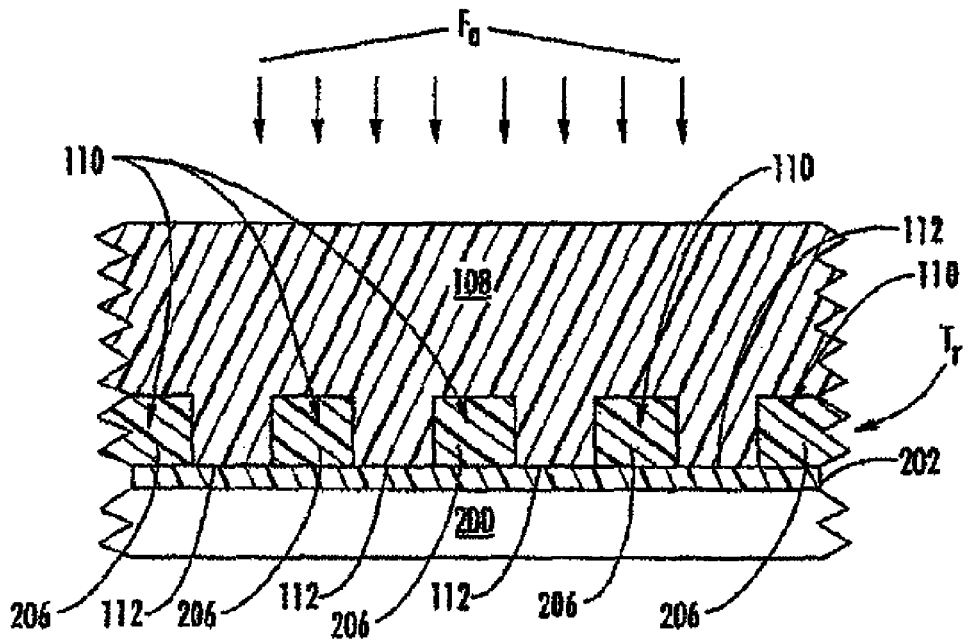
Figure 2D:
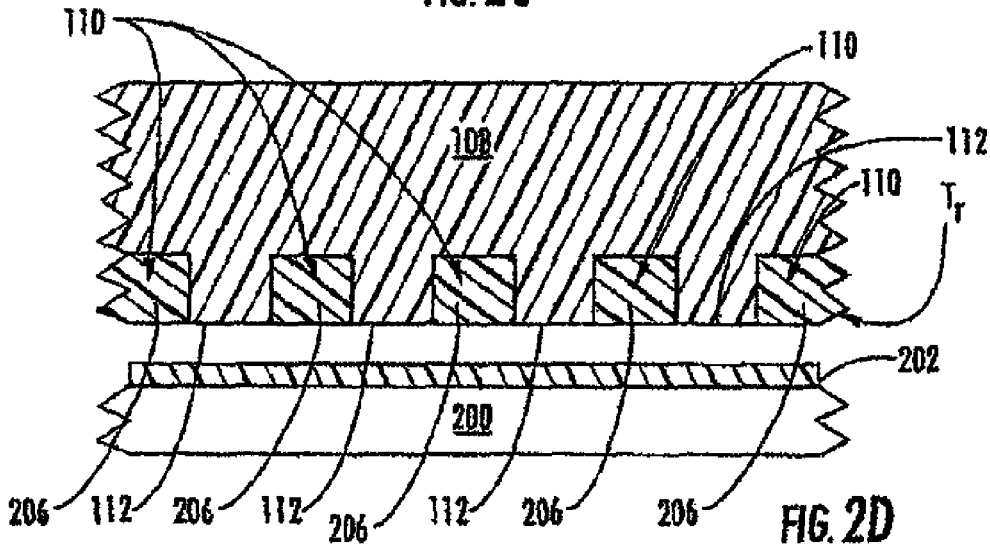

Referring now to FIGS. 2C and 2D, a force $F_a$ is applied to patterned template 108. While not wishing to be bound by any particular theory, once force $F_a$ is applied, the affinity of patterned template 108 for non-wetting coating or surface treatment 202 on substrate 200 in combination with the non-wetting behavior of patterned template 108 and surface treated or coated substrate 200 causes droplet 204 to be excluded from all areas except for recessed areas 110. Further, in embodiments essentially free of non-wetting or low wetting material 202 with which to sandwich droplet 204, a "scum" layer that interconnects the objects being stamped forms.

Continuing with FIGS. 2C and 2D, the material filling recessed areas 110, e.g., a resin, monomer, solvent, and combinations thereof, is then treated by a treating process $T_r$, e.g., photocured through patterned template 108 or thermally cured while under pressure, to form a plurality of micro- and/or nanoparticles 206. In some embodiments, a material, including but not limited to a polymer, an organic compound, or an inorganic compound, can be dissolved in a solvent, patterned using patterned template 108, and the solvent can be released.

Continuing with FIGS. 2C and 2D, once the material filling recessed areas 110 is treated, patterned template 108 is removed from substrate 200. Micro- and/or nanoparticles 206 are confined to recessed areas 110 of patterned template 108. In some embodiments, micro- and/or nanoparticles 206 can be retained on substrate 200 in defined regions once patterned template 108 is removed. This embodiment can be used in the manufacture of semiconductor devices where essentially scum-layer free features could be used as etch barriers or as conductive, semiconductive, or dielectric layers directly, mitigating or reducing the need to use traditional and expensive photolithographic processes.

Figure 2E:
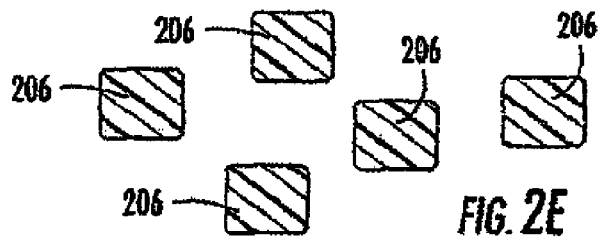

Referring now to FIGS. 2D and 2E, micro- and/or nanoparticles 206 can be removed from patterned template 108 to provide freestanding particles by a variety of methods, which include but are not limited to: (1) applying patterned template 108 to a surface that has an affinity for the particles 206; (2) deforming patterned template 108, or using other mechanical methods, including sonication, in such a manner that the particles 206 are naturally released from patterned template 108; (3) swelling patterned template 108 reversibly with supercritical carbon dioxide or another solvent that will extrude the particles 206; and (4) washing patterned template 108 with a solvent that has an affinity for the particles 206 and will wash them out of patterned template 108.

Figure 2F:
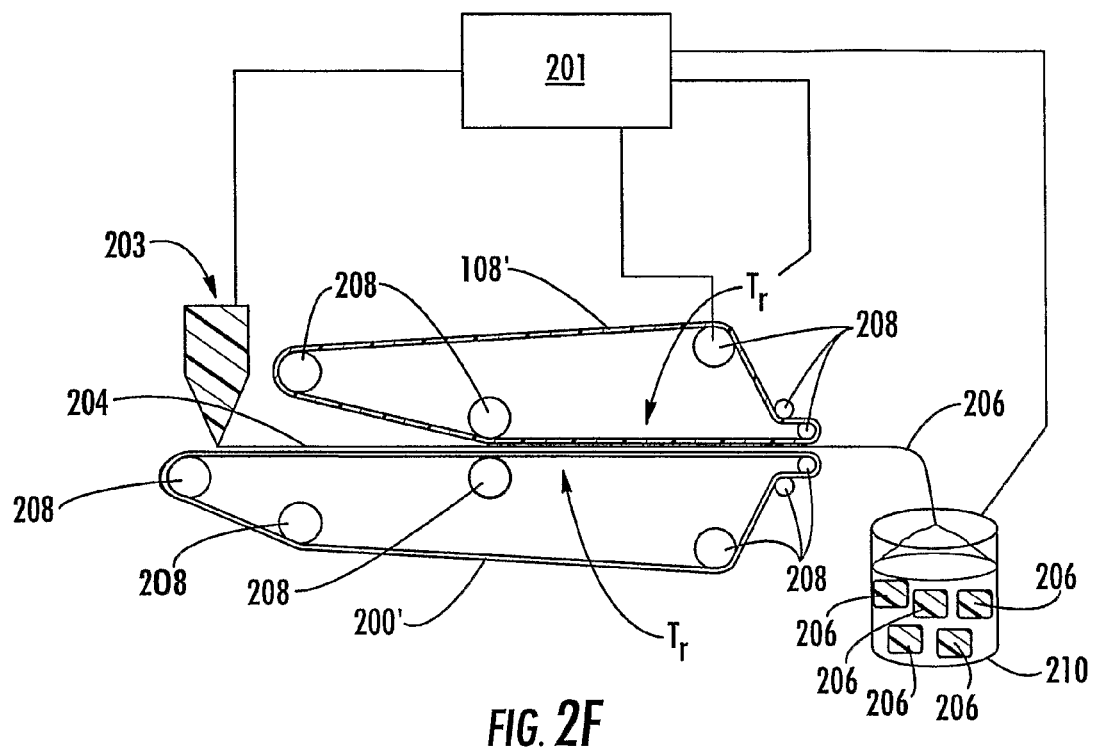

In some embodiments, the method comprises a batch process. In some embodiments, the batch process is selected from one of a semi-batch process and a continuous batch process. Referring now to FIG. 2F, an embodiment of the presently disclosed subject matter wherein particles 206 are produced in a continuous process is schematically presented. An apparatus 199 is provided for carrying out the process. Indeed, while FIG. 2F schematically presents a continuous process for particles, apparatus 199 can be adapted for batch processes, and for providing a pattern on a substrate continuously or in batch, in accordance with the presently disclosed subject matter and based on a review of the presently disclosed subject matter by one of ordinary skill in the art.

Continuing, then, with FIG. 2F, droplet 204 of liquid material is applied to substrate 200' via reservoir 203. Substrate 200' can be coated or not coated with a non-wetting agent. Substrate 200' and pattern template 108' are placed in a spaced relationship with respect to each other and are also operably disposed with respect to each other to provide for the conveyance of droplet 204 between patterned template 108' and substrate 200'. Conveyance is facilitated through the provision of pulleys 208, which are in operative communication with controller 201. By way of representative non-limiting examples, controller 201 can comprise a computing system, appropriate software, a power source, a radiation source, and/or other suitable devices for controlling the functions of apparatus 199. Thus, controller 201 provides for power for and other control of the operation of pulleys 208 to provide for the conveyance of droplet 204 between patterned template 108' and substrate 200'. Particles 206 are formed and treated between substrate 200' and patterned template 108' by a treating process $T_R$, which is also controlled by controller 201. Particles 206 are collected in an inspecting device 210, which is also controlled by controller 201. Inspecting device 210 provides for one of inspecting, measuring, and both inspecting and measuring one or more characteristics of particles 206. Representative examples of inspecting devices 210 are disclosed elsewhere herein.

Thus, in some embodiments, the method for forming one or more particles comprises:

(a) providing a patterned template and a substrate, wherein the patterned template comprises a first patterned template surface having a plurality of recessed areas formed therein;

(b) disposing a volume of liquid material in or on at least one of:
  (i) the first patterned template surface; and
  (ii) the plurality of recessed areas; and (c) forming one or more particles by one of:
  (i) contacting the patterned template surface with the substrate and treating the liquid material; and
  (ii) treating the liquid material.

In some embodiments of the method for forming one or more particles, the patterned template comprises a solvent resistant, low surface energy polymeric material derived from casting low viscosity liquid materials onto a master template and then curing the low viscosity liquid materials to generate a patterned template. In some embodiments, the patterned template comprises a solvent resistant elastomeric material.

In some embodiments, at least one of the patterned template and substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material comprises a backbone structure selected from the group consisting of:

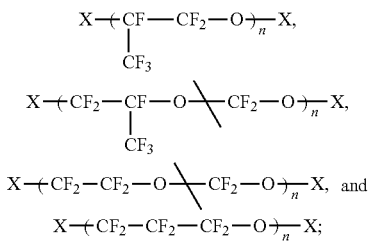

wherein X is present or absent, and when present comprises an endcapping group.

In some embodiments, the fluoroolefin material is selected from the group consisting of:

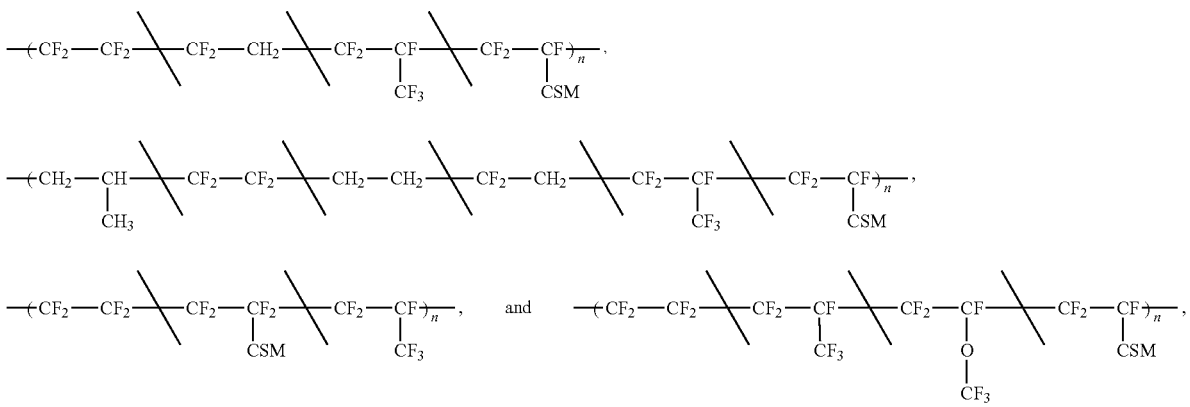

wherein CSM comprises a cure site monomer.

In some embodiments, the fluoroolefin material is made from monomers which comprise tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material comprises a fluoroalkyl functionalized polydimethylsiloxane (PDMS) having the following structure:

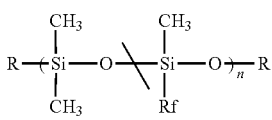

wherein:

R is selected from the group consisting of an acrylate, a methacrylate, and a vinyl group; and Rf comprises a fluoroalkyl chain.

In some embodiments, the styrenic material comprises a fluorinated styrene monomer selected from the group consisting of:

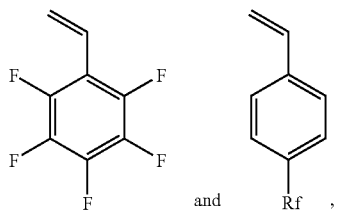

wherein Rf comprises a fluoroalkyl chain.

In some embodiments, the acrylate material comprises a fluorinated acrylate or a fluorinated methacrylate having the following structure:

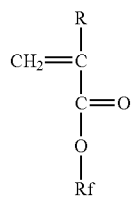

wherein:

R is selected from the group consisting of H, alkyl, substituted alkyl, aryl, and substituted aryl; and Rf comprises a fluoroalkyl chain.

In some embodiments, the triazine fluoropolymer comprises a fluorinated monomer. In some embodiments, the fluorinated monomer or fluorinated oligomer that can be polymerized or crosslinked by a metathesis polymerization reaction comprises a functionalized olefin. In some embodiments, the functionalized olefin comprises a functionalized cyclic olefin.

In some embodiments, at least one of the patterned template and the substrate has a surface energy lower than 18 mN/m. In some embodiments, at least one of the patterned template and the substrate has a surface energy lower than 15 mN/m.

In some embodiments, the substrate is selected from the group consisting of a polymer material, an inorganic material, a silicon material, a quartz material, a glass material, and surface treated variants thereof. In some embodiments, the substrate comprises a patterned area.

In some embodiments, the plurality of recessed areas comprises a plurality of cavities. In some embodiments, the plurality of cavities comprises a plurality of structural features. In some embodiments, the plurality of structural features has a dimension ranging from about 10 microns to about 1 nanometer in size. In some embodiments, the plurality of structural features has a dimension ranging from about 10 microns to about 1 micron in size. In some embodiments, the plurality of structural features has a dimension ranging from about 1 micron to about 100 nm in size. In some embodiments, the plurality of structural features has a dimension ranging from about 100 nm to about 1 nm in size.

In some embodiments, the patterned template comprises a patterned template formed by a replica molding process. In some embodiments, the replica molding process comprises: providing a master template; contacting a liquid material with the master template; and curing the liquid material to form a patterned template.

In some embodiments, the master template is selected from the group consisting of: a template formed from a lithography process; a naturally occurring template; and combinations thereof. In some embodiments, the natural template is selected from one of a biological structure and a self-assembled structure. In some embodiments, the one of a biological structure and a self-assembled structure is selected from the group consisting of a naturally occurring crystal, an enzyme, a virus, a protein, a micelle, and a tissue surface.

In some embodiments, the method comprises modifying the patterned template surface by a surface modification step. In some embodiments, the surface modification step is selected from the group consisting of a plasma treatment, a chemical treatment, and an adsorption process. In some embodiments, the adsorption process comprises adsorbing molecules selected from the group consisting of a polyelectrolyte, a poly(vinylalcohol), an alkylhalosilane, and a ligand.

In some embodiments, the method comprises positioning the patterned template and the substrate in a spaced relationship to each other such that the patterned template surface and the substrate face each other in a predetermined alignment.

In some embodiments, the liquid material is selected from the group consisting of a polymer, a solution, a monomer, a plurality of monomers, a polymerization initiator, a polymerization catalyst, an inorganic precursor, a metal precursor, a pharmaceutical agent, a tag, a magnetic material, a paramagnetic material, a ligand, a cell penetrating peptide, a porogen, a surfactant, a plurality of immiscible liquids, a solvent, a charged species, and combinations thereof.

In some embodiments, the pharmaceutical agent is selected from the group consisting of a drug, a peptide, RNAi, and DNA. In some embodiments, the tag is selected from the group consisting of a fluorescence tag, a radiolabeled tag, and a contrast agent. In some embodiments, the ligand comprises a cell targeting peptide.

In some embodiments, the liquid material comprises a non-wetting agent. In some embodiments, the liquid material comprises one phase. In some embodiments, the liquid material comprises a plurality of phases. In some embodiments, the liquid material is selected from the group consisting of multiple liquids, multiple immiscible liquids, surfactants, dispersions, emulsions, micro-emulsions, micelles, particulates, colloids, porogens, active ingredients, and combinations thereof.

In some embodiments, the disposing of the volume of liquid material on one of the patterned template and the substrate is regulated by a spreading process. In some embodiments, the spreading process comprises:

(a) disposing a first volume of liquid material on one of the patterned template and the substrate to form a layer of liquid material thereon; and (b) drawing an implement across the layer of liquid material to:

(i) remove a second volume of liquid material from the layer of liquid material on the one of the patterned template and the substrate; and
(ii) leave a third volume of liquid material on the one of the patterned template and the substrate.

In some embodiments, an article is contacted with the layer of liquid material and a force is applied to the article to thereby remove the liquid material from the one of the patterned material and the substrate. In some embodiments, the article is selected from the group consisting of a roller and a "squeegee" blade. In some embodiments, the liquid material is removed by some other mechanical means.

In some embodiments, the contacting of the patterned template surface with the substrate forces essentially all of the disposed liquid material from between the patterned template surface and the substrate.

In some embodiments, the treating of the liquid material comprises a process selected from the group consisting of a thermal process, a photochemical process, and a chemical process.

In some embodiments as described in detail herein below, the method further comprises:
(a) reducing the volume of the liquid material disposed in the plurality of recessed areas by one of:
   (i) applying a contact pressure to the patterned template surface; and
   (ii) allowing a second volume of the liquid to evaporate or permeate through the template;
(b) removing the contact pressure applied to the patterned template surface;
(c) introducing gas within the recessed areas of the patterned template surface;
(d) treating the liquid material to form one or more particles within the recessed areas of the patterned template surface; and
(e) releasing the one or more particles.

In some embodiments, the releasing of the one or more particles is performed by one of:
(a) applying the patterned template to a substrate, wherein the substrate has an affinity for the one or more particles;
(b) deforming the patterned template such that the one or more particles is released from the patterned template;
(c) swelling the patterned template with a first solvent to extrude the one or more particles;
(d) washing the patterned template with a second solvent, wherein the second solvent has an affinity for the one or more particles; and
(e) applying a mechanical force to the one or more particles.

In some embodiments, the mechanical force is applied by contacting one of a Doctor blade and a brush with the one or more particles. In some embodiments, the mechanical force is applied by ultrasonics, megasonics, electrostatics, or magnetics means.

In some embodiments, the method comprises harvesting or collecting the particles. In some embodiments, the harvesting or collecting of the particles comprises a process selected from the group consisting of scraping with a doctor blade, a brushing process, a dissolution process, an ultrasound process, a megasonics process, an electrostatic process, and a magnetic process.

In some embodiments, the presently disclosed subject matter describes a particle or plurality of particles formed by the methods described herein. In some embodiments, the plurality of particles comprises a plurality of monodisperse particles. In some embodiments, the particle or plurality of particles is selected from the group consisting of a semiconductor device, a crystal, a drug delivery vector, a gene delivery vector, a disease detecting device, a disease locating device, a photovoltaic device, a porogen, a cosmetic, an electret, an additive, a catalyst, a sensor, a detoxifying agent, an abrasive, such as a CMP, a micro-electro-mechanical system (MEMS), a cellular scaffold, a taggant, a pharmaceutical agent, and a biomarker. In some embodiments, the particle or plurality of particles comprise a freestanding structure.

Further, in some embodiments, the presently disclosed subject matter describes a method of fabricating isolated liquid objects, the method comprising (a) contacting a liquid material with the surface of a first low surface energy material; (b) contacting the surface of a second low surface energy material with the liquid, wherein at least one of the surfaces of either the first or second low surface energy material is patterned; (c) sealing the surfaces of the first and the second low surface energy materials together; and (d) separating the two low surface energy materials to produce a replica pattern comprising liquid droplets.

In some embodiments, the liquid material comprises poly (ethylene glycol)-diacrylate. In some embodiments, the low surface energy material comprises perfluoropolyether-diacrylate. In some embodiments, a chemical process is used to seal the surfaces of the first and the second low surface energy materials. In some embodiments, a physical process is used to seal the surfaces of the first and the second low surface energy materials. In some embodiments, one of the surfaces of the low surface energy material is patterned. In some embodiments, one of the surfaces of the low surface energy material is not patterned.

In some embodiments, the method further comprises using the replica pattern composed of liquid droplets to fabricate other objects. In some embodiments, the replica pattern of liquid droplets is formed on the surface of the low surface energy material that is not patterned. In some embodiments, the liquid droplets undergo direct or partial solidification. In some embodiments, the liquid droplets undergo a chemical transformation. In some embodiments, the solidification of the liquid droplets or the chemical transformation of the liquid droplets produce freestanding objects. In some embodiments, the freestanding objects are harvested. In some embodiments, the freestanding objects are bonded in place. In some embodiments, the freestanding objects are directly solidified, partially solidified, or chemically transformed.

In some embodiments, the liquid droplets are directly solidified, partially solidified, or chemically transformed on or in the patterned template to produce objects embedded in the recesses of the patterned template. In some embodiments, the embedded objects are harvested. In some embodiments, the embedded objects are bonded in place. In some embodiments, the embedded objects are used in other fabrication processes.

In some embodiments, the replica pattern of liquid droplets is transferred to other surfaces. In some embodiments, the transfer takes place before the solidification or chemical transformation process. In some embodiments, the transfer takes place after the solidification or chemical transformation process. In some embodiments, the surface to which the replica pattern of liquid droplets is transferred is selected from the group consisting of a non-low surface energy surface, a low surface energy surface, a functionalized surface, and a sacrificial surface. In some embodiments, the method produces a pattern on a surface that is essentially free of one or more scum layers. In some embodiments, the method is used to fabricate semiconductors and other electronic and photonic devices or arrays. In some embodiments, the method is used to create freestanding objects. In some embodiments, the method is used to create three-dimensional objects using multiple patterning steps. In some embodiments, the isolated or patterned object comprises materials selected from the group consisting of organic, inorganic, polymeric, and biological materials. In some embodiments, a surface adhesive agent is used to anchor the isolated structures on a surface.

In some embodiments, the liquid droplet arrays or solid arrays on patterned or non-patterned surfaces are used as regiospecific delivery devices or reaction vessels for additional chemical processing steps. In some embodiments, the additional chemical processing steps are selected from the group consisting of printing of organic, inorganic, polymeric, biological, and catalytic systems onto surfaces; synthesis of organic, inorganic, polymeric, biological materials; and other applications in which localized delivery of materials to surfaces is desired. Applications of the presently disclosed subject matter include, but are not limited to, micro and nanoscale patterning or printing of materials. In some embodiments, the materials to be patterned or printed are selected from the group consisting of surface-binding molecules, inorganic compounds, organic compounds, polymers, biological molecules, nanoparticles, viruses, biological arrays, and the like.

In some embodiments, the applications of the presently disclosed subject matter include, but are not limited to, the synthesis of polymer brushes, catalyst patterning for CVD carbon nanotube growth, cell scaffold fabrication, the application of patterned sacrificial layers, such as etch resists, and the combinatorial fabrication of organic, inorganic, polymeric, and biological arrays.

In some embodiments, non-wetting imprint lithography, and related techniques, are combined with methods to control the location and orientation of chemical components within an individual object. In some embodiments, such methods improve the performance of an object by rationally structuring the object so that it is optimized for a particular application. In some embodiments, the method comprises incorporating biological targeting agents into particles for drug delivery, vaccination, and other applications. In some embodiments, the method comprises designing the particles to include a specific biological recognition motif. In some embodiments, the biological recognition motif comprises biotin/avidin and/or other proteins.

In some embodiments, the method comprises tailoring the chemical composition of these materials and controlling the reaction conditions, whereby it is then possible to organize the biorecognition motifs so that the efficacy of the particle is optimized. In some embodiments, the particles are designed and synthesized so that recognition elements are located on the surface of the particle in such a way to be accessible to cellular binding sites, wherein the core of the particle is preserved to contain bioactive agents, such as therapeutic molecules. In some embodiments, a non-wetting imprint lithography method is used to fabricate the objects, wherein the objects are optimized for a particular application by incorporating functional motifs, such as biorecognition agents, into the object composition. In some embodiments, the method further comprises controlling the microscale and nanoscale structure of the object by using methods selected from the group consisting of self-assembly, stepwise fabrication procedures, reaction conditions, chemical composition, crosslinking, branching, hydrogen bonding, ionic interactions, covalent interactions, and the like. In some embodiments, the method further comprises controlling the microscale and nanoscale structure of the object by incorporating chemically organized precursors into the object. In some embodiments, the chemically organized precursors are selected from the group consisting of block copolymers and core-shell structures.

In sum, the presently disclosed subject matter describes a non-wetting imprint lithography technique that is scalable and offers a simple, direct route to such particles without the use of self-assembled, difficult to fabricate block copolymers and other systems.

III. Formation of Rounded Particles Through "Liquid Reduction"

Referring now to FIGS. 3A through 3F, the presently disclosed subject matter provides a "liquid reduction" process for forming particles that have shapes that are not conformal to the shape of the template, including but not limited to spherical micro- and nanoparticles. For example, a "cube-shaped" template can allow for sphereical particles to be made, whereas a "Block arrow-shaped" template can allow for "lolli-pop" shaped particles or objects to be made wherein the introduction of a gas allows surface tension forces to reshape the resident liquid prior to treating it. While not wishing to be bound by any particular theory, the non-wetting characteristics that can be provided in some embodiments of the presently disclosed patterned template and/or treated or coated substrate allows for the generation of rounded, e.g., spherical, particles.

Figure 3A:
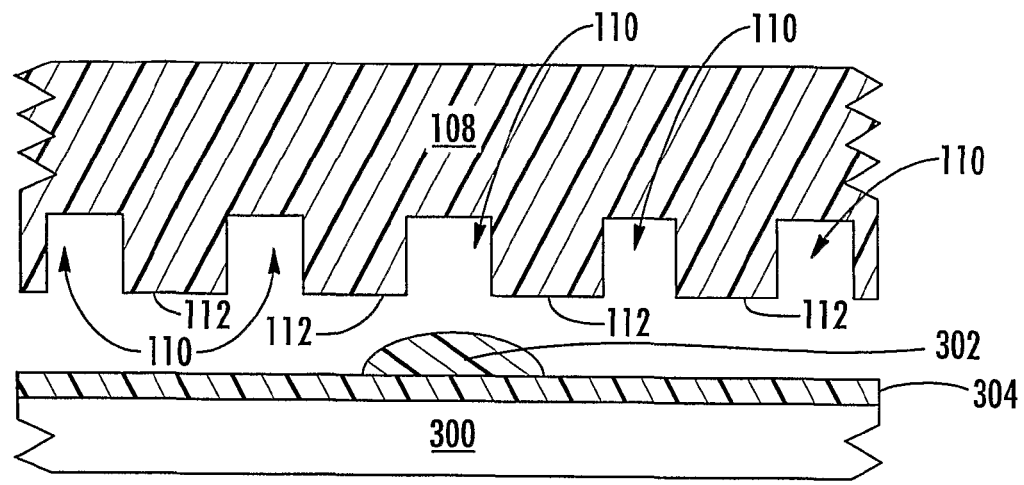
FIGS. 3A-3F are a schematic representation of the presently disclosed method for preparing one or more spherical particles.

Referring now to FIG. 3A, droplet 302 of a liquid material is disposed on substrate 300, which in some embodiments is coated or treated with a non-wetting material 304. A patterned template 108, which comprises a plurality of recessed areas 110 and patterned surface areas 112, also is provided.

Figure 3B:
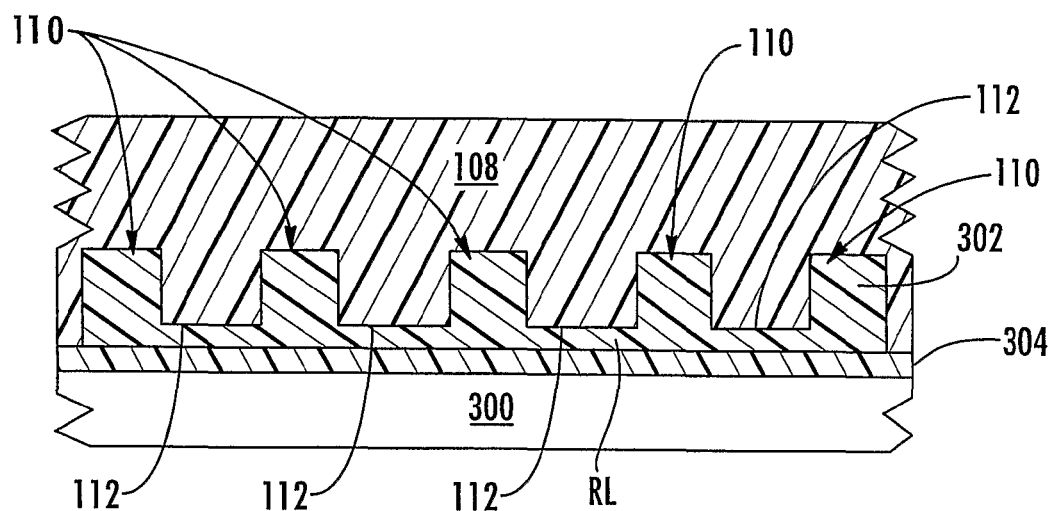

Referring now to FIG. 3B, patterned template 108 is contacted with droplet 302. The liquid material comprising droplet 302 then enters recessed areas 110 of patterned template 108. In some embodiments, a residual, or "scum," layer RL of the liquid material comprising droplet 302 remains between the patterned template 108 and substrate 300.

Figure 3C:
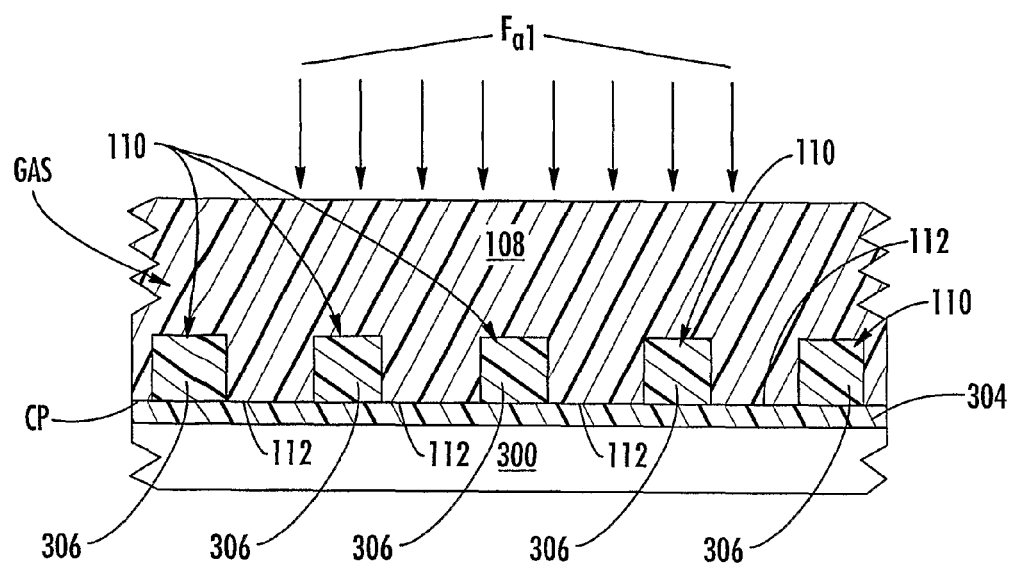

Referring now to FIG. 3C, a first force $F_{a1}$ is applied to patterned template 108. A contact point CP is formed between the patterned template 108 and the substrate and displacing residual layer RL. Particles 306 are formed in the recessed areas 110 of patterned template 108.

Figure 3D:
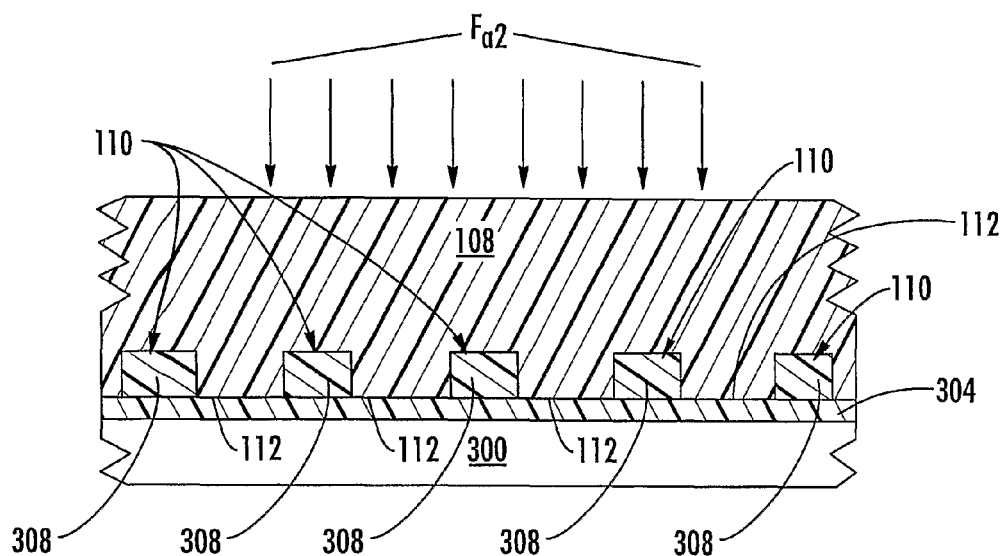

Referring now to FIG. 3D, a second force $F_{a2}$, wherein the force applied by $F_{a2}$ is greater than the force applied by $F_{a1}$, is then applied to patterned template 108, thereby forming smaller liquid particles 308 inside recessed areas 112 and forcing a portion of the liquid material comprising droplet 302 out of recessed areas 112.

Figure 3E:
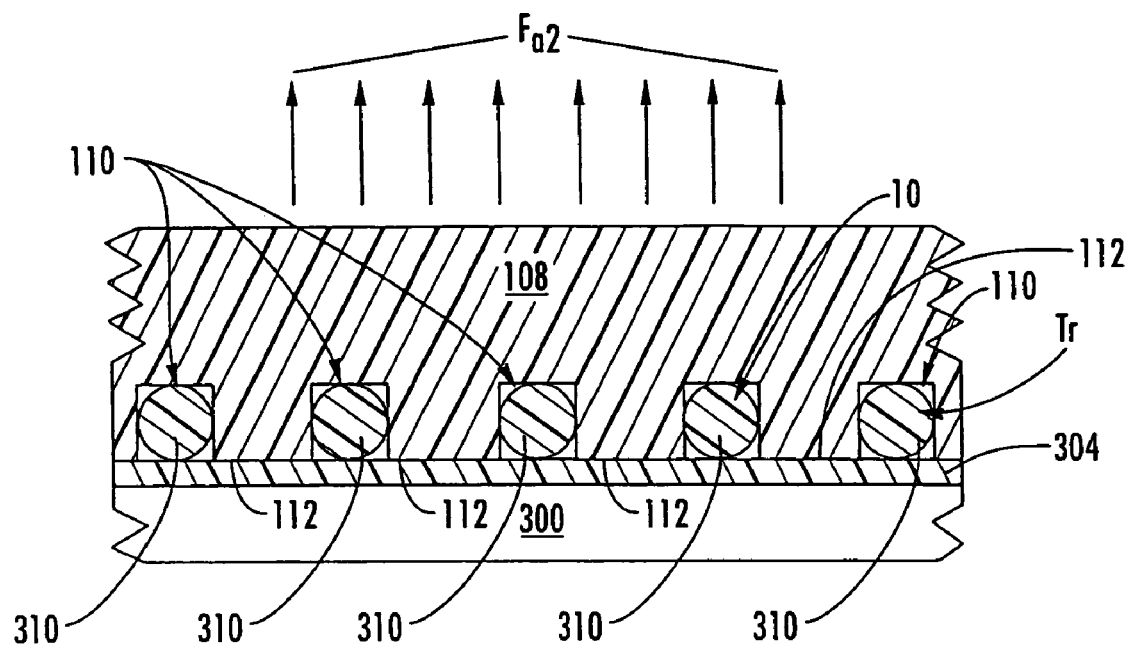

Referring now to FIG. 3E, the second force $F_{a2}$ is released, thereby returning the contact pressure to the original contact pressure applied by first force $F_{a1}$. In some embodiments, patterned template 108 comprises a gas permeable material, which allows a portion of space with recessed areas 112 to be filled with a gas, such as nitrogen, thereby forming a plurality of liquid spherical droplets 310. Once this liquid reduction is achieved, the plurality of liquid spherical droplets 310 are treated by a treating process $T_r$.

Figure 3F:
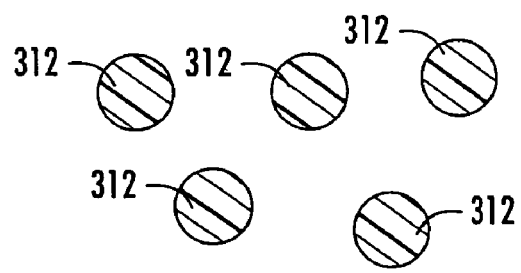

Referring now to FIG. 3F, treated liquid spherical droplets 310 are released from patterned template 108 to provide a plurality of freestanding spherical particles 312.

IV. Formation of Polymeric Nano- to Micro-Electrets

Figure 4A:
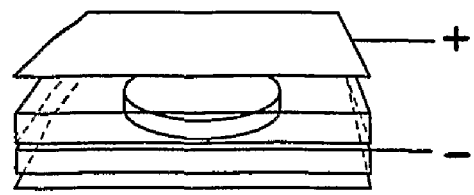
FIGS. 4A-4D are a schematic representation of the presently disclosed method for fabricating charged polymeric particles.
Figure 4B:
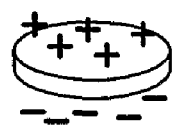
Figure 4C:
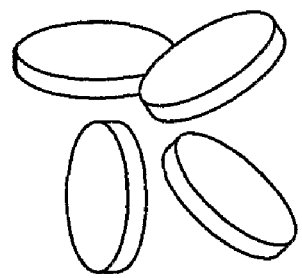
Figure 4D:
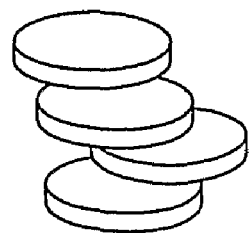

Referring now to FIGS. 4A and 4B, in some embodiments, the presently disclosed subject matter describes a method for preparing polymeric nano- to micro-electrets by applying an electric field during the polymerization and/or crystallization step during molding (FIG. 4A) to yield a charged polymeric particle (FIG. 4B). In some embodiments, the charged polymeric particles spontaneously aggregate into chain-like structures (FIG. 4D) instead of the random configurations shown in FIG. 4C.

In some embodiments, the charged polymeric particle comprises a polymeric electret. In some embodiments, the polymeric electret comprises a polymeric nano-electret. In some embodiments, the charged polymeric particles aggregate into chain-like structures. In some embodiments, the charged polymeric particles comprise an additive for an electro-rheological device. In some embodiments, the electro-rheological device is selected from the group consisting of clutches and active dampening devices. In some embodiments, the charged polymeric particles comprise nano-piezoelectric devices. In some embodiments, the nano-piezoelectric devices are selected from the group consisting of actuators, switches, and mechanical sensors.

V. Formation of Multilayer Structures

In some embodiments, the presently disclosed subject matter provides a method for forming multilayer structures, including multilayer particles. In some embodiments, the multilayer structures, including multilayer particles, comprise nanoscale multilayer structures. In some embodiments, multilayer structures are formed by depositing multiple thin layers of immisible liquids and/or solutions onto a substrate and forming particles as described by any of the methods hereinabove. The immiscibility of the liquid can be based on any physical characteristic, including but not limited to density, polarity, and volatility. Examples of possible morphologies of the presently disclosed subject matter are illustrated in FIGS. 5A-5C and include, but are not limited to, multi-phase sandwich structures, core-shell particles, and internal emulsions, microemulsions and/or nano-sized emulsions.

Figure 5A:
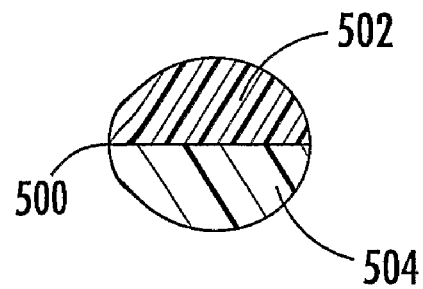
FIGS. 5A-5C are a schematic illustration of multilayer particles that can be formed using the presently disclosed soft lithography method.

Referring now to FIG. 5A, a multi-phase sandwich structure 500 of the presently disclosed subject matter is shown, which by way of example, comprises a first liquid material 502 and a second liquid material 504.

Figure 5B:
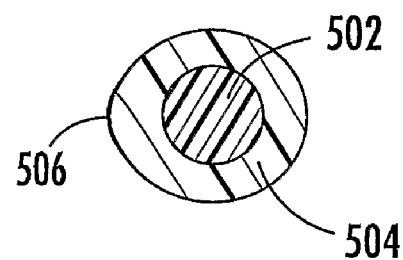

Referring now to FIG. 5B, a core-shell particle 506 of the presently disclosed subject matter is shown, which by way of example, comprises a first liquid material 502 and a second liquid material 504.

Figure 5C:
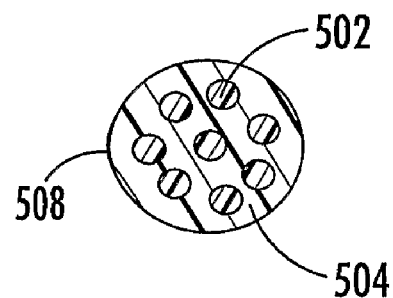

Referring now to FIG. 5C, an internal emulsion particle 508 of the presently disclosed subject matter is shown, which by way of example, comprises a first liquid material 502 and a second liquid material 504.

More particularly, in some embodiments, the method comprises disposing a plurality of immiscible liquids between the patterned template and substrate to form a multilayer structure, e.g., a multilayer nanostructure. In some embodiments, the multilayer structure comprises a multilayer particle. In some embodiments, the multilayer structure comprises a structure selected from the group consisting of multi-phase sandwich structures, core-shell particles, internal emulsions, microemulsions, and nanosized emulsions.

VI. Fabrication of Complex Multi-Dimensional Structures

In some embodiments, the currently disclosed subject matter provides a process for fabricating complex, multi-dimensional structures. In some embodiments, complex multi-dimensional structures can be formed by performing the steps illustrated in FIGS. 2A-2E. In some embodiments, the method comprises imprinting onto a patterned template that is aligned with a second patterned template (instead of imprinting onto a smooth substrate) to generate isolated multi-dimensional structures that are cured and released as described herein. A schematic illustration of an embodiment of a process for forming complex multi-dimensional structures and examples of such structures are provided in FIGS. 6A-6C.

Figure 6A:
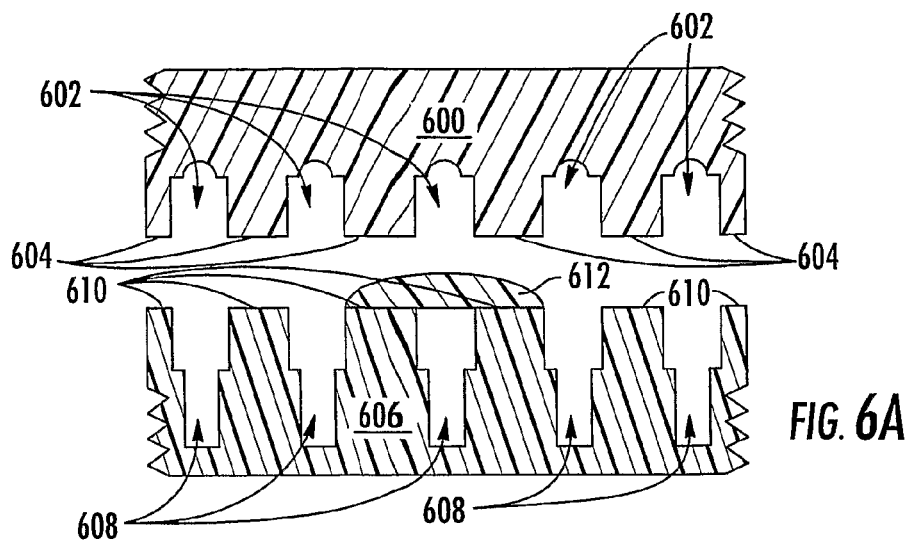
FIGS. 6A-6C are a schematic representation of the presently disclosed method for making three-dimensional nano-structures using a soft lithography technique.

Referring now to FIG. 6A, a first patterned template 600 is provided. First patterned template 600 comprises a plurality of recessed areas 602 and a plurality of non-recessed surfaces 604. Also provided is a second patterned template 606. Second patterned template 606 comprises a plurality of recessed areas 608 and a plurality of non-recessed surfaces 610. As shown in FIG. 6A, first patterned template 600 and second patterned template 606 are aligned in a predetermined spaced relationship. A droplet of liquid material 612 is disposed between first patterned template 600 and second patterned template 606.

Figure 6B:
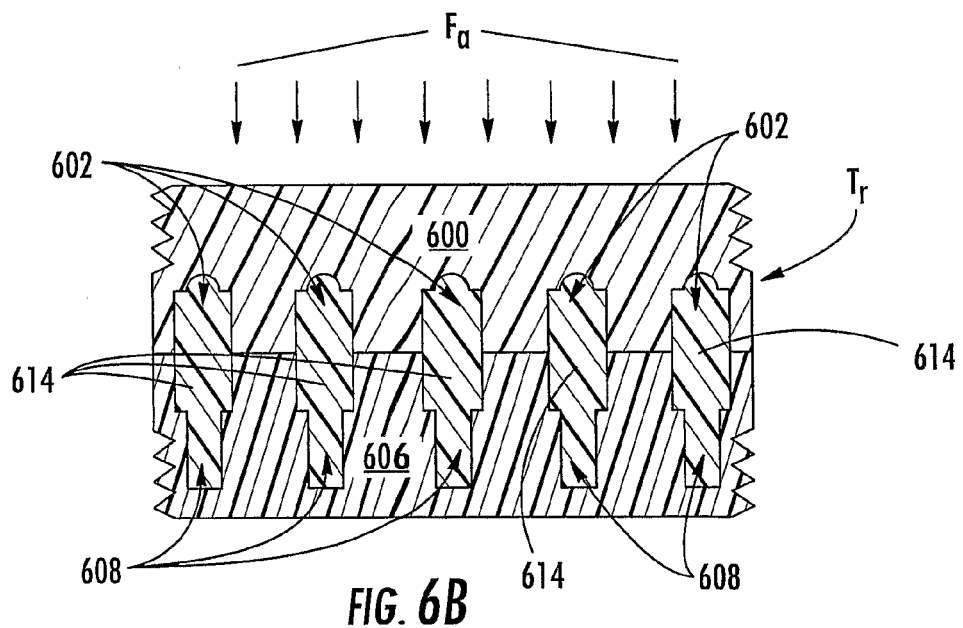

Referring now to FIG. 6B, patterned template 600 is contacted with patterned template 606. A force $F_a$ is applied to patterned template 600 causing the liquid material comprising droplet 612 to migrate to the plurality of recessed areas 602 and 608. The liquid material comprising droplet 612 is then treated by treating process $T_r$ to form a patterned, treated liquid material 614.

Figure 6C:
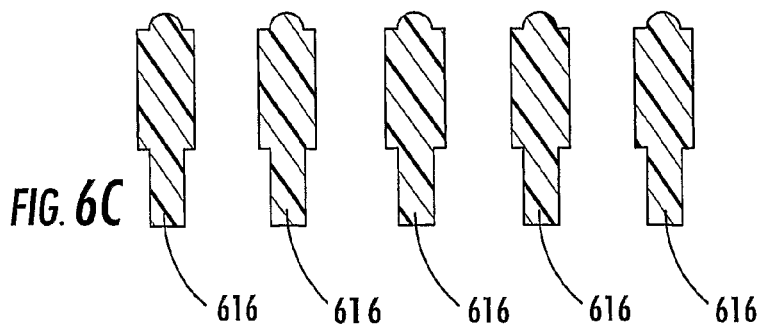

Referring now to FIG. 6C, the patterned, treated liquid material 614 of FIG. 6B is released by any of the releasing methods described herein to provide a plurality of multi-dimensional patterned structures 616.

In some embodiments, patterned structure 616 comprises a nanoscale-patterned structure. In some embodiments, patterned structure 616 comprises a multi-dimensional structure. In some embodiments, the multi-dimensional structure comprises a nanoscale multi-dimensional structure. In some embodiments, the multi-dimensional structure comprises a plurality of structural features. In some embodiments, the structural features comprise a plurality of heights.

In some embodiments, a microelectronic device comprising patterned structure 616 is provided. Indeed, patterned structure 616 can be any structure imaginable, including "dual damscene" structures for microelectronics. In some embodiments, the microelectronic device is selected from the group consisting of integrated circuits, semiconductor particles, quantum dots, and dual damascene structures. In some embodiments, the microelectronic device exhibits certain physical properties selected from the group consisting of etch resistance, low dielectric constant, high dielectric constant, conducting, semiconducting, insulating, porosity, and non-porosity.

In some embodiments, the presently disclosed subject matter discloses a method of preparing a multidimensional, complex structure. Referring now to FIGS. 7A-7F, in some embodiments, a first patterned template 700 is provided. First patterned template 700 comprises a plurality of non-recessed surface areas 702 and a plurality of recessed surface areas 704. Continuing particularly with FIG. 7A, also provided is a substrate 706. In some embodiments, substrate 706 is coated with a non-wetting agent 708. A droplet of a first liquid material 710 is disposed on substrate 706.

Figure 7A:
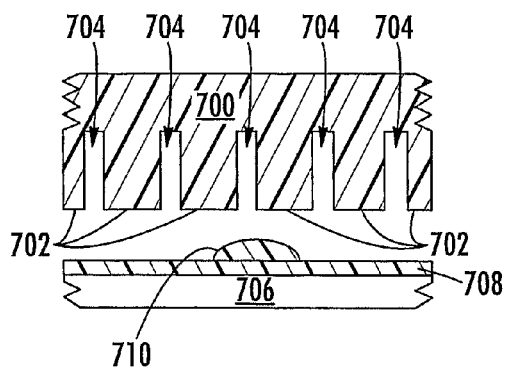
FIGS. 7A-7F are a schematic representation of an embodiment of the presently disclosed method for preparing a multidimensional complex structure.
Figure 7B:
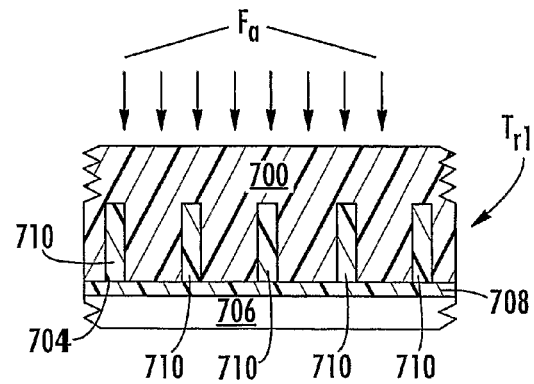
Figure 7C:
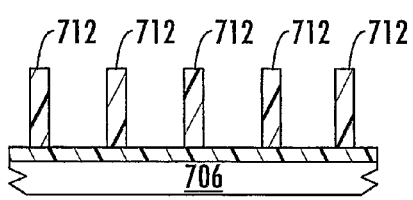

Referring now to FIGS. 7B and 7C, first patterned template 700 is contacted with substrate 706. A force $F_a$ is applied to first patterned template 700 such that the droplet of the first liquid material 710 is forced into recesses 704. The liquid material comprising the droplet of first liquid material 710 is treated by a first treating process $T_{r1}$ to form a treated first liquid material within the plurality of recesses 704. In some embodiments, first treating process $T_{r1}$ comprises a partial curing process causing the treated first liquid material to adhere to substrate 706. Referring particularly to FIG. 7C, first patterned template 700 is removed to provide a plurality of structural features 712 on substrate 706.

Figure 7D:
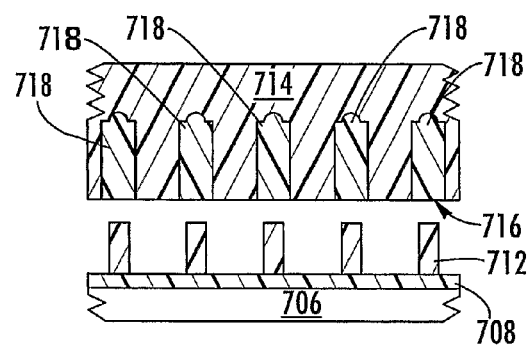
Figure 7E:
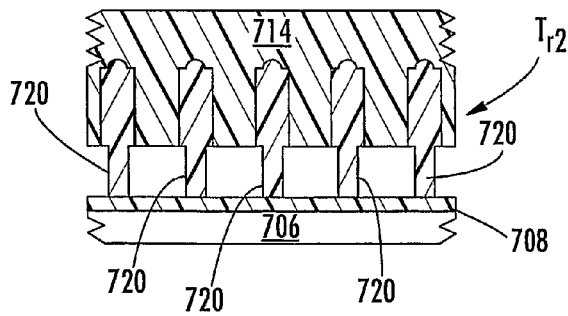
Figure 7F:
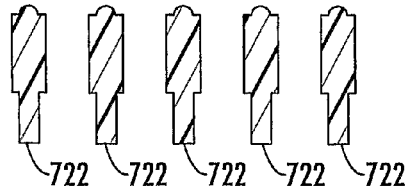

Referring now to FIGS. 7D-7F, a second patterned template 714 is provided. Second patterned substrate 714 comprises a plurality of recesses 716, which are filled with a second liquid material 718. The filling of recesses 716 can be accomplished in a manner similar to that described in FIGS. 7A and 7B with respect to recesses 704. Referring particularly to FIG. 7E, second patterned template 714 is contacted with structural features 712. Second liquid material 718 is treated with a second treating process $T_{r2}$ such that the second liquid material 718 adheres to the plurality of structural feature 712, thereby forming a multidimensional structure 720. Referring particularly to FIG. 7F, second patterned template 714 and substrate 706 are removed, providing a plurality of free standing multidimensional structures 722. In some embodiments, the process schematically presented in FIGS. 7A-7F can be carried out multiple times as desired to form intricate nanostructures.

Accordingly, in some embodiments, a method for forming multidimensional structures is provided, the method comprising:

(a) providing a particle prepared by the process described in the figures;

(b) providing a second patterned template;

(c) disposing a second liquid material in the second patterned template;

(d) contacting the second patterned template with the particle of step (a); and (e) treating the second liquid material to form a multidimensional structure.

VII. Imprint Lithography

Referring now to FIGS. 8A-8D, a method for forming a pattern on a substrate is illustrated. In the embodiment illustrated in FIG. 8, an imprint lithography technique is used to form a pattern on a substrate.

Figure 8A:
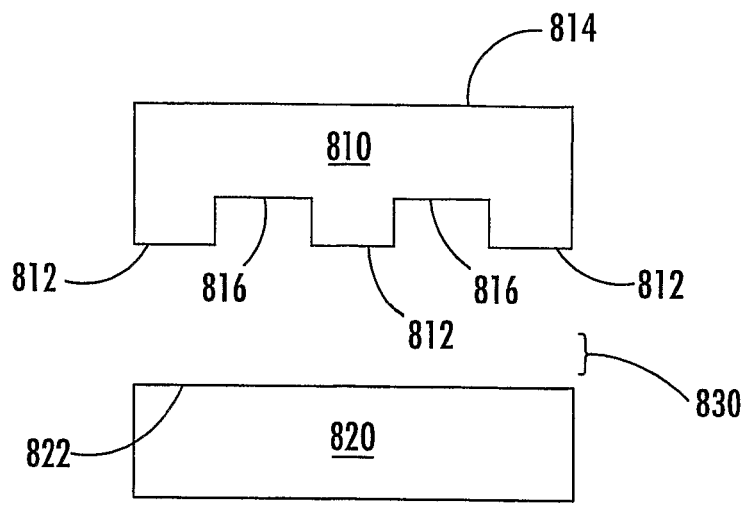
FIGS. 8A-8E are a schematic representation of the presently disclosed imprint lithography process resulting in a "scum layer."

Referring now to FIG. 8A, a patterned template 810 is provided. In some embodiments, patterned template 810 comprises a solvent resistant, low surface energy polymeric material, derived from casting low viscosity liquid materials onto a master template and then curing the low viscosity liquid materials to generate a patterned template as defined hereinabove. Patterned template 810 further comprises a first patterned template surface 812 and a second template surface 814. The first patterned template surface 812 further comprises a plurality of recesses 816. The patterned template derived from a solvent resistant, low surface energy polymeric material could be mounted on another material to facilitate alignment of the patterned template or to facilitate continuous processing such as a conveyor belt. This might be particularly useful in the fabrication of precisely placed structures on a surface, such as in the fabrication of a complex devices or a semiconductor, electronic or photonic devices.

Referring again to FIG. 8A, a substrate 820 is provided. Substrate 820 comprises a substrate surface 822. In some embodiments, substrate 820 is selected from the group consisting of a polymer material, an inorganic material, a silicon material, a quartz material, a glass material, and surface treated variants thereof. In some embodiments, at least one of patterned template 810 and substrate 820 has a surface energy lower than 18 mN/m. In some embodiments, at least one of patterned template 810 and substrate 820 has a surface energy lower than 15 mN/m.

In some embodiments, as illustrated in FIG. 8A, patterned template 810 and substrate 820 are positioned in a spaced relationship to each other such that first patterned template surface 812 faces substrate surface 822 and a gap 830 is created between first patterned template surface 812 and substrate surface 822. This is an example of a predetermined relationship.

Figure 8B:
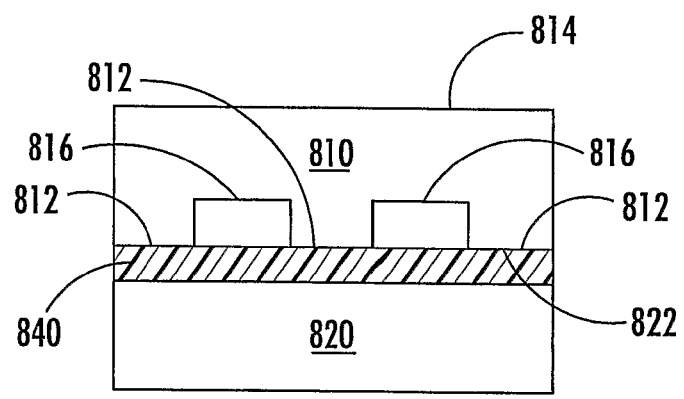

Referring now to FIG. 8B, a volume of liquid material 840 is disposed in the gap 830 between first patterned template surface 812 and substrate surface 822. In some embodiments, the volume of liquid material 840 is disposed directed on a non-wetting agent (not shown), which is disposed on first patterned template surface 812.

Figure 8C:
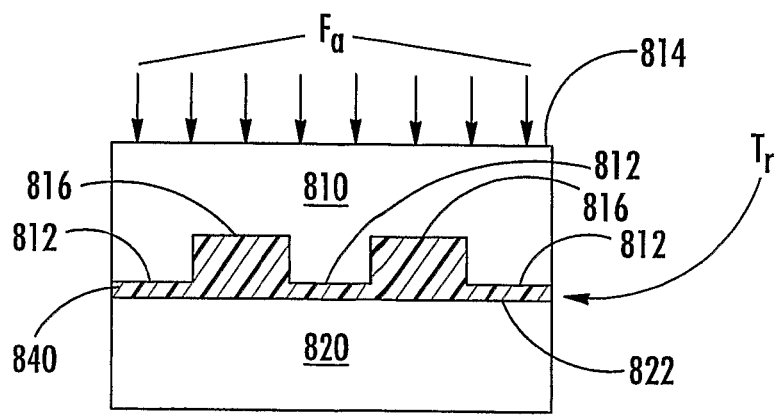

Referring now to FIG. 8C, in some embodiments, first patterned template 812 is contacted with the volume of liquid material 840. A force $F_a$ is applied to second template surface 814 thereby forcing the volume of liquid material 840 into the plurality of recesses 816. In some embodiments, as illustrated in FIG. 8C, a portion of the volume of liquid material 840 remains between first patterned template surface 812 and substrate surface 820 after force $F_a$ is applied.

Referring again to FIG. 8C, in some embodiments, the volume of liquid material 840 is treated by a treating process $T_r$, while force $F_a$ is being applied to form a treated liquid material 842. In some embodiments, treating process $T_r$ comprises a process selected from the group consisting of a thermal process, a photochemical process, and a chemical process.

Figure 8D:
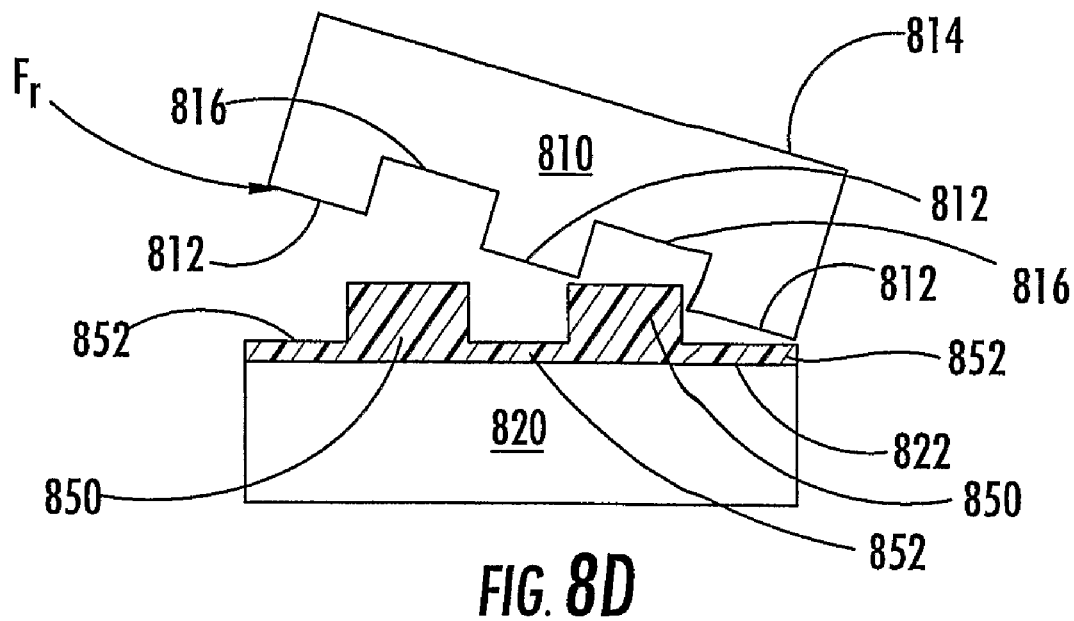
Figure 8E:
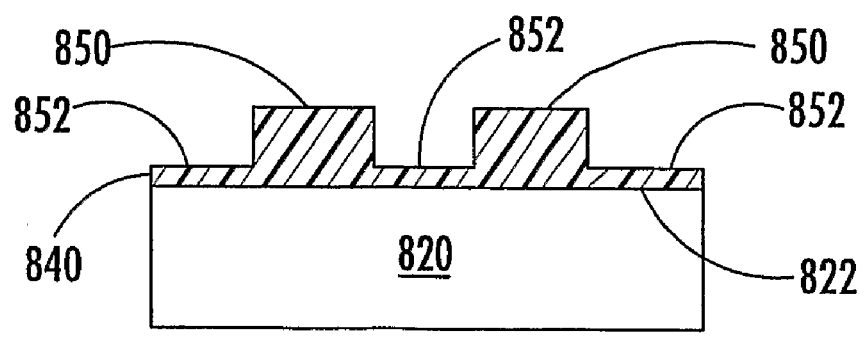

Referring now to FIG. 8D, a force $F_r$ is applied to patterned template 810 to remove patterned template 810 from treated liquid material 842 to reveal a pattern 850 on substrate 820 as shown in FIG. 8E. In some embodiments, a residual, or "scum," layer 852 of treated liquid material 842 remains on substrate 820.

More particularly, the method for forming a pattern on a substrate comprises:

(a) providing patterned template and a substrate, wherein the patterned template comprises a patterned template surface having a plurality of recessed areas formed therein;

(b) disposing a volume of liquid material in or on at least one of:

(i) the patterned template surface; and (ii) the plurality of recessed areas;

(c) contacting the patterned template surface with the substrate; and (d) treating the liquid material to form a pattern on the substrate.

In some embodiments, the patterned template comprises a solvent resistant, low surface energy polymeric material derived from casting low viscosity liquid materials onto a master template and then curing the low viscosity liquid materials to generate a patterned template. In some embodiments, the patterned template comprises a solvent resistant elastomeric material.

In some embodiments, at least one of the patterned template and substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the perfluoropolyether material comprises a backbone structure selected from the group consisting of:

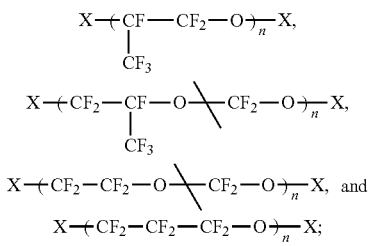

wherein X is present or absent, and when present comprises an endcapping group.

In some embodiments, the fluoroolefin material is selected from the group consisting of:

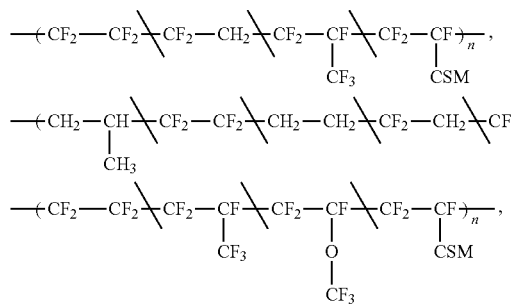

wherein CSM comprises a cure site monomer.

In some embodiments, the fluoroolefin material is made from monomers which comprise tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer.

In some embodiments, the silicone material comprises a fluoroalkyl functionalized polydimethylsiloxane (PDMS) having the following structure:

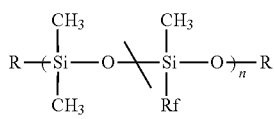

wherein:

R is selected from the group consisting of an acrylate, a methacrylate, and a vinyl group; and Rf comprises a fluoroalkyl chain.

In some embodiments, the styrenic material comprises a fluorinated styrene monomer selected from the group consisting of:

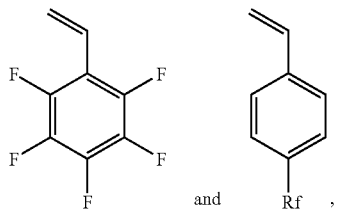

wherein Rf comprises a fluoroalkyl chain.

In some embodiments, the acrylate material comprises a fluorinated acrylate or a fluorinated methacrylate having the following structure:

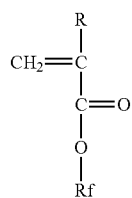

wherein:

R is selected from the group consisting of H, alkyl, substituted alkyl, aryl, and substituted aryl; and Rf comprises a fluoroalkyl chain.

In some embodiments, the triazine fluoropolymer comprises a fluorinated monomer.

In some embodiments, the fluorinated monomer or fluorinated oligomer that can be polymerized or crosslinked by a metathesis polymerization reaction comprises a functionalized olefin. In some embodiments, the functionalized olefin comprises a functionalized cyclic olefin.

In some embodiments, at least one of the patterned template and the substrate has a surface energy lower than 18 mN/m. In some embodiments, at least one of the patterned template and the substrate has a surface energy lower than 15 mN/m.

In some embodiments, the substrate is selected from the group consisting of a polymer material, an inorganic material, a silicon material, a quartz material, a glass material, and surface treated variants thereof. In some embodiments, the substrate is selected from one of an electronic device in the process of being manufactured and a photonic device in the process of being manufactured. In some embodiments, the substrate comprises a patterned area.

In some embodiments, the plurality of recessed areas comprises a plurality of cavities. In some embodiments, the plurality of cavities comprise a plurality of structural features. In some embodiments, the plurality of structural features has a dimension ranging from about 10 microns to about 1 nanometer in size. In some embodiments, the plurality of structural features has a dimension ranging from about 10 microns to about 1 micron in size. In some embodiments, the plurality of structural features has a dimension ranging from about 1 micron to about 100 nm in size. In some embodiments, the plurality of structural features has a dimension ranging from about 100 nm to about 1 nm in size.

In some embodiments, the liquid material is selected from the group consisting of a polymer, a solution, a monomer, a plurality of monomers, a polymerization initiator, a polymerization catalyst, an inorganic precursor, a metal precursor, a pharmaceutical agent, a tag, a magnetic material, a paramagnetic material, a superparamagnetic material, a ligand, a cell penetrating peptide, a porogen, a surfactant, a plurality of immiscible liquids, a solvent, and a charged species. In some embodiments, the pharmaceutical agent is selected from the group consisting of a drug, a peptide, RNAi, and DNA. In some embodiments, the tag is selected from the group consisting of a fluorescence tag, a radiolabeled tag, and a contrast agent. In some embodiments, the ligand comprises a cell targeting peptide.

Represesentative superparamagnetic or paramagnetic materials include but are not limited to $Fe_2O_3$, $Fe_3O_4$, FePt, Co, $MnFe_2O_4$, $CoFe_2O_4$, $CuFe_2O_4$, $NiFe_2O_4$ and ZnS doped with Mn for magneto-optical applications, CdSe for optical applications, and borates for boron neutron capture treatment.

In some embodiments, the liquid material is selected from one of a resist polymer and a low-k dielectric. In some embodiments, the liquid material comprises a non-wetting agent.

In some embodiments, the disposing of the volume of liquid material is regulated by a spreading process. In some embodiments, the spreading process comprises:
(a) disposing a first volume of liquid material on the patterned template to form a layer of liquid material on the patterned template; and
(b) drawing an implement across the layer of liquid material to:
  (i) remove a second volume of liquid material from the layer of liquid material on the patterned template; and
  (ii) leave a third volume of liquid material on the patterned template.

In some embodiments, the contacting of the first template surface with the substrate eliminates essentially all of the disposed volume of liquid material.

In some embodiments, the treating of the liquid material comprises a process selected from the group consisting of a thermal process, a photochemical process, and a chemical process.

In some embodiments, the method comprises a batch process. In some embodiments, the batch process is selected from one of a semi-batch process and a continuous batch process.

In some embodiments, the presently disclosed subject matter describes a patterned substrate formed by the presently disclosed methods.

VIII. Imprint Lithography Free of a Residual "Scum Layer"

A characteristic of imprint lithography that has restrained its full potential is the formation of a "scum layer" once the liquid material, e.g., a resin, is patterned. The "scum layer" comprises residual liquid material that remains between the stamp and the substrate. In some embodiments, the presently disclosed subject matter provides a process for generating patterns essentially free of a scum layer.

Figure 9A:
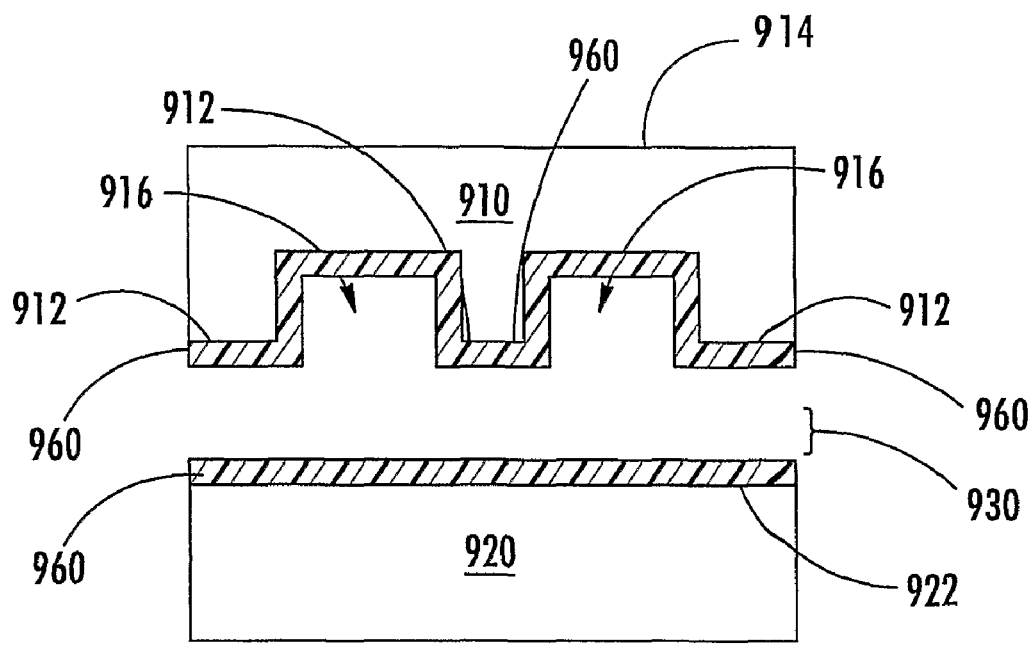
FIGS. 9A-9E are a schematic representation of the presently disclosed imprint lithography method, which eliminates the "scum layer" by using a functionalized, non-wetting patterned template and a non-wetting substrate.

Referring now to FIGS. 9A-9E, in some embodiments, a method for forming a pattern on a substrate is provided, wherein the pattern is essentially free of a scum layer. Referring now to FIG. 9A, a patterned template 910 is provided. Patterned template 910 further comprises a first patterned template surface 912 and a second template surface 914. The first patterned template surface 912 further comprises a plurality of recesses 916. In some embodiments, a non-wetting agent 960 is disposed on the first patterned template surface 912.

Referring again to FIG. 9A, a substrate 920 is provided. Substrate 920 comprises a substrate surface 922: In some embodiments, a non-wetting agent 960 is disposed on substrate surface 920.

In some embodiments, as illustrated in FIG. 9A, patterned template 910 and substrate 920 are positioned in a spaced relationship to each other such that first patterned template surface 912 faces substrate surface 922 and a gap 930 is created between first patterned template surface 912 and substrate surface 922.

Figure 9B:
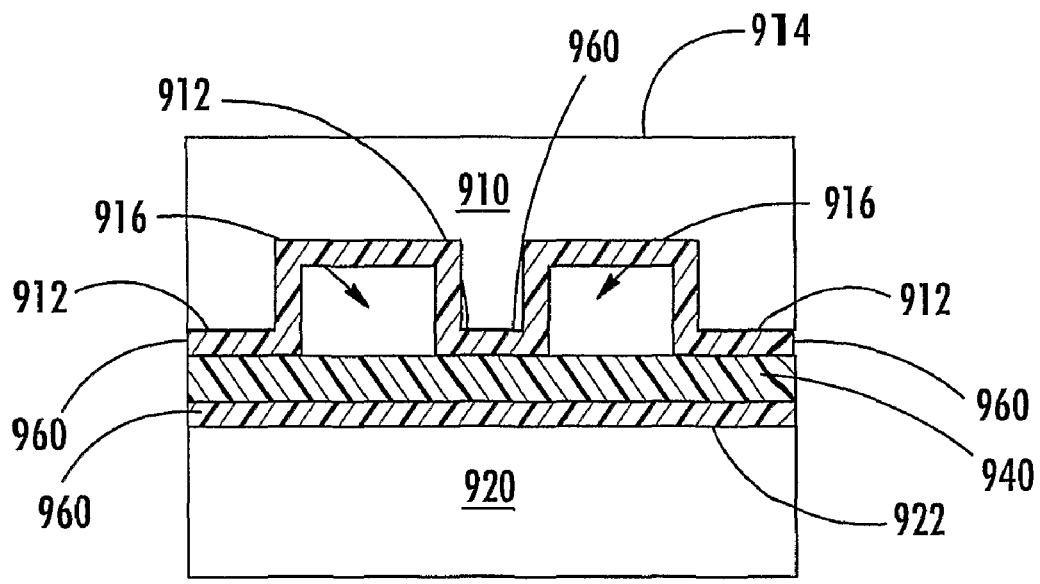

Referring now to FIG. 9B, a volume of liquid material 940 is disposed in the gap 930 between first patterned template surface 912 and substrate surface 922. In some embodiments, the volume of liquid material 940 is disposed directly on first patterned template surface 912. In some embodiments, the volume of liquid material 940 is disposed directly on non-wetting agent 960, which is disposed on first patterned template surface 912. In some embodiments, the volume of liquid material 940 is disposed directly on substrate surface 920. In some embodiments, the volume of liquid material 940 is disposed directly on non-wetting agent 960, which is disposed on substrate surface 920.

Figure 9C:
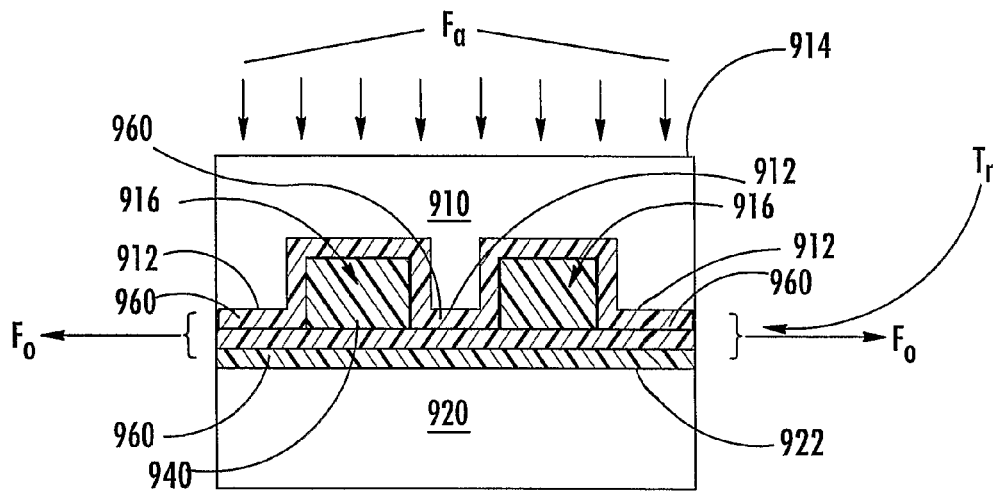

Referring now to FIG. 9C, in some embodiments, first patterned template surface 912 is contacted with the volume of liquid material 940. A force $F_a$ is applied to second template surface 914 thereby forcing the volume of liquid material 940 into the plurality of recesses 916. In contrast with the embodiment illustrated in FIG. 8, a portion of the volume of liquid material 940 is forced out of gap 930 by force $F_o$ when force $F_a$ is applied.

Referring again to FIG. 9C, in some embodiments, the volume of liquid material 940 is treated by a treating process $T_r$ while force $F_a$ is being applied to form a treated liquid material 942.

Figure 9D:
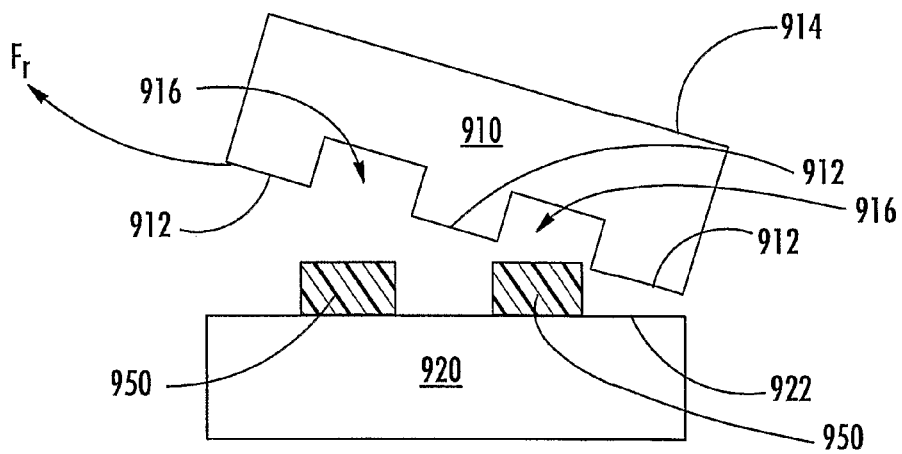
Figure 9E:
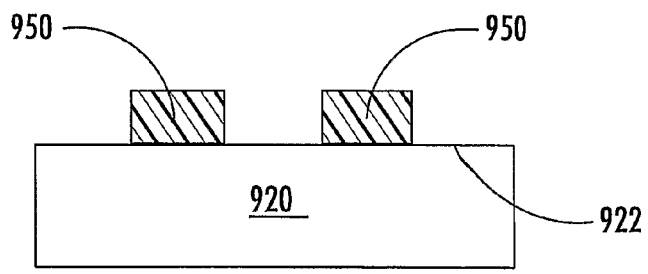

Referring now to FIG. 9D, a force $F_r$ is applied to patterned template 910 to remove patterned template 910 from treated liquid material 942 to reveal a pattern 950 on substrate 920 as shown in FIG. 9E. In this embodiment, substrate 920 is essentially free of a residual, or "scum," layer of treated liquid material 942.

In some embodiments, at least one of the template surface and substrate comprises a functionalized surface element. In some embodiments, the functionalized surface element is functionalized with a non-wetting material. In some embodiments, the non-wetting material comprises functional groups that bind to the liquid material. In some embodiments, the non-wetting material is selected from the group consisting of a trichloro silane, a trialkoxy silane, a trichloro silane comprising non-wetting and reactive functional groups, a trialkoxy silane comprising non-wetting and reactive functional groups, and mixtures thereof.

In some embodiments, the point of contact between the two surface elements is free of liquid material. In some embodiments, the point of contact between the two surface elements comprises residual liquid material. In some embodiments, the height of the residual liquid material is less than 30% of the height of the structure. In some embodiments, the height of the residual liquid material is less than 20% of the height of the structure. In some embodiments, the height of the residual liquid material is less than 10% of the height of the structure. In some embodiments, the height of the residual liquid material is less than 5% of the height of the structure. In some embodiments, the volume of liquid material is less than the volume of the patterned template. In some embodiments, substantially all of the volume of liquid material is confined to the patterned template of at least one of the surface elements. In some embodiments, having the point of contact between the two surface elements free of liquid material retards slippage between the two surface elements.

IX. Solvent-Assisted Micro-Moldina (SAMIM)

In some embodiments, the presently disclosed subject matter describes a solvent-assisted micro-molding (SAMIM) method for forming a pattern on a substrate.

Figure 10A:
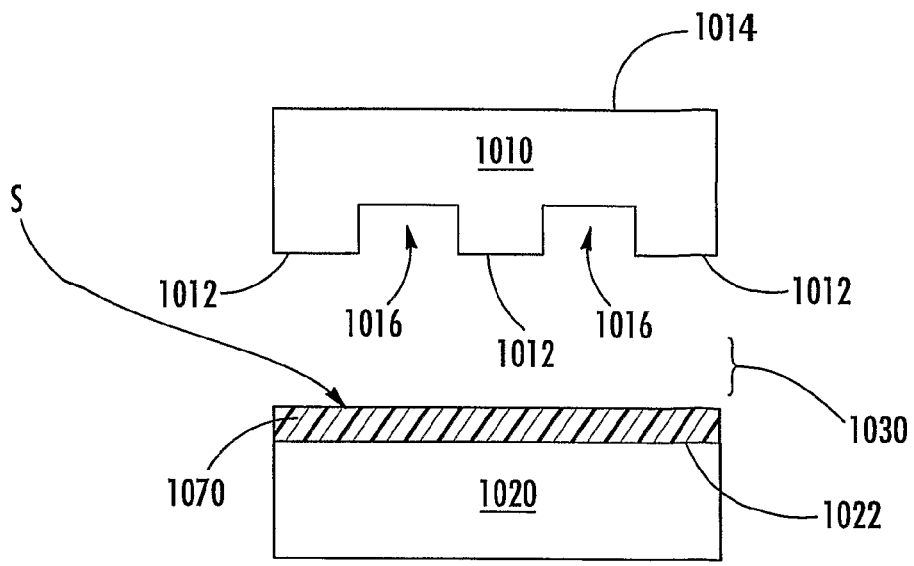
FIGS. 10A-10E are a schematic representation of the presently disclosed solvent-assisted micro-molding (SAMIM) method for forming a pattern on a substrate.

Referring now to FIG. 10A, a patterned template 1010 is provided. Patterned template 1010 further comprises a first patterned template surface 1012 and a second template surface 1014. The first patterned template surface 1012 further comprises a plurality of recesses 1016.

Referring again to FIG. 10A, a substrate 1020 is provided. Substrate 1020 comprises a substrate surface 1022. In some embodiments, a polymeric material 1070 is disposed on substrate surface 1022. In some embodiments, polymeric material 1070 comprises a resist polymer.

Referring again to FIG. 10A, patterned template 1010 and substrate 1020 are positioned in a spaced relationship to each other such that first patterned template surface 1012 faces substrate surface 1022 and a gap 1030 is created between first patterned template surface 1012 and substrate surface 1022. As shown in FIG. 10A, a solvent S is disposed within gap 1030, such that solvent S contacts polymeric material 1070 forming a swollen polymeric material 1072.

Figure 10B:
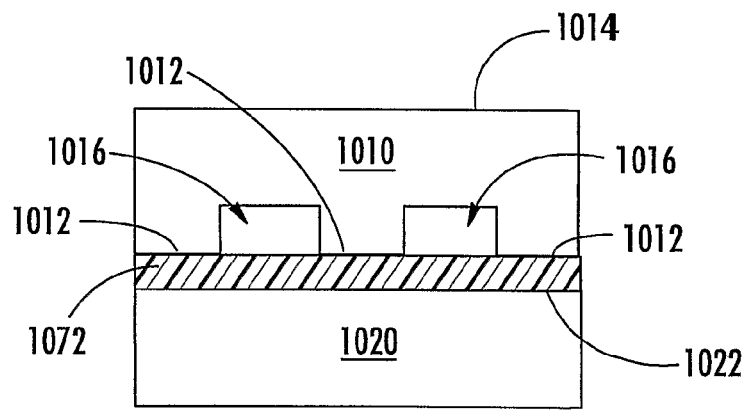
Figure 10C:
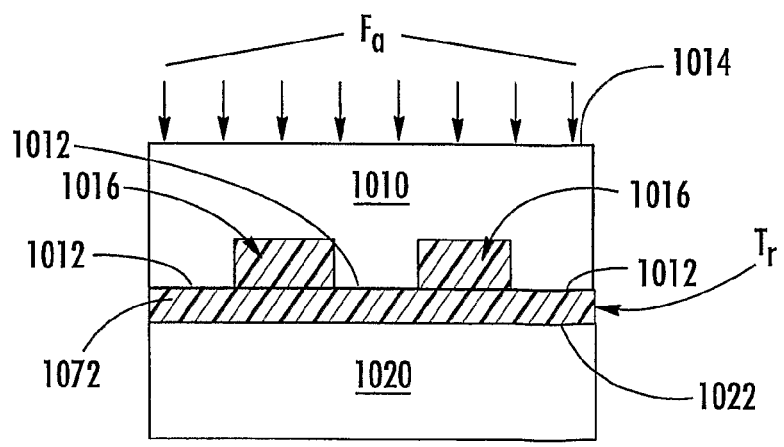

Referring now to FIGS. 10B and 10C, first patterned template surface 1012 is contacted with swollen polymeric material 1072. A force $F_a$ is applied to second template surface 1014 thereby forcing a portion of swollen polymeric material 1072 into the plurality of recesses 1016 and leaving a portion of swollen polymeric material 1072 between first patterned template surface 1012 and substrate surface 1020. The swollen polymeric material 1072 is then treated by a treating process $T_r$, while under pressure.

Figure 10D:
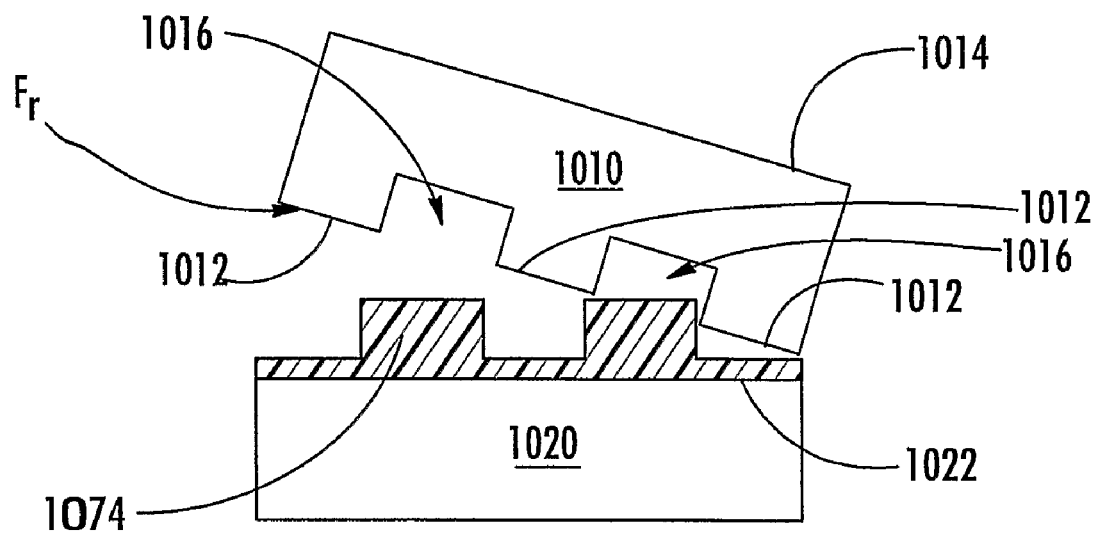
Figure 10E:
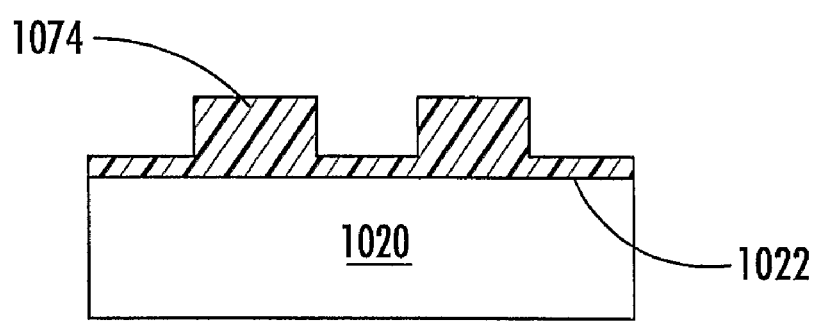

Referring now to FIG. 10D, a force $F_r$ is applied to patterned template 1010 to remove patterned template 1010 from treated swollen polymeric material 1072 to reveal a polymeric pattern 1074 on substrate 1020 as shown in FIG. 10E.

X. Removing the Patterned Structure from the Patterned Template and/or Substrate In some embodiments, the patterned structure (e.g., a patterned micro- or nanostructure) is removed from at least one of the patterned template and/or the substrate. This can be accomplished by a number of approaches, including but not limited to applying the surface element containing the patterned structure to a surface that has an affinity for the patterned structure; deforming the surface element containing the patterned structure such that the patterned structure is released from the surface element; swelling the surface element containing the patterned structure with a first solvent to extrude the patterned structure; and washing the surface element containing the patterned structure with a second solvent that has an affinity for the patterned structure.

In some embodiments, the first solvent comprises supercritical fluid carbon dioxide. In some embodiments, the first solvent comprises water. In some embodiments, the first solvent comprises an aqueous solution comprising water and a detergent. In embodiments, the deforming the surface element is performed by applying a mechanical force to the surface element. In some embodiments, the method of removing the patterned structure further comprises a sonication method.

XI. Method of Fabricating Molecules and for Delivering a Therapeutic Agent to a Target In some embodiments, the presently disclosed subject matter describes methods and processes, and products by processes, for fabricating "molecules," for use in drug discovery and drug therapies. In some embodiments, the method or process for fabricating a molecule comprises a combinatorial method or process. In some embodiments, the method for fabricating molecules comprises a non-wetting imprint lithography method.

XI.A Method of Fabricating Molecules

In some embodiments, the non-wetting imprint lithography method further comprises a surface derived from or comprising a solvent resistant, low surface energy polymeric material derived from casting low viscosity liquid materials onto a master template and then curing the low viscosity liquid materials to generate a patterned template. In some embodiments, the surface comprises a solvent resistant elastomeric material.

In some embodiments, the non-wetting imprint lithography method is used to generate isolated structures. In some embodiments, the isolated structures comprise isolated micro-structures. In some embodiments, the isolated structures comprise isolated nano-structures. In some embodiments, the isolated structures comprise a biodegradable material. In some embodiments, the isolated structures comprise a hydrophilic material. In some embodiments, the isolated structures comprise a hydrophobic material. In some embodiments, the isolated structures comprise a particular shape. In some embodiments, the isolated structures further comprise "cargo."

In some embodiments, the non-wetting imprint lithography method further comprises adding molecular modules, fragments, or domains to the solution to be molded. In some embodiments, the molecular modules, fragments, or domains impart functionality to the isolated structures. In some embodiments, the functionality imparted to the isolated structure comprises a therapeutic functionality.

In some embodiments, a therapeutic agent, such as a drug, is incorporated into the isolated structure. In some embodiments, the physiologically active drug is tethered to a linker to facilitate its incorporation into the isolated structure. In some embodiments, the domain of an enzyme or a catalyst is added to the isolated structure. In some embodiments, a ligand or an oligopeptide is added to the isolated structure. In some embodiments, the oligopeptide is functional. In some embodiments, the functional oligopeptide comprises a cell targeting peptide. In some embodiments, the functional oligopeptide comprises a cell penetrating peptide. In some embodiments an antibody or functional fragment thereof is added to the isolated structure.

In some embodiments, a binder is added to the isolated structure. In some embodiments, the isolated structure comprising the binder is used to fabricate identical structures. In some embodiments, the isolated structure comprising the binder is used to fabricate structures of a varying structure. In some embodiments, the structures of a varying structure are used to explore the efficacy of a molecule as a therapeutic agent. In some embodiments, the shape of the isolated structure mimics a biological agent. In some embodiments, the method further comprises a method for drug discovery.

XIB. Method of Delivering a Therapeutic Agent to a Target

In some embodiments, a method of delivering a therapeutic agent to a target is disclosed, the method comprising: providing a particle produced as described herein; admixing the therapeutic agent with the particle; and delivering the particle comprising the therapeutic agent to the target.

In some embodiments, the therapeutic agent comprises a drug. In some embodiments, the therapeutic agent comprises genetic material. In some embodiments, the genetic material is selected from the group consisting of a non-viral gene vector, DNA, RNA, RNAi, and a viral particle.

In some embodiments, the particle has a diameter of less than 100 microns. In some embodiments, the particle has a diameter of less than 10 microns. In some embodiments, the particle has a diameter of less than 1 micron. In some embodiments, the particle has a diameter of less than 100 nm. In some embodiments, the particle has a diameter of less than 10 nm.

In some embodiments, the particle comprises a biodegradable polymer. In some embodiments, the biodegradable polymer is selected from the group consisting of a polyester, a polyanhydride, a polyamide, a phosphorous-based polymer, a poly(cyanoacrylate), a polyurethane, a polyorthoester, a polydihydropyran, and a polyacetal. In some embodiments, the polyester is selected from the group consisting of polylactic acid, polyglycolic acid, poly(hydroxybutyrate), poly($\in$-caprolactone), poly($\beta$-malic acid), and poly(dioxanones). In some embodiments, the polyanhydride is selected from the group consisting of poly(sebacic acid), poly(adipic acid), and poly(terpthalic acid). In some embodiments, the polyamide is selected from the group consisting of poly(imino carbonates) and polyaminoacids. In some embodiments, the phosphorous-based polymer is selected from the group consisting of polyphosphates, polyphosphonates, and polyphosphazenes. In some embodiments, the polymer is responsive to stimuli, such as pH, radiation, ionic strength, temperature, and alternating magnetic or electric fields.

Responses to such stimuli can include swelling and/or heating, which can facilitate release of its cargo, or degradation.

In some embodiments, the presently disclosed subject matter describes magneto containing particles for applications in hyperthermia therapy, cancer and gene therapy, drug delivery, magnetic resonance imaging contrast agents, vaccine adjuvants, memory devices, and spintronics.

Without being bound to any one particular theory, the magneto containing particles, e.g., a magnetic nanoparticle, produce heat by the process of hyperthermia (between 41 and 46° C.) or thermo ablation (greater than 46° C.), i.e., the controlled heating of the nanoparticles upon exposure to an AC-magnetic field. The heat is used to (i) induce a phase change in the polymer component (for example melt and release an encapsulated material) and/or (ii) hyperthermia treatment of specific cells and/or (iii) increase the effectiveness of the encapsulated material. The triggering mechanism of the magnetic nanoparticles via electromagnetic heating enhance the (iv) degradation rate of the particulate; (v) can induce swelling; and/or (vi) induce dissolution/phase change that can lead to a greater surface area, which can be beneficial when treating a variety of diseases.

In some embodiments, the presently disclosed subject matter describes an alternative therapeutic agent delivery method, which utilizes "non-wetting" imprint lithography to fabricate monodisperse magnetic nanoparticles for use in a drug delivery system. Such particles can be used for: (1) hyperthermia treatment of cancer cells; (2) MRI contrast agents; (3) guided delivery of the particle; and (4) triggered degradation of the drug delivery vector.

In some embodiments, the therapeutic agent delivery system comprises a biocompatible material and a magnetic nanoparticle. In some embodiments, the biocompatible material has a melting point below 100° C. In some embodiments, the biocompatible material is selected from the group consisting of, but not limited to, a polylactide, a polyglycolide, a hydroxypropylcellulose, and a wax.

In some embodiments, once the magnetic nanoparticle is delivered to the target or is in close proximity to the target, the magnetic nanoparticle is exposed to an AC-magnetic field. The exposure to the AC-magnetic field causes the magnetic nanoparticle to undergo a controlled heating. Without being bound to any one particular theory, the controlled heating is a result of a thermo ablation process. In some embodiments, the heat is used to induce a phase change in the polymer component of the nanoparticle. In some embodiments, the phase change comprises a melting process. In some embodiments, the phase change results in the release of an encapsulated material. In some embodiments, the release of an encapsulated material comprises a controlled release. In some embodiments, the controlled release of the encapsulated material results in a concentrated dosing of the therapeutic agent. In some embodiments, the heating results in the hyperthermic treatment of the target, e.g., specific cells. In some embodiments, the heating results in an increase in the effectiveness of the encapsulated material. In some embodiments, the triggering mechanism of the magnetic nanoparticles induced by the electromagnetic heating enhances the degradation rate of the particle and can induce swelling and/or a dissolution/phase change that can lead to a greater surface area which can be beneficial when treating a variety of diseases.

In some embodiments, additional components, including drugs, such as an anticancer agent, e.g., nitrogen mustard, cisplatin, and doxorubicin; targeting ligands, such as cell-targeting peptides, cell-penetrating peptides, integrin receptor peptide (GRGDSP), melanocyte stimulating hormone, vasoactive intestinal peptide, anti-Her2 mouse antibodies, and a variety of vitamins; viruses, polysaccharides, cyclodextrins, proteins, liposomes, optical nanoparticles, such as CdSe for optical applications, and borate nanoparticles to aid in boron neutron capture therapy (BNCT) targets.

The presently described magnetic containing materials also lend themselves to other applications. The magneto-particles can be assembled into well-defined arrays driven by their shape, functionalization of the surface and/or exposure to a magnetic field for investigations of and not limited to magnetic assay devices, memory devices, spintronic applications, and separations of solutions.

Thus, the presently disclosed subject matter provides a method for delivering a therapeutic agent to a target, the method comprising:

(a) providing a particle prepared by the presently disclosed methods;
(b) admixing the therapeutic agent with the particle; and
(c) delivering the particle comprising the therapeutic agent to the target.

In some embodiments, the therapeutic agent is selected from one of a drug and genetic material. In some embodiments, the genetic material is selected from the group consisting of a non-viral gene vector, DNA, RNA, RNAi, and a viral particle.

In some embodiments, the particle comprises a biodegradable polymer. In some embodiments, the biodegradable polymer is selected from the group consisting of a polyester, a polyanhydride, a polyamide, a phosphorous-based polymer, a poly(cyanoacrylate), a polyurethane, a polyorthoester, a polydihydropyran, and a polyacetal.

In some embodiments, the polyester is selected from the group consisting of polylactic acid, polyglycolic acid, poly (hydroxybutyrate), poly($\in$-caprolactone), poly($\beta$-malic acid), and poly(dioxanones).

In some embodiments, the polyanhydride is selected from the group consisting of poly(sebacic acid), poly(adipic acid), and poly(terpthalic acid).

In some embodiments, the polyamide is selected from the group consisting of poly(imino carbonates) and polyaminoacids.

In some embodiments, the phosphorous-based polymer is selected from the group consisting of a polyphosphate, a polyphosphonate, and a polyphosphazene.

In some embodiments, the biodegradable polymer further comprises a polymer that is responsive to a stimulus. In some embodiments, the stimulus is selected from the group consisting of pH, radiation, ionic strength, temperature, an alternating magnetic field, and an alternating electric field. In some embodiments, the stimulus comprises an alternating magnetic field.

In some embodiments, the method comprises exposing the particle to an alternating magnetic field once the particle is delivered to the target. In some embodiments, the exposing of the particle to an alternating magnetic field causes the particle to produce heat through one of a hypothermia process and a thermo ablation process.

In some embodiments, the heat produced by the particle induces one of a phase change in the polymer component of the particle and a hyperthermic treatment of the target. In some embodiments, the phase change in the polymer component of the particle comprises a change from a solid phase to a liquid phase. In some embodiments, the phase change from a solid phase to a liquid phase causes the therapeutic agent to be released from the particle. In some embodiments, the release of the therapeutic agent from the particle comprises a controlled release.

In some embodiments, the target is selected from the group consisting of a cell-targeting peptide, a cell-penetrating peptide, an integrin receptor peptide (GRGDSP), a melanocyte stimulating hormone, a vasoactive intestinal peptide, an anti-Her2 mouse antibody, and a vitamin.

With respect to the methods of the presently disclosed subject matter, any animal subject can be treated. The term "subject" as used herein refers to any vertebrate species. The methods of the presently claimed subject matter are particularly useful in the diagnosis of warm-blooded vertebrates. Thus, the presently claimed subject matter concerns mammals. In some embodiments provided is the diagnosis and/or treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the diagnosis and/or treatment of livestock, including, but not limited to domesticated swine (pigs and hogs), ruminants, horses, poultry, and the like.

The following references are incorporated herein by reference in their entirety. Published International PCT Application No. WO2004081666 to DeSimone et al.; U.S. Pat. No. 6,528,080 to Dunn et al.; U.S. Pat. No. 6,592,579 to Arndt et al., Published International PCT Application No. WO0066192 to Jordan; Hilger, I. et al., *Radiology* 570-575 (2001); Mornet, S. et al., *J. Mat. Chem.,* 2161-2175 (2004); Berry, C. C. et al., *J. Phys. D: Applied Physics* 36, R198-R206 (2003); Babincova, M. et al., *Bioelectrochemistry* 55, 17-19 (2002); Wolf, S. A. et al., *Science* 16, 1488-1495 (2001); and Sun, S. et al., *Science* 287, 1989-1992 (2000); U.S. Pat. No. 6,159,443 to Hallahan; and Published PCT Application No. WO 03/066066 to Hallahan et al.

XII. Method of Patterning Natural and Synthetic Structures

In some embodiments, the presently disclosed subject matter describes methods and processes, and products by processes, for generating surfaces and molds from natural structures, single molecules, or self-assembled structures. Accordingly, in some embodiments, the presently disclosed subject matter describes a method of patterning a natural structure, single molecule, and/or a self-assembled structure. In some embodiments, the method further comprises replicating the natural structure, single molecule, and/or a self-assembled structure. In some embodiments, the method further comprises replicating the functionality of the natural structure, single molecule, and/or a self-assembled structure.

More particularly, in some embodiments, the method further comprises taking the impression or mold of a natural structure, single molecule, and/or a self-assembled structure. In some embodiments, the impression or mold is taken with a low surface energy polymeric precursor. In some embodiments, the low surface energy polymeric precursor comprises a perfluoropolyether (PFPE) functionally terminated diacrylate. In some embodiments, the natural structure, single molecule, and/or self-assembled structure is selected from the group consisting of enzymes, viruses, antibodies, micelles, and tissue surfaces.

In some embodiments, the impression or mold is used to replicate the features of the natural structure, single molecule, and/or a self-assembled structure into an isolated object or a surface. In some embodiments, a non-wetting imprint lithography method is used to impart the features into a molded part or surface. In some embodiments, the molded part or surface produced by this process can be used in many applications, including, but not limited to, drug delivery, medical devices, coatings, catalysts, or mimics of the natural structures from which they are derived. In some embodiments, the natural structure comprises biological tissue. In some embodiments, the biological tissue comprises tissue from a bodily organ, such as a heart. In some embodiments, the biological tissue comprises vessels and bone. In some embodiments, the biological tissue comprises tendon or cartilage. For example, in some embodiments, the presently disclosed subject matter can be used to pattern surfaces for tendon and cartilage repair. Such repair typically requires the use of collagen tissue, which comes from cadavers and must be machined for use as replacements. Most of these replacements fail because one cannot lay down the primary pattern that is required for replacement. The soft lithographic methods described herein alleviate this problem.

In some embodiments, the presently disclosed subject matter can be applied to tissue regeneration using stem cells. Almost all stem cell approaches known in the art require molecular patterns for the cells to seed and then grow, thereby taking the shape of an organ, such as a liver, a kidney, or the like. In some embodiments, the molecular scaffold is cast and used as crystals to seed an organ in a form of transplant therapy. In some embodiments, the stem cell and nano-substrate is seeded into a dying tissue, e.g., liver tissue, to promote growth and tissue regeneration. In some embodiments, the material to be replicated in the mold comprises a material that is similar to or the same as the material that was originally molded. In some embodiments, the material to be replicated in the mold comprises a material that is different from and/or has different properties than the material that was originally molded. This approach could play an important role in addressing the organ transplant shortage.

In some embodiments, the presently disclosed subject matter is used to take the impression of one of an enzyme, a bacterium, and a virus. In some embodiments, the enzyme, bacterium, or virus is then replicated into a discrete object or onto a surface that has the shape reminiscent of that particular enzyme, bacterium, or virus replicated into it. In some embodiments, the mold itself is replicated on a surface, wherein the surface-attached replicated mold acts as a receptor site for an enzyme, bacterium, or virus particle. In some embodiments, the replicated mold is useful as a catalyst, a diagnostic sensor, a therapeutic agent, a vaccine, and the like. In some embodiments, the surface-attached replicated mold is used to facilitate the discovery of new therapeutic agents.

In some embodiments, the macromolecular, e.g., enzyme, bacterial, or viral, molded "mimics" serve as non-self-replicating entities that have the same surface topography as the original macromolecule, bacterium, or virus. In some embodiments, the molded mimics are used to create biological responses, e.g., an allergic response, to their presence, thereby creating antibodies or activating receptors. In some embodiments, the molded mimics function as a vaccine. In some embodiments, the efficacy of the biologically-active shape of the molded mimics is enhanced by a surface modification technique.

XIII. Method of Modifying the Surface of an Imprint Lithography Mold to Impart Surface Characteristics to Molded Products In some embodiments, the presently disclosed subject matter describes a method of modifying the surface of an imprint lithography mold. In some embodiments, the method further comprises imparting surface characteristics to a molded product. In some embodiments, the molded product comprises an isolated molded product. In some embodiments, the isolate molded product is formed using a non-wetting imprint lithography technique. In some embodiments, the molded product comprises a contact lens, a medical device, and the like.

More particularly, the surface of a solvent resistant, low surface energy polymeric material, or more particularly a PFPE mold is modified by a surface modification step, wherein the surface modification step is selected from the group consisting of plasma treatment, chemical treatment, and the adsorption of molecules. In some embodiments, the molecules adsorbed during the surface modification step are selected from the group consisting of polyelectrolytes, poly(vinylalcohol), alkylhalosilanes, and ligands. In some embodiments, the structures, particles, or objects obtained from the surface-treated molds can be modified by the surface treatments in the mold. In some embodiments, the modification comprises the pre-orientation of molecules or moieties with the molecules comprising the molded products. In some embodiments, the pre-orientation of the molecules or moieties imparts certain properties to the molded products, including catalytic, wettable, adhesive, non-stick, interactive, or not interactive, when the molded product is placed in another environment. In some embodiments, such properties are used to facilitate interactions with biological tissue or to prevent interaction with biological tissues. Applications of the presently disclosed subject matter include sensors, arrays, medical implants, medical diagnostics, disease detection, and separation media.

XIV. Methods for Selectively Exposing the Surface of an Article to an Agent

Also disclosed herein is a method for selectively exposing the surface of an article to an agent. In some embodiments the method comprises:

(a) shielding a first portion of the surface of the article with a masking system, wherein the masking system comprises a elastomeric mask in conformal contact with the surface of the article; and (b) applying an agent to be patterned within the masking system to a second portion of the surface of the article, while preventing application of the agent to the first portion shielded by the masking system.

In some embodiments, the elastomeric mask comprises a plurality of channels. In some embodiments, each of the channels has a cross-sectional dimension of less than about 1 millimeter. In some embodiments, each of the channels has a cross-sectional dimension of less than about 1 micron. In some embodiments, each of the channels has a cross-sectional dimension of less than about 100 nm. In some embodiments, each of the channels has a cross-sectional dimension of about 1 nm. In some embodiments, the agent swells the elastomeric mask less than 25%.

In some embodiments, the agent comprises an organic electroluminescent material or a precursor thereof. In some embodiments, the method further comprising allowing the organic electroluminescent material to form from the agent at the second portion of the surface, and establishing electrical communication between the organic electroluminescent material and an electrical circuit.

In some embodiments, the agent comprises a liquid or is carried in a liquid. In some embodiments, the agent comprises the product of chemical vapor deposition. In some embodiments, the agent comprises a product of deposition from a gas phase. In some embodiments, the agent comprises a product of e-beam deposition, evaporation, or sputtering. In some embodiments, the agent comprises a product of electrochemical deposition. In some embodiments, the agent comprises a product of electroless deposition. In some embodiments, the agent is applied from a fluid precursor. In some embodiments, comprises a solution or suspension of an inorganic compound. In some embodiments, the inorganic compound hardens on the second portion of the article surface.

In some embodiments, the fluid precursor comprises a suspension of particles in a fluid carrier. In some embodiments, the method further comprises allowing the fluid carrier to dissipate thereby depositing the particles at the first region of the article surface. In some embodiments, the fluid precursor comprises a chemically active agent in a fluid carrier. In some embodiments, the method further comprises allowing the fluid carrier to dissipate thereby depositing the chemically active agent at the first region of the article surface.

In some embodiments, the chemically active agent comprises a polymer precursor. In some embodiments, the method further comprises forming a polymeric article from the polymer precursor. In some embodiments, the chemically active agent comprises an agent capable of promoting deposition of a material. In some embodiments, the chemically active agent comprises an etchant. In some embodiments, the method further comprises allowing the second portion of the surface of the article to be etched. In some embodiments, the method further comprises removing the elastomeric mask of the masking system from the first portion of the article surface while leaving the agent adhered to the second portion of the article surface.

XV. Methods for Forming Engineered Membranes

The presently disclosed subject matter also describes a method for forming an engineered membrane. In some embodiments, a patterned non-wetting template is formed by contacting a first liquid material, such as a PFPE material, with a patterned substrate and treating the first liquid material, for example, by curing through exposure to UV light to form a patterned non-wetting template. The patterned substrate comprises a plurality of recesses or cavities configured in a specific shape such that the patterned non-wetting template comprises a plurality of extruding features. The patterned non-wetting template is contacted with a second liquid material, for example, a photocurable resin. A force is then applied to the patterned non-wetting template to displace an excess amount of second liquid material or "scum layer." The second liquid material is then treated, for example, by curing through exposure to UV light to form an interconnected structure comprising a plurality of shape and size specific holes. The interconnected structure is then removed from the non-wetting template. In some embodiments, the interconnected structure is used as a membrane for separations

XVI. Methods for Inspecting Processes and Products by Processes

It will be important to inspect the objects/structures/particles described herein for accuracy of shape, placement and utility. Such inspection can allow for corrective actions to be taken or for defects to be removed or mitigated. The range of approaches and monitoring devices useful for such inspections include: air gages, which use pneumatic pressure and flow to measure or sort dimensional attributes; balancing machines and systems, which dynamically measure and/or correct machine or component balance; biological microscopes, which typically are used to study organisms and their vital processes; bore and ID gages, which are designed for internal diameter dimensional measurement or assessment; boroscopes, which are inspection tools with rigid or flexible optical tubes for interior inspection of holes, bores, cavities, and the like; calipers, which typically use a precise slide movement for inside, outside, depth or step measurements, some of which are used for comparing or transferring dimensions; CMM probes, which are transducers that convert physical measurements into electrical signals, using various measuring systems within the probe structure; color and appearance instruments, which, for example, typically are used to measure the properties of paints and coatings including color, gloss, haze and transparency; color sensors, which register items by contrast, true color, or translucent index, and are based on one of the color models, most commonly the RGB model (red, green, blue); coordinate measuring machines, which are mechanical systems designed to move a measuring probe to determine the coordinates of points on a work piece surface; depth gages, which are used to measure of the depth of holes, cavities or other component features; digital/video microscopes, which use digital technology to display the magnified image; digital readouts, which are specialized displays for position and dimension readings from inspection gages and linear scales, or rotary encoders on machine tools; dimensional gages and instruments, which provide quantitative measurements of a product's or component's dimensional and form attributes such as wall thickness, depth, height, length, I.D., O.D., taper or bore; dimensional and profile scanners, which gather two-dimensional or three-dimensional information about an object and are available in a wide variety of configurations and technologies; electron microscopes, which use a focused beam of electrons instead of light to "image" the specimen and gain information as to its structure and composition; fiberscopes, which are inspection tools with flexible optical tubes for interior inspection of holes, bores, and cavities; fixed gages, which are designed to access a specific attribute based on comparative gaging, and include Angle Gages, Ball Gages, Center Gages, Drill Size Gages, Feeler Gages, Fillet Gages, Gear Tooth Gages, Gage or Shim Stock, Pipe Gages, Radius Gages, Screw or Thread Pitch Gages, Taper Gages, Tube Gages, U.S. Standard Gages (Sheet/Plate), Weld Gages and Wire Gages; specialty/form gages, which are used to inspect parameters such as roundness, angularity, squareness, straightness, flatness, runout, taper and concentricity; gage blocks, which are manufactured to precise gagemaker tolerance grades for calibrating, checking, and setting fixed and comparative gages; height gages, which are used for measuring the height of components or product features; indicators and comparators, which measure where the linear movement of a precision spindle or probe is amplified; inspection and gaging accessories, such as layout and marking tolls, including hand tools, supplies and accessories for dimensional measurement, marking, layout or other machine shop applications such as scribes, transfer punches, dividers, and layout fluid; interferometers, which are used to measure distance in terms of wavelength and to determine wavelengths of particular light sources; laser micrometers, which measure extremely small distances using laser technology; levels, which are mechanical or electronic tools that measure the inclination of a surface relative to the earth's surface; machine alignment equipment, which is used to align rotating or moving parts and machine components; magnifiers, which are inspection instruments that are used to magnify a product or part detail via a lens system; master and setting gages, which provide dimensional standards for calibrating other gages; measuring microscopes, which are used by toolmakers for measuring the properties of tools, and often are used for dimensional measurement with lower magnifying powers to allow for brighter, sharper images combined with a wide field of view; metallurgical microscopes, which are used for metallurgical inspection; micrometers, which are instruments for precision dimensional gaging consisting of a ground spindle and anvil mounted in a C-shaped steel frame. Noncontact laser micrometers are also available; microscopes (all types), which are instruments that are capable of producing a magnified image of a small object; optical/light microscopes, which use the visible or near-visible portion of the electromagnetic spectrum; optical comparators, which are instruments that project a magnified image or profile of a part onto a screen for comparison to a standard overlay profile or scale; plug/pin gages, which are used for a "go/no-go" assessment of hole and slot dimensions or locations compared to specified tolerances; protractors and angle gages, which measure the angle between two surfaces of a part or assembly; ring gages, which are used for "go/no-go" assessment compared to the specified dimensional tolerances or attributes of pins, shafts, or threaded studs; rules and scales, which are flat, graduated scales used for length measurement, and which for OEM applications, digital or electronic linear scales are often used; snap gages, which are used in production settings where specific diametrical or thickness measurements must be repeated frequently with precision and accuracy; specialty microscopes, which are used for specialized applications including metallurgy, gemology, or use specialized techniques like acoustics or microwaves to perform their function; squares, which are used to indicate if two surfaces of a part or assembly are perpendicular; styli, probes, and cantilevers, which are slender rod-shaped stems and contact tips or points used to probe surfaces in conjunction with profilometers, SPMs, CMMs, gages and dimensional scanners; surface profilometers, which measure surface profiles, roughness, waviness and other finish parameters by scanning a mechanical stylus across the sample or through noncontact methods; thread gages, which are dimensional instruments for measuring thread size, pitch or other parameters; and videoscopes, which are inspection tools that capture images from inside holes, bores or cavities.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Representative Procedure for Synthesis and Curing Photocurable Perfluoropolyethers In some embodiments, the synthesis and curing of PFPE materials of the presently disclosed subject matter is performed by using the method described by Rolland J. P., et al., *J. Am. Chem. Soc.*, 2004, 126, 2322-2323. Briefly, this method involves the methacrylate-functionalization of a commercially available PFPE diol ($M_n$=3800 g/mol) with isocyanatoethyl methacrylate. Subsequent photocuring of the material is accomplished through blending with 1 wt % of 2,2-dimethoxy-2-phenylacetophenone and exposure to UV radiation ($\lambda$=365 nm).

More particularly, in a typical preparation of perfluoropolyether dimethacrylate (PFPE DMA), poly(tetrafluoroethylene oxide-co-difluoromethylene oxide)$\alpha,\omega$ diol (ZDOL, average $M_n$ ca. 3,800 g/mol, 95%, Aldrich Chemical Company, Milwaukee, Wis., United States of America) (5.7227 g, 1.5 mmol) was added to a dry 50 mL round bottom flask and purged with argon for 15 minutes. 2-isocyanatoethyl methacrylate (EIM, 99%, Aldrich) (0.43 mL, 3.0 mmol) was then added via syringe along with 1,1,2-trichlorotrifluoroethane (Freon 113 99%, Aldrich) (2 mL), and dibutyltin diacetate (DBTDA, 99%, Aldrich) (50 µL). The solution was immersed in an oil bath and allowed to stir at 50° C. for 24 h. The solution was then passed through a chromatographic column (alumina, Freon 113, 2×5 cm). Evaporation of the solvent yielded a clear, colorless, viscous oil, which was further purified by passage through a 0.22-µm polyethersulfone filter.

In a representative curing procedure for PFPE DMA, 1 wt % of 2,2-dimethoxy-2-phenyl acetophenone (DMPA, 99% Aldrich), (0.05 g, 2.0 mmol) was added to PFPE DMA (5 g, 1.2 mmol) along with 2 mL Freon 113 until a clear solution was formed. After removal of the solvent, the cloudy viscous oil was passed through a 0.22-µm polyethersulfone filter to remove any DMPA that did not disperse into the PFPE DMA. The filtered PFPE DMA was then irradiated with a UV source (Electro-Lite Corporation, Danbury, Conn., United States of America, UV curing chamber model no. 81432-ELC-500, $\lambda$=365 nm) while under a nitrogen purge for 10 min. This resulted in a clear, slightly yellow, rubbery material.

Example 2

Representative Fabrication of a PFPE DMA Device

In some embodiments, a PFPE DMA device, such as a stamp, was fabricated according to the method described by Rolland, J. P., et al., *J. Am. Chem. Soc.*, 2004, 126, 2322-2323. Briefly, the PFPE DMA containing a photoinitiator, such as DMPA, was spin coated (800 rpm) to a thickness of 20 µm onto a Si wafer containing the desired photoresist pattern. This coated wafer was then placed into the UV curing chamber and irradiated for 6 seconds. Separately, a thick layer (about 5 mm) of the material was produced by pouring the PFPE DMA containing photoinitiator into a mold surrounding the Si wafer containing the desired photoresist pattern. This wafer was irradiated with UV light for one minute. Following this, the thick layer was removed. The thick layer was then placed on top of the thin layer such that the patterns in the two layers were precisely aligned, and then the entire device was irradiated for 10 minutes. Once complete, the entire device was peeled from the Si wafer with both layers adhered together.

Example 3

Figure 13:
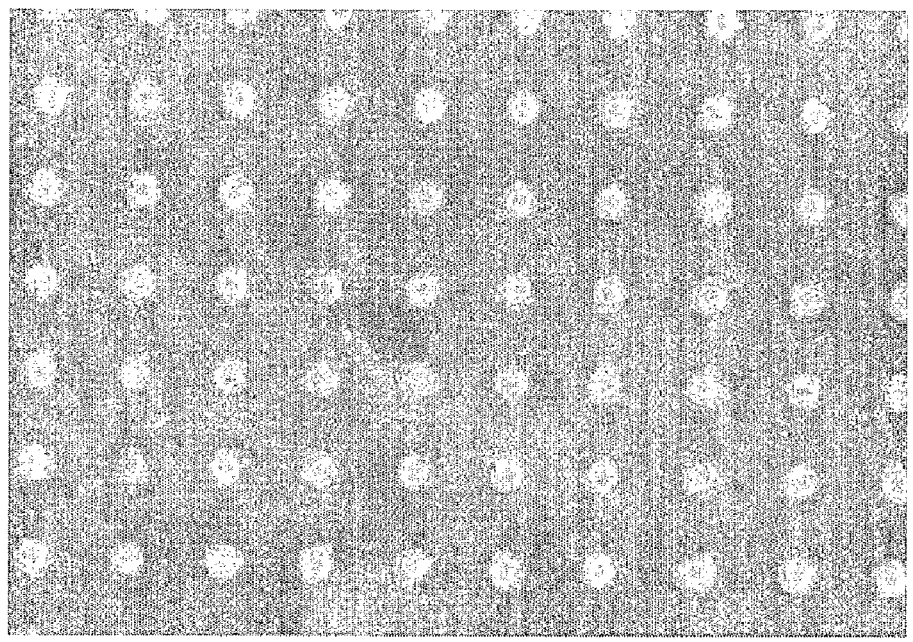
FIG. 13 is a scanning electron micrograph of a silicon master comprising 200 nm trapezoidal patterns.
Figure 14:
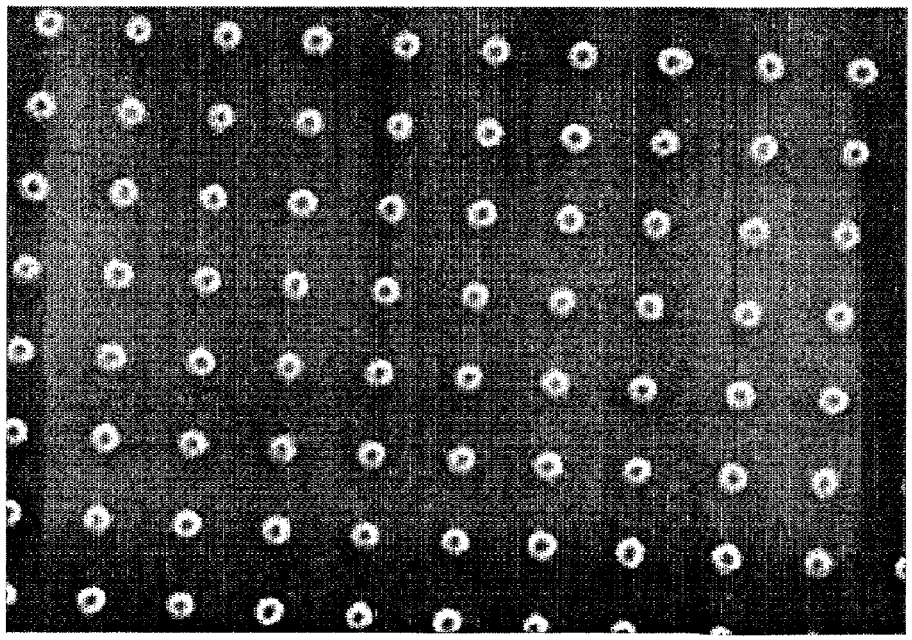
FIG. 14 is a scanning electron micrograph of 200-nm isolated trapezoidal particles of poly(ethylene glycol) (PEG) diacrylate.

Fabrication of Isolated Particles using Non-Wetting Imprint Lithography 3.1 Fabrication of 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (See FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 14).

3.2 Fabrication of 500-nm Conical PEG Particles

Figure 12:
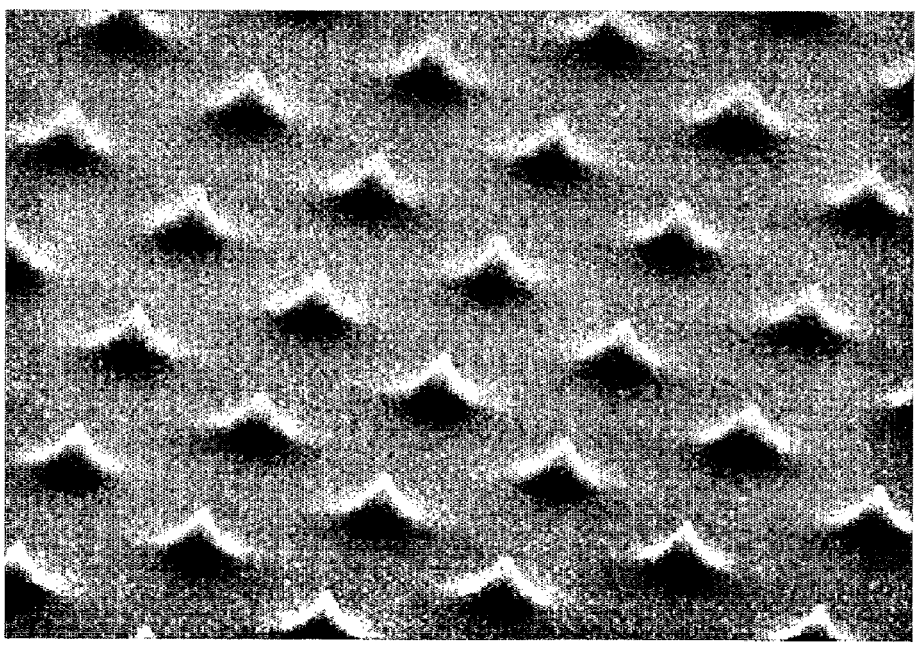
FIG. 12 is a scanning electron micrograph of a silicon master comprising 500 nm conical patterns that are <50 nm at the tip.
Figure 15:
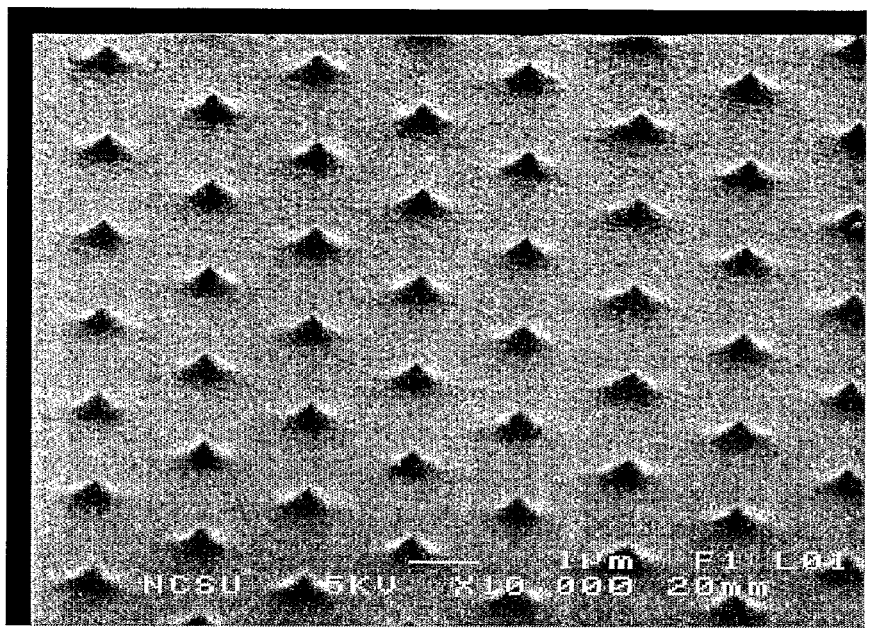
FIG. 15 is a scanning electron micrograph of 500-nm isolated conical particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light ($\lambda$=365 nm) for ten minutes while under a nitrogen purge. Particles are observed after separation of the PFPE mold and the treated silicon wafer using scanning electron microscopy (SEM) (see FIG. 15).

3.3 Fabrication of 3-µm Arrow-Shaped PEG Particles

Figure 11:
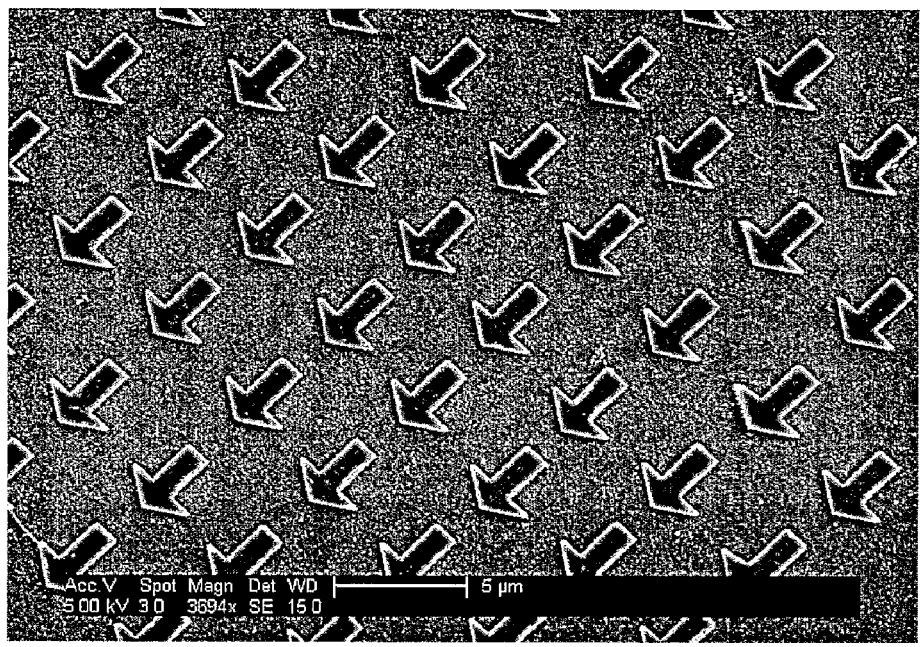
FIG. 11 is a scanning electron micrograph of a silicon master comprising 3-μm arrow-shaped patterns.
Figure 16:
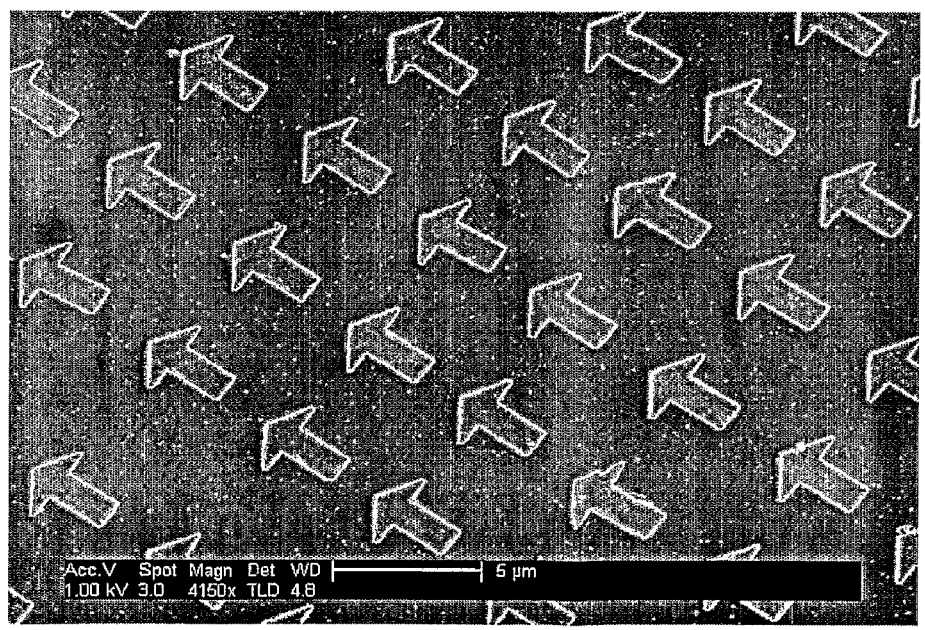
FIG. 16 is a scanning electron micrograph of 3-μm isolated arrow-shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light (λ=365 nm) for ten minutes while under a nitrogen purge. Particles are observed after separation of the PFPE mold and the treated silicon wafer using scanning electron microscopy (SEM) (see FIG. 16).

3.4 Fabrication of 200-nm×750-nm×250-nm Rectangular PEG Particles

Figure 17:
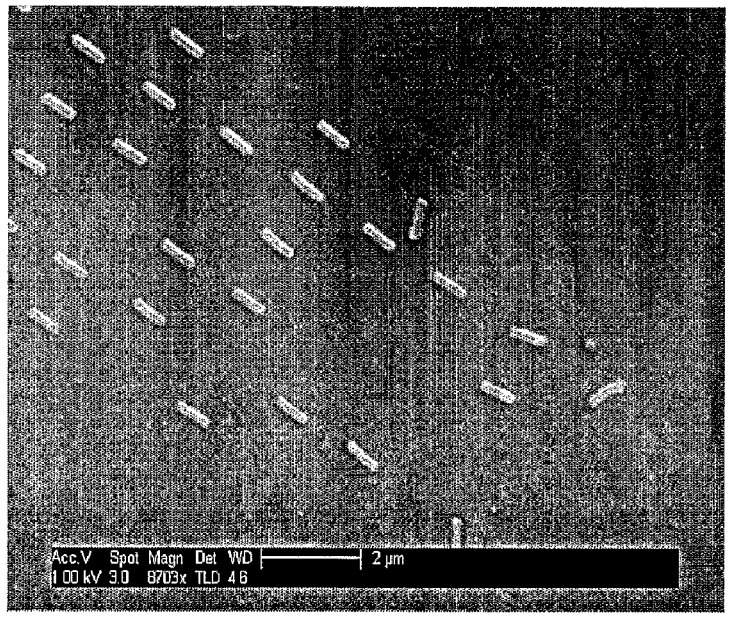
FIG. 17 is a scanning electron micrograph of 200-nm×750-nm×250-nm rectangular shaped particles of PEG diacrylate.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm×750-nm×250-nm rectangular shapes. A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light (λ=365 nm) for ten minutes while under a nitrogen purge. Particles are observed after separation of the PFPE mold and the treated silicon wafer using scanning electron microscopy (SEM) (see FIG. 17).

Figure 18:
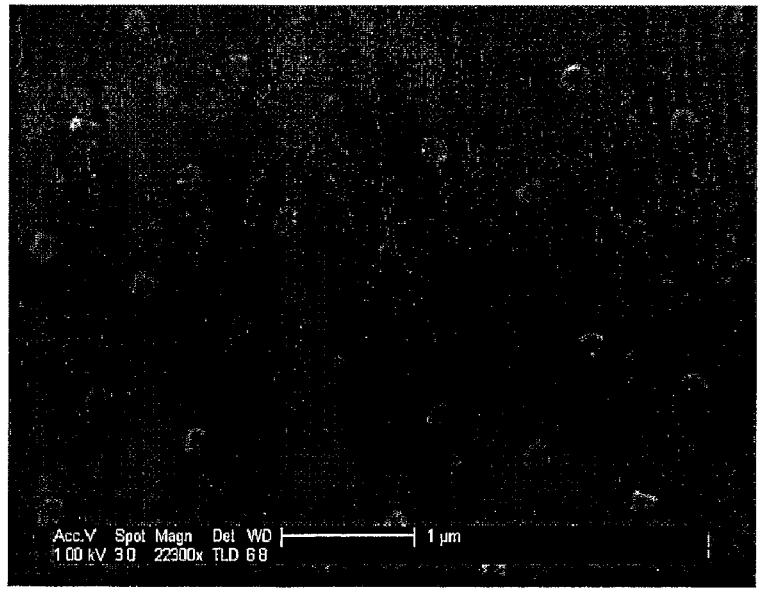
FIG. 18 is a scanning electron micrograph of 200-nm isolated trapezoidal particles of trimethylopropane triacrylate (TMPTA).

3.5 Fabrication of 200-nm Trapezoidal Trimethylopropane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl)silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light (λ=365 nm) for ten minutes while under a nitrogen purge. Particles are observed after separation of the PFPE mold and the treated silicon wafer using scanning electron microscopy (SEM) (see FIG. 18).

Figure 19:
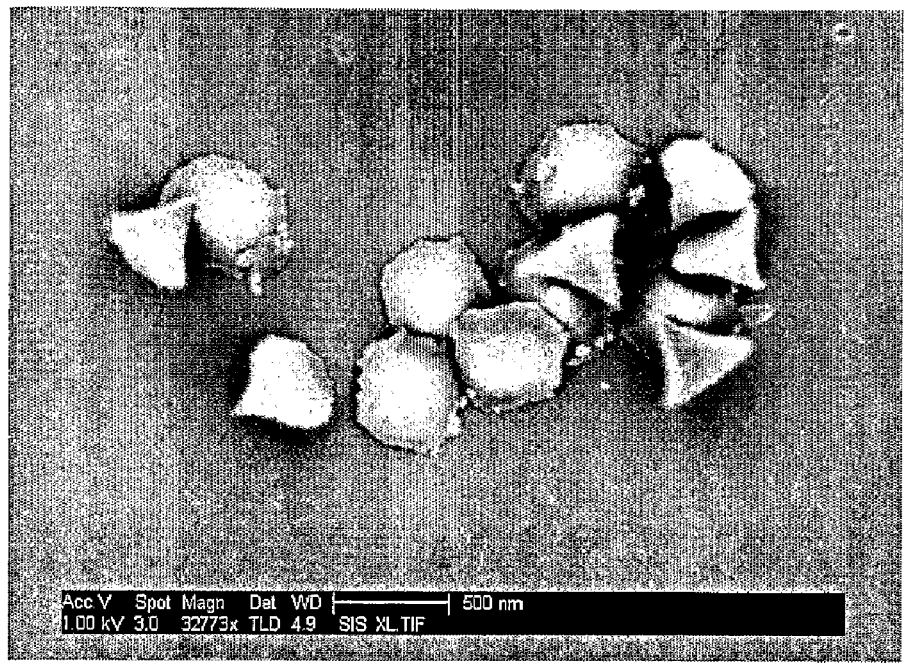
FIG. 19 is a scanning electron micrograph of 500-nm isolated conical particles of TMPTA.
Figure 20:
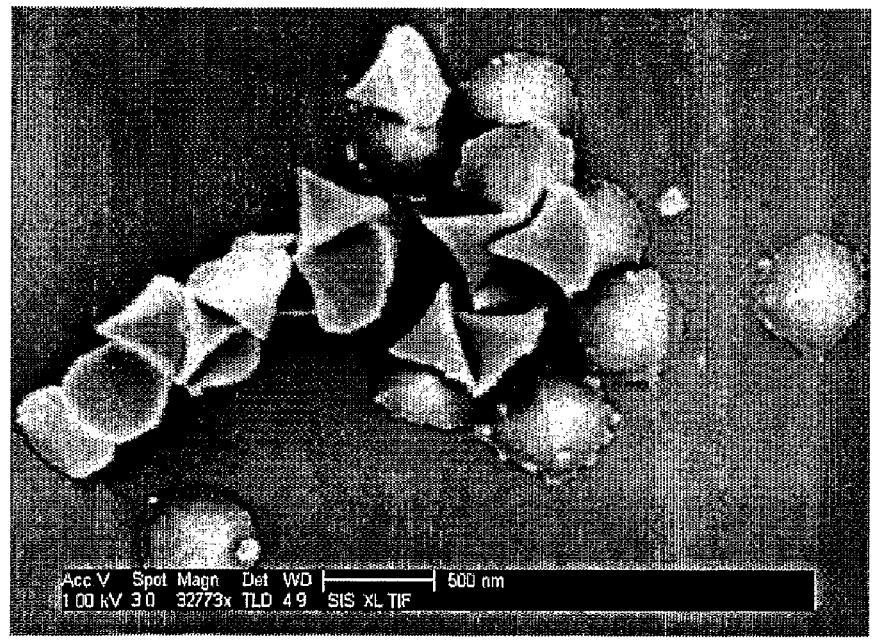
FIG. 20 is a scanning electron micrograph of 500-nm isolated conical particles of TMPTA, which have been printed using an embodiment of the presently described non-wetting imprint lithography method and harvested mechanically using a doctor blade.

3.6 Fabrication of 500-nm Conical Trimethylopropane Triacrylate (TMPTA) Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light (λ=365 nm) for ten minutes while under a nitrogen purge. Particles are observed after separation of the PFPE mold and the treated silicon wafer using scanning electron microscopy (SEM) (see FIG. 19). Further, FIG. 20 shows a scanning electron micrograph of 500-nm isolated conical particles of TMPTA, which have been printed using an embodiment of the presently described non-wetting imprint lithography method and harvested mechanically using a doctor blade. The ability to harvest particles in such a way offers conclusive evidence for the absence of a "scum layer."

3.7 Fabrication of 3-µm Arrow-Shaped TMPTA Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly (dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light (λ=365 nm) for ten minutes while under a nitrogen purge. Particles are observed after separation of the PFPE mold and the treated silicon wafer using scanning electron microscopy (SEM).

3.8 Fabrication of 200-nm Trapezoidal Poly(Lactic Acid) (PLA) Particles

Figure 21:
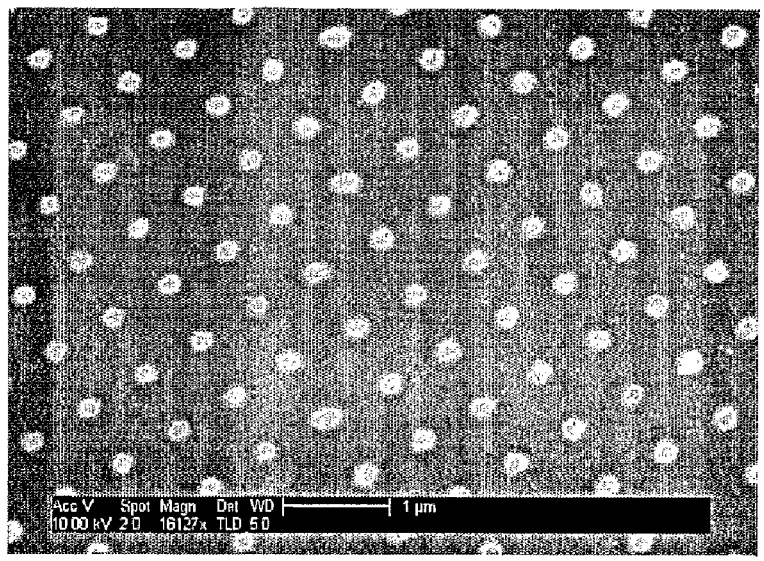
FIG. 21 is a scanning electron micrograph of 200-nm isolated trapezoidal particles of poly(lactic acid) (PLA).
Figure 22:
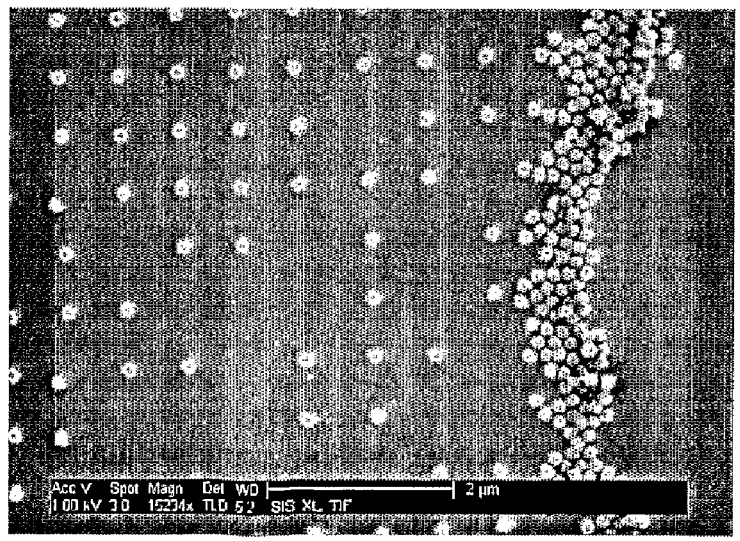
FIG. 22 is a scanning electron micrograph of 200-nm isolated trapezoidal particles of poly(lactic acid) (PLA), which have been printed using an embodiment of the presently described non-wetting imprint lithography method and harvested mechanically using a doctor blade.

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and approximately 20 µL of stannous octoate catalyst/initiator is added to the liquid monomer. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 21). Further, FIG. 22 is a scanning electron micrograph of 200-nm isolated trapezoidal particles of poly(lactic acid) (PLA), which have been printed using an embodiment of the presently described non-wetting imprint lithography method and harvested mechanically using a doctor blade. The ability to harvest particles in such a way offers conclusive evidence for the absence of a "scum layer."

3.9 Fabrication of 3-µm Arrow-Shaped (PLA) Particles

Figure 23:
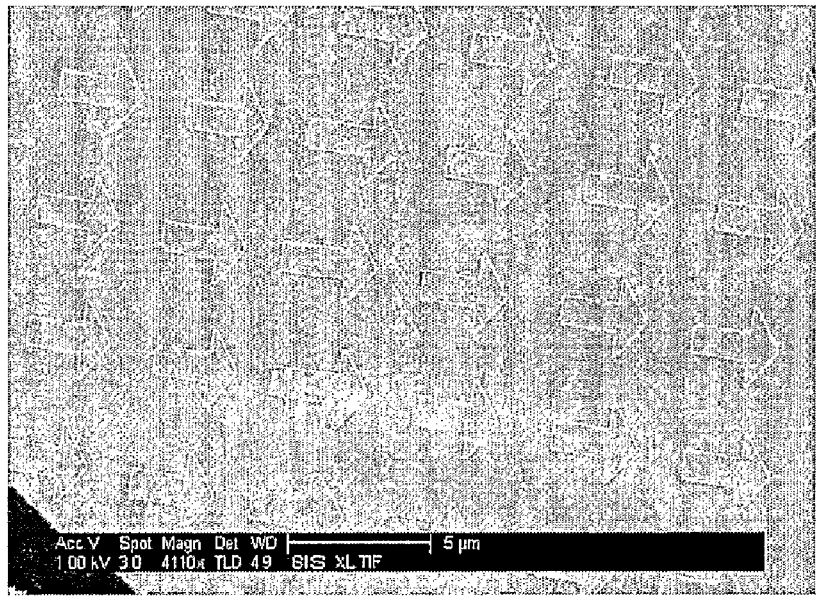
FIG. 23 is a scanning electron micrograph of 3-μm isolated arrow-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and ~20 µL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl)silane via vapor deposition in a desiccator for 20 minutes. Following this, 50 µL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 23).

3.10 Fabrication of 500-nm Conical Shaped (PLA) Particles

Figure 24:
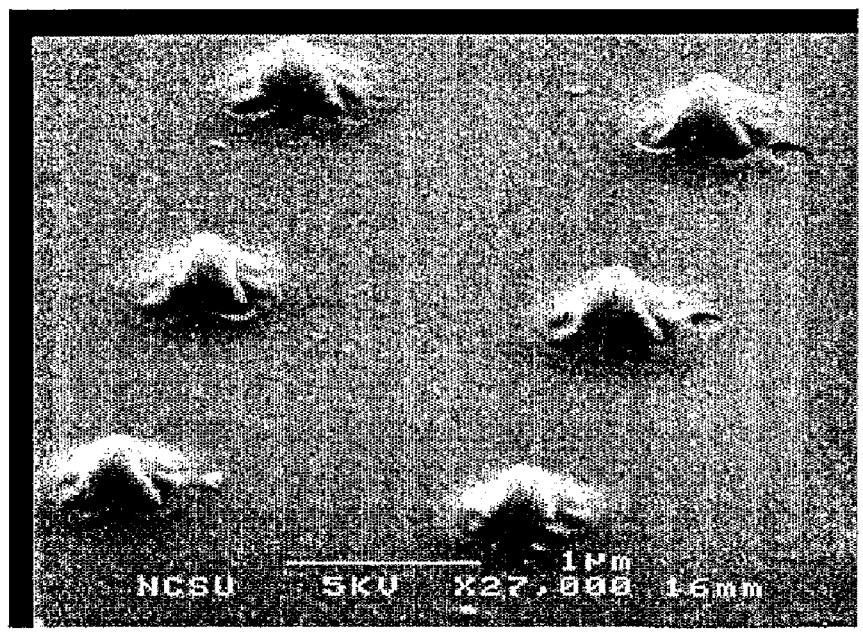
FIG. 24 is a scanning electron micrograph of 500-nm isolated conical-shaped particles of PLA.

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, one gram of (3S)-cis-3,6-dimethyl-1,4-dioxane-2,5-dione (LA) is heated above its melting temperature (92° C.) to 110° C. and ~20 µL of stannous octoate catalyst/initiator is added to the liquid monomer. Flat, uniform, non-wetting surfaces are generated by treating a silicon wafer cleaned with "piranha" solution (1:1 concentrated sulfuric acid: 30% hydrogen peroxide (aq) solution) with trichloro(1H,1H,2H,2H-perfluorooctyl)silane via vapor deposition in a desiccator for 20 minutes. Following this, 50 µL of molten LA containing catalyst is then placed on the treated silicon wafer preheated to 110° C. and the patterned PFPE mold is placed on top of it. The substrate is then placed in a molding apparatus and a small pressure is applied to push out excess monomer. The entire apparatus is then placed in an oven at 110° C. for 15 hours. Particles are observed after cooling to room temperature and separation of the PFPE mold and the treated silicon wafer using scanning electron microscopy (SEM) (see FIG. 24).

3.11 Fabrication of 200-nm Trapezoidal Poly(Pyrrole) (Ppy) Particles

Figure 25:
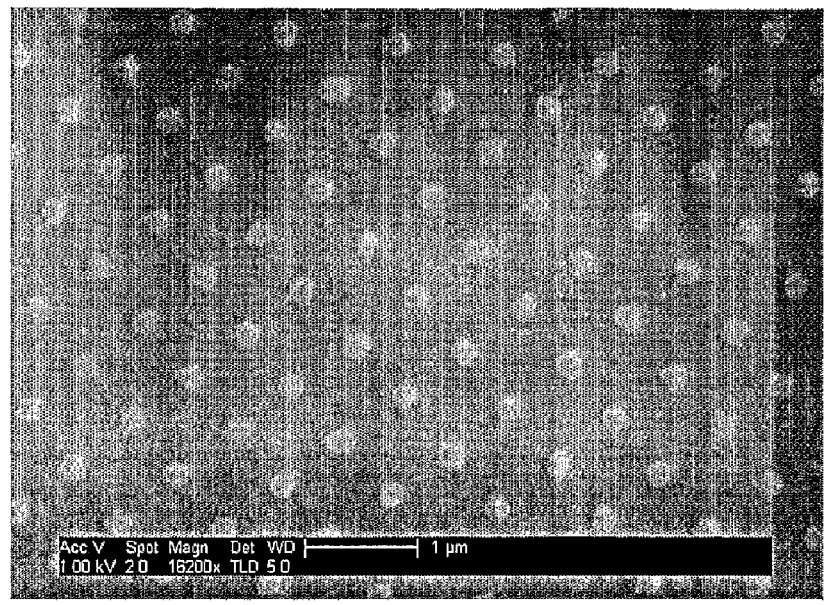
FIG. 25 is a scanning electron micrograph of 200-nm isolated trapezoidal particles of poly(pyrrole) (Ppy).

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid: 30% hydrogen peroxide (aq) deposition in a desiccator for 20 minutes. Separately, 50 µL of a 1:1 v:v solution of tetrahydrofuran:pyrrole is added to 50 µL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 25) after release of the vacuum and separation of the PFPE mold and the treated silicon wafer.

3.12 Fabrication of 3-µm Arrow-Shaped (Ppy) Particles

Figure 26:
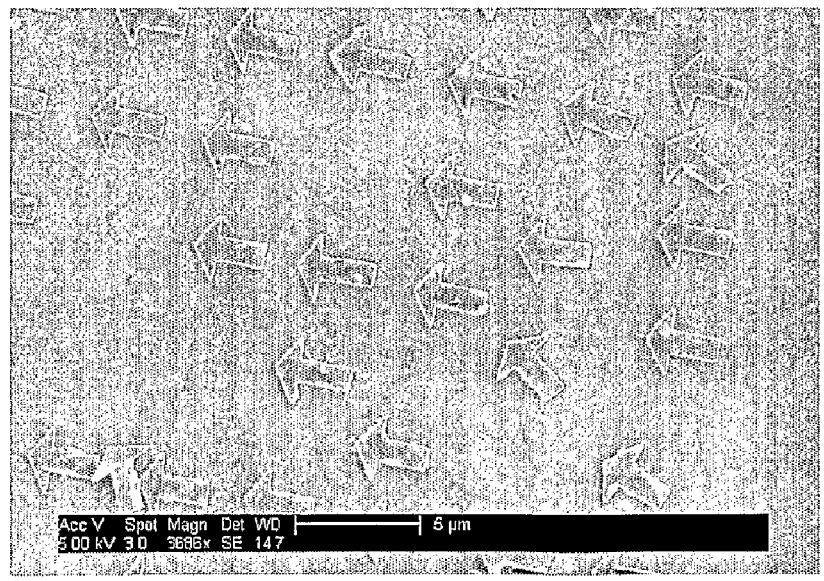
FIG. 26 is a scanning electron micrograph of 3-μm arrow-shaped Ppy particles.

A patterned perfluoropolyether (PFPE) mold is generated by pouring a PFPE-dimethacrylate (PFPE-DMA) containing 1-hydroxycyclohexyl phenyl ketone over a silicon substrate patterned with 3-µm arrow shapes (see FIG. 11). A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Separately, 50 µL of a 1:1 v:v solution of tetrahydrofuran:pyrrole is added to 50 µL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 26) after release of the vacuum and separation of the PFPE mold and the treated silicon wafer.

3.13 Fabrication of 500-nm Conical (Ppy) Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Separately, 50 µL of a 1:1 v:v solution of tetrahydrofuran:pyrrole is added to 50 µL of 70% perchloric acid (aq). A clear, homogenous, brown solution quickly forms and develops into black, solid, polypyrrole in 15 minutes. A drop of this clear, brown solution (prior to complete polymerization) is placed onto a treated silicon wafer and into a stamping apparatus and a pressure is applied to remove excess solution. The apparatus is then placed into a vacuum oven for 15 h to remove the THF and water. Particles are observed using scanning electron microscopy (SEM) (see FIG. 27) after release of the vacuum and separation of the PFPE mold and the treated silicon wafer.

3.14 Encapsulation of Fluorescently Tagged DNA Inside 200-nm Trapezoidal PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. 20 µL of water and 20 µL of PEG diacrylate monomer are added to 8 nanomoles of 24 bp DNA oligonucleotide that has been tagged with a fluorescent dye, CY-3. Flat, uniform, non-wetting surfaces are generated by treating a silicon wafer cleaned with "piranha" solution (1:1 concentrated sulfuric acid:30% hydrogen peroxide (aq) solution) with trichloro (1H,1H,2H,2H-perfluorooctyl)silane via vapor deposition in a desiccator for 20 minutes. Following this, 50 µL of the PEG diacrylate solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Particles are observed after separation of the PFPE mold and the treated silicon wafer using confocal fluorescence microscopy (see FIG. 28). Further, FIG. 28A shows a fluorescent confocal micrograph of 200 nm trapezoidal PEG nanoparticles which contain 24-mer DNA strands that are tagged with CY-3. FIG. 28B is optical micrograph of the 200-nm isolated trapezoidal particles of PEG diacrylate that contain fluorescently tagged DNA. FIG. 28C is the overlay of the images provided in FIGS. 28A and 28B, showing that every particle contains DNA.

3.15 Encapsulation of Magnetite Nanoparticles Inside 500-nm Conical PEG Particles A patterned perfluoropolyether (PFPE) mold is generated by pouring a PFPE-dimethacrylate (PFPE-DMA) containing 1-hydroxycyclohexyl phenyl ketone over a silicon substrate patterned with 500-nm conical shapes (see FIG. 12). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Separately, citrate capped magnetite nanoparticles were synthesized by reaction of ferric chloride (40 mL of a 1 M aqueous solution) and ferrous chloride (10 mL of a 2 M aqueous hydrochloric acid solution) which is added to ammonia (500 mL of a 0.7 M aqueous solution). The resulting precipitate is collected by centrifugation and then stirred in 2 M perchloric acid. The final solids are collected by centrifugation. 0.290 g of these perchlorate-stabilized nanoparticles are suspended in 50 mL of water and heated to 90° C. while stirring. Next, 0.106 g of sodium citrate is added. The solution is stirred at 90° C. for 30 min to yield an aqueous solution of citrate-stabilized iron oxide nanoparticles. 50 µL of this solution is added to 50 µL of a PEG diacrylate solution in a microtube. This microtube is vortexed for ten seconds. Following this, 50 µL of this PEG diacrylate/particle solution is then placed on the treated silicon wafer and the patterned PFPE mold placed on top of it. The substrate is then placed in a molding apparatus and a small pressure is applied to push out excess PEG-diacrylate/particle solution. The entire apparatus is then subjected to UV light ($\lambda$=365 nm) for ten minutes while under a nitrogen purge. Nanoparticle-containing PEG-diacrylate particles are observed after separation of the PFPE mold and the treated silicon wafer using optical microscopy.

3.16 Fabrication of Isolated Particles on Glass Surfaces Using "Double Stamping"

Figure 29:
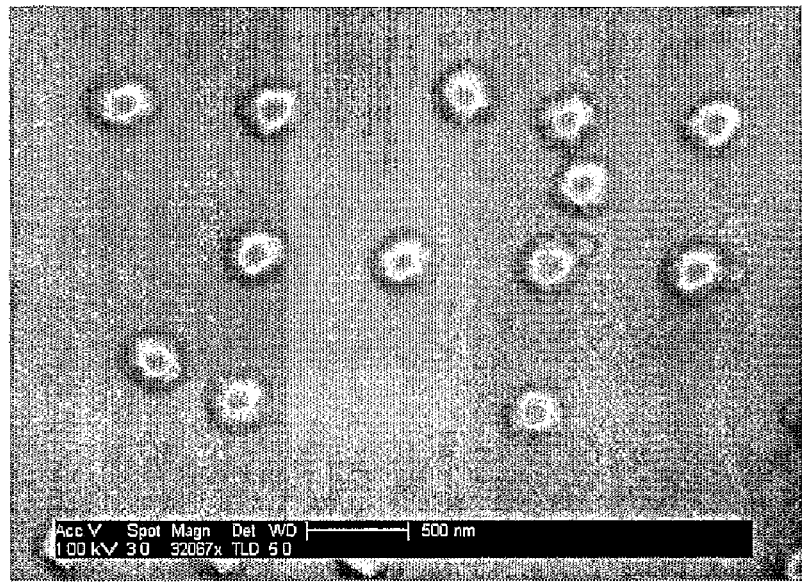
FIG. 29 is a scanning electron micrograph of fabrication of 200-nm PEG-diacrylate nanoparticles using "double stamping."

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 5 µL of the PEG-diacrylate/photoinitiator solution is pressed between the PFPE-DMA mold and the flat PFPE-DMA surface, and pressure is applied to squeeze out excess PEG-diacrylate monomer. The PFPE-DMA mold is then removed from the flat PFPE-DMA surface and pressed against a clean glass microscope slide and photocured using UV radiation ($\lambda$=365 nm) for 10 minutes while under a nitrogen purge. Particles are observed after cooling to room temperature and separation of the PFPE mold and the glass microscope slide, using scanning electron microscopy (SEM) (see FIG. 29).

Example 3.17

Encapsulation of Viruses in PEG-Diacrylate Nanoparticles

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 it % of a photoinitiator, 1-hydroxycyclohexyl phenyl ketone. Fluorescently-labeled or unlabeled Adenovirus or Adeno-Associated Virus suspensions are added to this PEG-diacrylate monomer solution and mixed thoroughly. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Virus-containing particles are observed after separation of the PFPE mold and the treated silicon wafer using transmission electron microscopy or, in the case of fluorescently-labeled viruses, confocal fluorescence microscopy.

Example 3.18

Encapsulation of Proteins in PEG-Diacrylate Nanoparticles

A patterned perfluoropolyether (PFPE) mold is generated by pouring PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Fluorescently-labeled or unlabeled protein solutions are added to this PEG-diacrylate monomer solution and mixed thoroughly. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 µL of the PEG diacrylate/virus solution is then placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. Protein-containing particles are observed after separation of the PFPE mold and the treated silicon wafer using traditional assay methods or, in the case of fluorescently-labeled proteins, confocal fluorescence microscopy.

Example 3.19

Fabrication of 200-nm Titania Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, non-wetting surfaces are generated by treating a silicon wafer cleaned with "piranha" solution (1:1 concentrated sulfuric acid:30% hydrogen peroxide (aq) solution) with trichloro (1H,1H,2H,2H-perfluorooctyl)silane via vapor deposition in a desiccator for 20 minutes. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Particles are observed after separation of the PFPE mold and the treated silicon wafer using scanning electron microscopy (SEM).

Example 3.20

Fabrication of 200-nm Silica Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, non-wetting surfaces are generated by treating a silicon wafer cleaned with "piranha" solution (1:1 concentrated sulfuric acid: 30% hydrogen peroxide (aq) solution) with trichloro (1H,1H,2H,2H-perfluorooctyl)silane via vapor deposition in a desiccator for 20 minutes. Following this, 50 μL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Particles are observed after separation of the PFPE mold and the treated silicon wafer using scanning electron microscopy (SEM).

Example 3.21

Fabrication of 200-nm Europium-Doped Titania Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3 \cdot 6H_2O$ are dissolved in 12 g of absolute ethanol. This solution is added to a solution of 2.7 mL of concentrated hydrochloric acid and 3.88 mL titanium (IV) ethoxide. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl) silane via vapor deposition in a desiccator for 20 minutes. Following this, 50 μL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Particles are observed after separation of the PFPE mold and the treated silicon wafer using scanning electron microscopy (SEM).

Example 3.22

Encapsulation of CdSe Nanoparticles Inside 200-nm PEG Particles

A patterned perfluoropolyether (PFPE) mold is generated by pouring a PFPE-dimethacrylate (PFPE-DMA) containing 1-hydroxycyclohexyl phenyl ketone over a silicon substrate patterned with 200-nm trapezoidal shapes (see FIG. 13). A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H, 2H-perfluorooctyl)silane via vapor deposition in a desiccator for 20 minutes. Separately, 0.5 g of sodium citrate and 2 mL of 0.04 M cadmium perchlorate are dissolved in 45 mL of water, and the pH is adjusted to of the solution to 9 with 0.1 M NaOH. The solution is bubbled with nitrogen for 15 minutes. 2 mL of 1 M N,N-dimethylselenourea is added to the solution and heated in a microwave oven for 60 seconds. 50 μL of this solution is added to 50 μL of a PEG diacrylate solution in a microtube. This microtube is vortexed for ten seconds. 50 μL of this PEG diacrylate/CdSe particle solution is placed on the treated silicon wafer and the patterned PFPE mold placed on top of it. The substrate is then placed in a molding apparatus and a small pressure is applied to push out excess PEG-diacrylate solution. The entire apparatus is then subjected to UV light ($\lambda$=365 nm) for ten minutes while under a nitrogen purge. PEG-diacrylate particles with encapsulated CdSe nanoparticles are observed after separation of the PFPE mold and the treated silicon wafer using TEM or fluorescence microscopy.

Example 3.23

Synthetic Replication of Adenovirus Particles Using Non-Wetting Imprint Lithography A template, or "master," for perfluoropolyether-dimethacrylate (PFPE-DMA) mold fabrication is generated by dispersing adenovirus particles on a silicon wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro (1H,1H,2H,2H-perfluorooctyl)silane via vapor deposition in a desiccator for 20 minutes. Following this, 50 μL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light ($\lambda$=365 nm) for ten minutes while under a nitrogen purge. Synthetic virus replicates are observed after separation of the PFPE mold and the treated silicon wafer using scanning electron microscopy (SEM) or transmission electron microscopy (TEM).

Example 3.24

Synthetic Replication of Earthworm Hemoglobin Protein Using Non-Wetting Imprint Lithography A template, or "master," for perfluoropolyether-dimethacrylate (PFPE-DMA) mold fabrication is generated by dispersing earthworm hemoglobin protein on a silicon wafer. This master can be used to template a patterned mold by pouring PFPE-DMA containing 1-hydroxycyclohexyl phenyl ketone over the patterned area of the master. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. Separately, TMPTA is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 μL of TMPTA is then placed on the treated silicon wafer and the patterned PFPE mold placed on top of it. The substrate is then placed in a molding apparatus and a small pressure is applied to push out excess TMPTA. The entire apparatus is then subjected to UV light (λ=365 nm) for ten minutes while under a nitrogen purge. Synthetic protein replicates are observed after separation of the PFPE mold and the treated silicon wafer using scanning electron microscopy (SEM) or transmission electron microscopy (TEM).

Example 3.25

Combinatorial Engineering of 100-nm Nanoparticle Therapeutics

A patterned perfluoropolyether (PFPE) mold is generated by pouring a PFPE-dimethacrylate (PFPE-DMA) containing 1-hydroxycyclohexyl phenyl ketone over a silicon substrate patterned with 100-nm cubic shapes. A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, a poly(ethylene glycol) (PEG) diacrylate (n=9) is blended with 1 wt % of a photoinitiator, 1-hydroxycyclohexyl phenyl ketone. Other therapeutic agents (i.e., small molecule drugs, proteins, polysaccharides, DNA, etc.), tissue targeting agents (cell penetrating peptides and ligands, hormones, antibodies, etc.), therapeutic release/transfection agents (other controlled-release monomer formulations, cationic lipids, etc.), and miscibility enhancing agents (cosolvents, charged monomers, etc.) are added to the polymer precursor solution in a combinatorial manner. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 μL of the combinatorially-generated particle precursor solution is then placed on the treated silicon wafer and the patterned PFPE mold placed on top of it. The substrate is then placed in a molding apparatus and a small pressure is applied to push out excess solution. The entire apparatus is then subjected to UV light (λ=365 nm) for ten minutes while under a nitrogen purge. The PFPE-DMA mold is then separated from the treated wafer, and particles are harvested and the therapeutic efficacy of each combinatorially generated nanoparticle is established. By repeating this methodology with different particle formulations, many combinations of therapeutic agents, tissue targeting agents, release agents, and other important compounds can be rapidly screened to determine the optimal combination for a desired therapeutic application.

Example 3.26

Fabrication of a Shape-Specific PEG Membrane

A patterned perfluoropolyether (PFPE) mold is generated by pouring a PFPE-dimethacrylate (PFPE-DMA) containing 1-hydroxycyclohexyl phenyl ketone over a silicon substrate patterned with 3-μm cylindrical holes that are 5 μm deep. A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, a polyethylene glycol) (PEG) diacrylate (n=9) is blended with 1 wt % of a photoinitiator, 1-hydroxycyclohexyl phenyl ketone. Flat, uniform, non-wetting surfaces are generated by treating a silicon wafer cleaned with "piranha" solution (1:1 concentrated sulfuric acid:30% hydrogen peroxide (aq) solution) with trichloro(1H,1H,2H,2H-perfluorooctyl)silane via vapor deposition in a desiccator for 20 minutes. Following this, 50 μL of PEG diacrylate is then placed on the treated silicon wafer and the patterned PFPE mold placed on top of it. The substrate is then placed in a molding apparatus and a small pressure is applied to push out excess PEG-diacrylate. The entire apparatus is then subjected to UV light (λ=365 nm) for ten minutes while under a nitrogen purge. An interconnected membrane is observed after separation of the PFPE mold and the treated silicon wafer using scanning electron microscopy (SEM). The membrane is released from the surface by soaking in water and allowing it to lift off the surface.

Example 4

Figure 30:
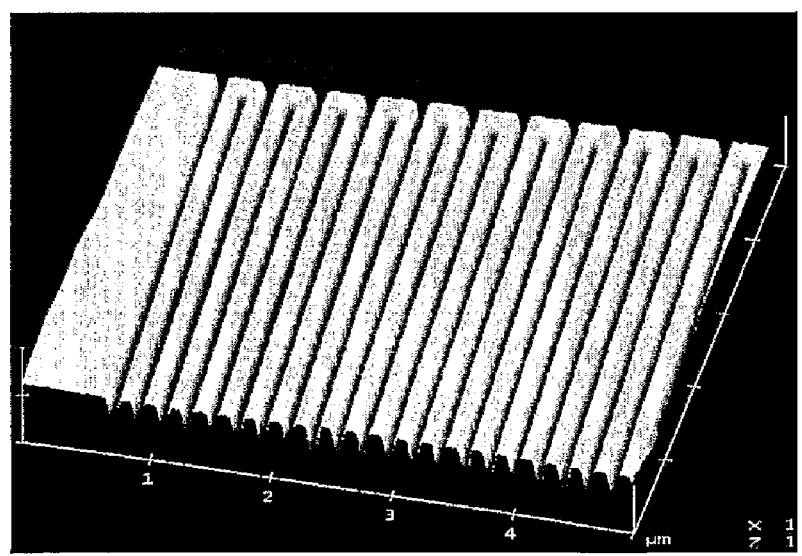
FIG. 30 is an atomic force micrograph image of 140-nm lines of TMPTA separated by distance of 70 nm that were fabricated using a PFPE mold.

Molding of features for semiconductor applications 4.1 Fabrication of 140-nm Lines Separated by 70 nm in TMPTA A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. Flat, uniform, surfaces are generated by treating a silicon wafer cleaned with "piranha" solution (1:1 concentrated sulfuric acid:30% hydrogen peroxide (aq) solution) and treating the wafer with an adhesion promoter, (trimethoxysilyl propyl methacryalte). Following this, 50 μL of TMPTA is then placed on the treated silicon wafer and the patterned PFPE mold placed on top of it. The substrate is then placed in a molding apparatus and a small pressure is applied to ensure a conformal contact. The entire apparatus is then subjected to UV light (λ=365 nm) for ten minutes while under a nitrogen purge. Features are observed after separation of the PFPE mold and the treated silicon wafer using atomic force microscopy (AFM) (see FIG. 30).

Example 4.1

Molding of a Polystyrene Solution

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly(dimethylsiloxane) mold is used to confine the liquid PFPE-DMA to the desired area. The apparatus is then subjected to UV light (λ=365 nm) for 10 minutes while under a nitrogen purge. The fully cured PFPE-DMA mold is then released from the silicon master. Separately, polystyrene is dissolved in 1 to 99 wt % of toluene. Flat, uniform, surfaces are generated by treating a silicon wafer cleaned with "piranha" solution (1:1 concentrated sulfuric acid:30% hydrogen peroxide (aq) solution) and treating the wafer with an adhesion promoter. Following this, 50 μL of polystyrene solution is then placed on the treated silicon wafer and the patterned PFPE mold is placed on top of it. The substrate is then placed in a molding apparatus and a small pressure is applied to ensure a conformal contact. The entire apparatus is then subjected to vacuum for a period of time to remove the solvent. Features are observed after separation of the PFPE mold and the treated silicon wafer using atomic force microscopy (AFM) and scanning electron microscopy (SEM).

Example 4.2

Molding of Isolated Features on Microelectronics-Compatible Surfaces Using "Double Stamping"

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone. A flat, non-wetting surface is generated by photocuring a film of PFPE-DMA onto a glass slide, according to the procedure outlined for generating a patterned PFPE-DMA mold. 50 µL of the TMPTA/photoinitiator solution is pressed between the PFPE-DMA mold and the flat PFPE-DMA surface, and pressure is applied to squeeze out excess TMPTA monomer. The PFPE-DMA mold is then removed from the flat PFPE-DMA surface and pressed against a clean, flat silicon/silicon oxide wafer and photocured using UV radiation ($\lambda$=365 nm) for 10 minutes while under a nitrogen purge. Isolated, poly (TMPTA) features are observed after separation of the PFPE mold and the silicon/silicon oxide wafer, using scanning electron microscopy (SEM).

Example 4.3

Fabrication of 200-nm Titania Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 is dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Oxide structures are observed after separation of the PFPE mold and the treated silicon wafer using scanning electron microscopy (SEM).

Example 4.4

Fabrication of 200-nm Silica Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 2 g of Pluronic P123 is dissolved in 30 g of water and 120 g of 2 M HCl is added while stirring at 35° C. To this solution, add 8.50 g of TEOS with stirring at 35° C. for 20 h. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol gel precursor has solidified. Oxide structures are observed after separation of the PFPE mold and the treated silicon wafer using scanning electron microscopy (SEM).

Example 4.5

Fabrication of 200-nm Europium-Doped Titania Structures for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, 1 g of Pluronic P123 and 0.51 g of $EuCl_3 \cdot 6H_2O$ are dissolved in 12 g of absolute ethanol. This solution was added to a solution of 2.7 mL of concentrated hydrochloric acid and 3.88 mL titanium (IV) ethoxide. Flat, uniform, surfaces are generated by treating a silicon/silicon oxide wafer with "piranha" solution (1:1 concentrated sulfuric acid:30% hydrogen peroxide (aq) solution) and drying. Following this, 50 µL of the sol-gel solution is then placed on the treated silicon wafer and the patterned PFPE mold placed on top of it. The substrate is then placed in a molding apparatus and a small pressure is applied to push out excess sol-gel precursor. The entire apparatus is then set aside until the sol-gel precursor has solidified. Oxide structures are observed after separation of the PFPE mold and the treated silicon wafer using scanning electron microscopy (SEM).

Example 4.6

Fabrication of Isolated "Scum Free" Features for Microelectronics

A patterned perfluoropolyether (PFPE) mold is generated by pouring a PFPE-dimethacrylate (PFPE-DMA) containing 1-hydroxycyclohexyl phenyl ketone over a silicon substrate patterned with 140-nm lines separated by 70 nm. A poly (dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the silicon master. Separately, TMPTA is blended with 1 wt % of a photoinitiator, 1-hydroxycyclohexyl phenyl ketone.

Flat, uniform, non-wetting surfaces capable of adhering to the resist material are generated by treating a silicon wafer cleaned with "piranha" solution (1:1 concentrated sulfuric acid:30% hydrogen peroxide (aq) solution) and treating the wafer with a mixture of an adhesion promoter, (trimethoxysilyl propyl methacryalte) and a non-wetting silane agent (1H, 1H,2H,2H-perfluorooctyl trimethoxysilane). The mixture can range from 100% of the adhesion promoter to 100% of the non-wetting silane. Following this, 50 μL of TMPTA is then placed on the treated silicon wafer and the patterned PFPE mold placed on top of it. The substrate is then placed in a molding apparatus and a small pressure is applied to ensure a conformal contact and to push out excess TMPTA. The entire apparatus is then subjected to UV light ($\lambda$=365 nm) for ten minutes while under a nitrogen purge. Features are observed after separation of the PFPE mold and the treated silicon wafer using atomic force microscopy (AFM) and scanning electron microscopy (SEM).

Example 5

Figure 31A:
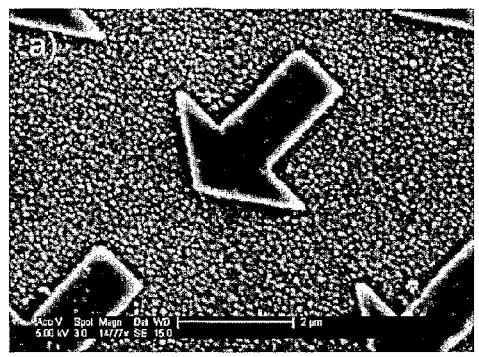
FIGS. 31A and 31B are a scanning electron micrograph of mold fabrication from electron-beam lithographically generated masters.
Figure 31B:
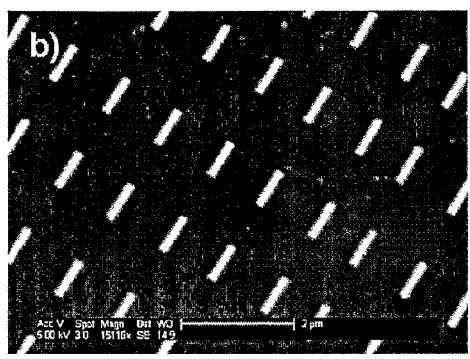

Molding of Natural and Engineered Templates 5.1. Fabrication of a
Perfluoropolyether-Dimethacrylate (PFPE-DMA)
Mold from a Template Generated Using
Electron-Beam Lithography A template, or "master," for perfluoropolyether-dimethacrylate (PFPE-DMA) mold fabrication is generated using electron beam lithography by spin coating a bilayer resist of 200,000 MW PMMA and 900,000 MW PMMA onto a silicon wafer with 500-nm thermal oxide, and exposing this resist layer to an electron beam that is translating in a pre-programmed pattern. The resist is developed in 3:1 isopropanol:methyl isobutyl ketone solution to remove exposed regions of the resist. A corresponding metal pattern is formed on the silicon oxide surface by evaporating 5 nm Cr and 15 nm Au onto the resist covered surface and lifting off the residual PMMA/Cr/Au film in refluxing acetone. This pattern is transferred to the underlying silicon oxide surface by reactive ion etching with $CF_4/O_2$ plasma and removal of the Cr/Au film in aqua regia. (FIG. 31). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. This mold can be used for the fabrication of particles using non-wetting imprint lithography as specified in Particle Fabrication Examples 3.3 and 3.4.

Figure 32A:
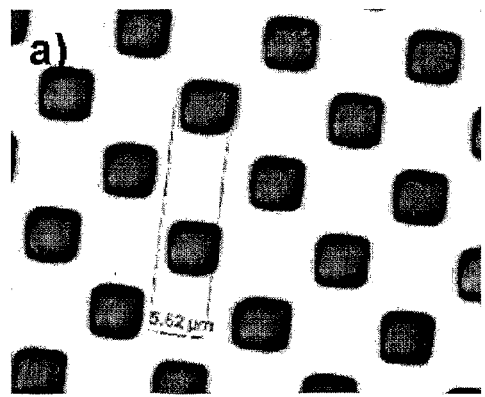
FIGS. 32A and 32B are an optical micrographic image of mold fabrication from photoresist masters.
Figure 32B:
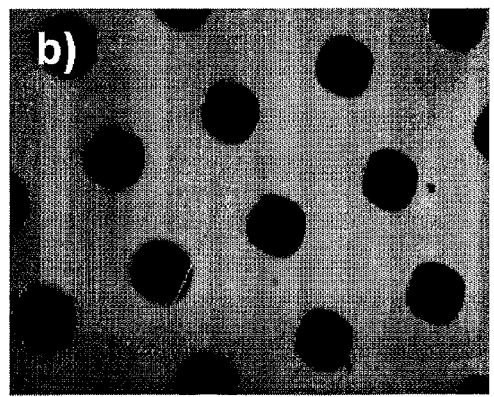

5.2 Fabrication of a
Perfluoropolyether-Dimethacrylate (PFPE-DMA)
Mold from a Template Generated Using
Photolithography A template, or "master," for perfluoropolyether-dimethacrylate (PFPE-DMA) mold fabrication is generated using photolithography by spin coating a film of SU-8 photoresist onto a silicon wafer. This resist is baked on a hotplate at 95° C. and exposed through a pre-patterned photomask. The wafer is baked again at 95° C. and developed using a commercial developer solution to remove unexposed SU-8 resist. The resulting patterned surface is fully cured at 175° C. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master, and can be imaged by optical microscopy to reveal the patterned PFPE-DMA mold (see FIG. 32).

Figures 33A, 33B:
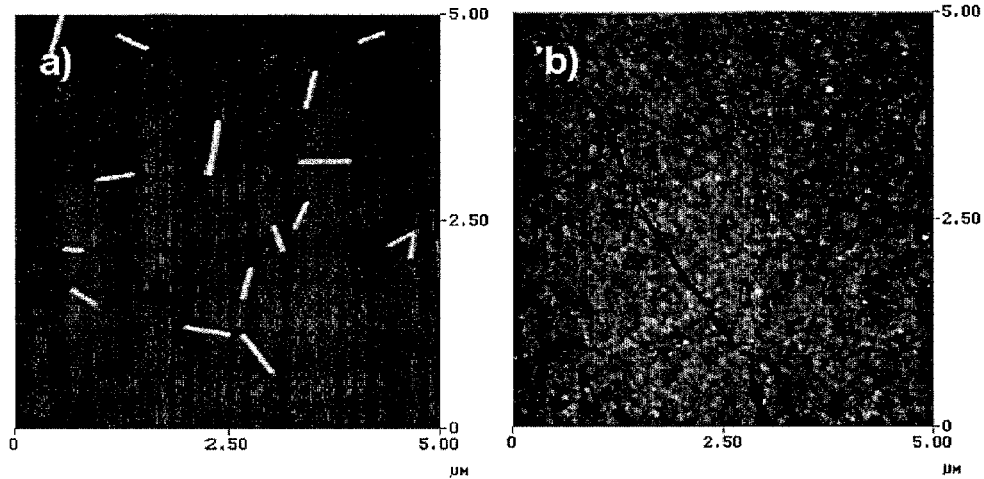
FIGS. 33A and 33B are an atomic force micrograph of mold fabrication from Tobacco Mosaic Virus templates.

5.3 Fabrication of a
Perfluoropolyether-Dimethacrylate (PFPE-DMA)
Mold from a Template Generated from Dispersed
Tobacco Mosaic Virus Particles A template, or "master," for perfluoropolyether-dimethacrylate (PFPE-DMA) mold fabrication is generated by dispersing tobacco mosaic virus (TMV) particles on a silicon wafer (FIG. 33a). This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 33b).

Figures 34A, 34B:
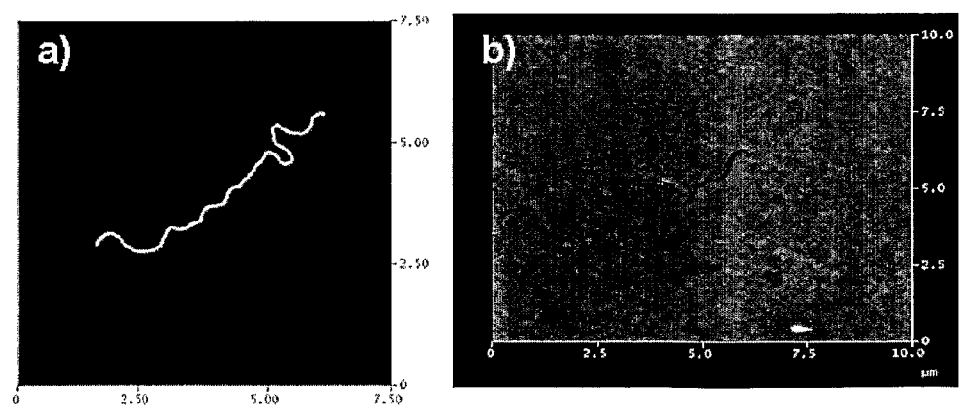
FIGS. 34A and 34B are an atomic force micrograph of mold fabrication from block copolymer micelle masters.

5.4. Fabrication of a
Perfluoropolyether-Dimethacrylate (PFPE-DMA)
Mold from a Template Generated from
Block-Copolymer Micelles A template, or "master," for perfluoropolyether-dimethacrylate (PFPE-DMA) mold fabrication is generated by dispersing polystyrene-polyisoprene block copolymer micelles on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (see FIG. 34).

5.5 Fabrication of a
Perfluoropolyether-Dimethacrylate (PFPE-DMA)
Mold from a Template Generated from Brush
Polymers A template, or "master," for perfluoropolyether-dimethacrylate (PFPE-DMA) mold fabrication is generated by dispersing poly(butyl acrylate) brush polymers on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy (FIG. 35).

Example 5.6

Fabrication of a Perfluoropolyether-Dimethacrylate (PFPE-DMA) Mold from a Template Generated from Earthworm Hemoglobin Protein A template, or "master," for perfluoropolyether-dimethacrylate (PFPE-DMA) mold fabrication is generated by dispersing earthworm hemoglobin proteins on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

Example 5.7

Fabrication of a Perfluoropolyether-Dimethacrylate (PFPE-DMA) Mold from a Template Generated from Patterned DNA Nanostructures A template, or "master," for perfluoropolyether-dimethacrylate (PFPE-DMA) mold fabrication is generated by dispersing DNA nanostructures on a freshly-cleaved mica surface. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

Example 5.8

Fabrication of a Perfluoropolyether-Dimethacrylate (PFPE-DMA) Mold from a Template Generated from Carbon Nanotubes A template, or "master," for perfluoropolyether-dimethacrylate (PFPE-DMA) mold fabrication is generated by dispersing or growing carbon nanotubes on a silicon oxide wafer. This master can be used to template a patterned mold by pouring PFPE-DMA containing 1-hydroxycyclohexyl phenyl ketone over the patterned area of the master. A poly(dimethylsiloxane) mold is used to confine the liquid PFPE-DMA to the desired area. The apparatus is then subjected to UV light ($\lambda$=365 nm) for 10 minutes while under a nitrogen purge. The fully cured PFPE-DMA mold is then released from the master. The morphology of the mold can then be confirmed using Atomic Force Microscopy.

Example 6

Method of Making Monodisperse Nanostructures Having a Plurality of Shapes and Sizes In some embodiments, the presently disclosed subject matter describes a novel "top down" soft lithographic technique; non-wetting imprint lithography (NoWIL) which allows completely isolated nanostructures to be generated by taking advantage of the inherent low surface energy and swelling resistance of cured PFPE-based materials.

The presently described subject matter provides a novel "top down" soft lithographic technique; non-wetting imprint lithography (NoWIL) which allows completely isolated nanostructures to be generated by taking advantage of the inherent low surface energy and swelling resistance of cured PFPE-based materials. Without being bound to any one particular theory, a key aspect of NoWIL is that both the elastomeric mold and the surface underneath the drop of monomer or resin are non-wetting to this droplet. If the droplet wets this surface, a thin scum layer will inevitably be present even if high pressures are exerted upon the mold. When both the elastomeric mold and the surface are non-wetting (i.e. a PFPE mold and fluorinated surface) the liquid is confined only to the features of the mold and the scum layer is eliminated as a seal forms between the elastomeric mold and the surface under a slight pressure. Thus, the presently disclosed subject matter provides for the first time a simple, general, soft lithographic method to produce nanoparticles of nearly any material, size, and shape that are limited only by the original master used to generate the mold.

Using NoWIL, nanoparticles composed of 3 different polymers were generated from a variety of engineered silicon masters. Representative patterns include, but are not limited to, 3-µm arrows (see FIG. 11), conical shapes that are 500 nm at the base and converge to <50 nm at the tip (see FIG. 12), and 200-nm trapezoidal structures (see FIG. 13). Definitive proof that all particles were indeed "scum-free" was demonstrated by the ability to mechanically harvest these particles by simply pushing a doctor's blade across the surface. See FIGS. 20 and 22.

Polyethylene glycol (PEG) is a material of interest for drug delivery applications because it is readily available, non-toxic, and biocompatible. The use of PEG nanoparticles generated by inverse microemulsions to, be used as gene delivery vectors has previously been reported. K. McAllister et al., *Journal of the American Chemical Society* 124, 15198-15207 (Dec. 25, 2002). In the presently disclosed subject matter, NoWIL was performed using a commercially available PEG-diacrylate and blending it with 1 wt % of a photoinitiator, 1-hydroxycyclohexyl phenyl ketone. PFPE molds were generated from a variety of patterned silicon substrates using a dimethacrylate functionalized PFPE oligomer (PFPE DMA) as described previously. See J. P. Rolland, E. C. Hagberg, G. M. Denison, K. R. Carter, J. M. DeSimone, *Angewandte Chemie-International Edition* 43, 5796-5799 (2004). Flat, uniform, non-wetting surfaces were generated by using a silicon wafer treated with a fluoroalkyl trichlorosilane or by drawing a doctor's blade across a small drop of PFPE-DMA on a glass substrate and photocuring. A small drop of PEG diacrylate was then placed on the non-wetting surface and the patterned PFPE mold placed on top of it. The substrate was then placed in a molding apparatus and a small pressure was applied to push out the excess PEG-diacrylate. The entire apparatus was then subjected to UV light ($\lambda$=365 nm) for ten minutes while under a nitrogen purge. Particles were observed after separation of the PFPE mold and flat, non-wetting substrate using optical microscopy, scanning electron microscopy (SEM), and atomic force microscopy (AFM).

Poly(lactic acid) (PLA) and derivatives thereof, such as poly(lactide-co-glycolide) (PLGA), have had a considerable impact on the drug delivery and medical device communities because it is biodegradable. See K. E. Uhrich, S. M. Cannizzaro, R. S. Langer, K. M. Shakesheff, Chemical Reviews 99, 3181-3198 (November, 1999); A. C. Albertsson, I. K. Varma, *Biomacromolecules* 4, 1466-1486 (November-December, 2003). As with PEG-based systems, progress has been made toward the fabrication of PLGA particles through various dispersion techniques that result in size distributions and are strictly limited to spherical shapes. See C. Cui, S. P. Schwendeman, *Langmuir* 34, 8426 (2001).

The presently disclosed subject matter demonstrates the use of NoWIL to generate discrete PLA particles with total control over shape and size distribution. For example, in one embodiment, one gram of (3S)-cis-3,6-dimethyl-1,4-dioxane-2,5-dione was heated above its melting temperature to 110° C. and ~20 µL of stannous octoate catalyst/initiator was added to the liquid monomer. A drop of the PLA monomer solution was then placed into a preheated molding apparatus which contained a non-wetting flat substrate and mold. A small pressure was applied as previously described to push out excess PLA monomer. The apparatus was allowed to heat at 110° C. for 15 h until the polymerization was complete. The PFPE-DMA mold and the flat, non-wetting substrate were then separated to reveal the PLA particles.

To further demonstrate the versatility of NoWIL, particles composed of a conducting polymer polypyrrole (PPy) were generated. PPy particles have been formed using dispersion methods, see M. R. Simmons, P. A. Chaloner, S. P. Armes, *Langmuir* 11, 4222 (1995), as well as "lost-wax" techniques, see P. Jiang, J. F. Bertone, V. L. Colvin, *Science* 291, 453 (2001).

The presently disclosed subject matter demonstrate for the first time, complete control over shape and size distribution of PPy particles. Pyrrole is known to polymerize instantaneously when in contact with oxidants such as perchloric acid. Dravid et al. has shown that this polymerization can be retarded by the addition of tetrahydrofuran (THF) to the pyrrole. See M. Su, M. Aslam, L. Fu, N. Q. Wu, V. P. Dravid, *Applied Physics Letters* 84, 4200-4202 (May 24, 2004).

The presently disclosed subject matter takes advantage of this property in the formation of PPy particles by NoWIL. For example, 50 µL of a 1:1 v/v solution of THF:pyrrole was added to 50 µL of 70% perchloric acid. A drop of this clear, brown solution (prior to complete polymerization) into the molding apparatus and applied pressure to remove excess solution. The apparatus was then placed into the vacuum oven overnight to remove the THF and water. PPy particles were fabricated with good fidelity using the same masters as previously described.

Importantly, the materials properties and polymerization mechanisms of PLA, PEG, and PPy are completely different. For example, while PLA is a high-modulus, semicrystalline polymer formed using a metal-catalyzed ring opening polymerization at high temperature, PEG is a malleable, waxy solid that is photocured free radically, and PPy is a conducting polymer polymerized using harsh oxidants. The fact that NoWIL can be used to fabricate particles from these diverse classes of polymeric materials that require very different reaction conditions underscores its generality and importance.

In addition to its ability to precisely control the size and shape of particles, NoWIL offers tremendous opportunities for the facile encapsulation of agents into nanoparticles. As described in Example 3-14, NoWIL can be used to encapsulate a 24-mer DNA strand fluorescently tagged with CY-3 inside the previously described 200 nm trapezoidal PEG particles. This was accomplished by simply adding the DNA to the monomer/water solution and molding them as described. We were able to confirm the encapsulation by observing the particles using confocal fluorescence microscopy (see FIG. 28). The presently described approach offers a distinct advantage over other encapsulation methods in that no surfactants, condensation agents, and the like are required. Furthermore, the fabrication of monodisperse, 200 nm particles containing DNA represents a breakthrough step towards artificial viruses. Accordingly, a host of biologically important agents, such as gene fragments, pharmaceuticals, oligonucleotides, and viruses, can be encapsulated by this method.

The method also is amenable to non-biologically oriented agents, such as metal nanoparticles, crystals, or catalysts. Further, the simplicity of this system allows for straightforward adjustment of particle properties, such as crosslink density, charge, and composition by the addition of other comonomers, and combinatorial generation of particle formulations that can be tailored for specific applications.

Accordingly, NoWIL is a highly versatile method for the production of isolated, discrete nanostructures of nearly any size and shape. The shapes presented herein were engineered non-arbitrary shapes. NoWIL can easily be used to mold and replicate non-engineered shapes found in nature, such as viruses, crystals, proteins, and the like. Furthermore, the technique can generate particles from a wide variety of organic and inorganic materials containing nearly any cargo. The method is simplistically elegant in that it does not involve complex surfactants or reaction conditions to generate nanoparticles. Finally, the process can be amplified to an industrial scale by using existing soft lithography roller technology, see Y. N. Xia, D. Qin, G. M. Whitesides, *Advanced Materials* 8, 1015-1017 (December, 1996), or silk screen printing methods.

Example 7

Synthesis of Functional Perfluoropolyethers

Example 7.1

Synthesis of Krytox® (DuPont, Wilmington, Del., United States of America) Diol to be Used as a Functional PFPE

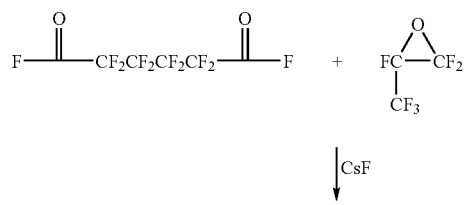

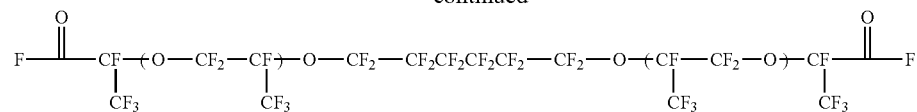

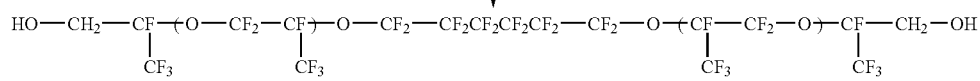

Example 7.2

Synthesis of Krytox® (DuPont, Wilmington, Del., United States of America) Diol to be Used as a Functional PFPE

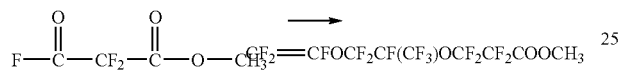

Example 7.3

Synthesis of Krytox® (DuPont, Wilmington, Del., United States of America) Diol to be Used as a Functional PFPE

-continued

FOCCF(CF$_3$)[OCF$_2$CF(CF$_3$)]$_{13}$OCF$_2$CF$_2$COOCH$_3$

Example 7.4

Example of Krytox® (DuPont, Wilmington, Del., United States of America) Diol to be Used as a Functional PFPE

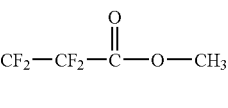

mw = 2436

Example 7.5

Synthesis of a Multi-Arm PFPE Precursor

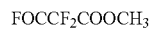

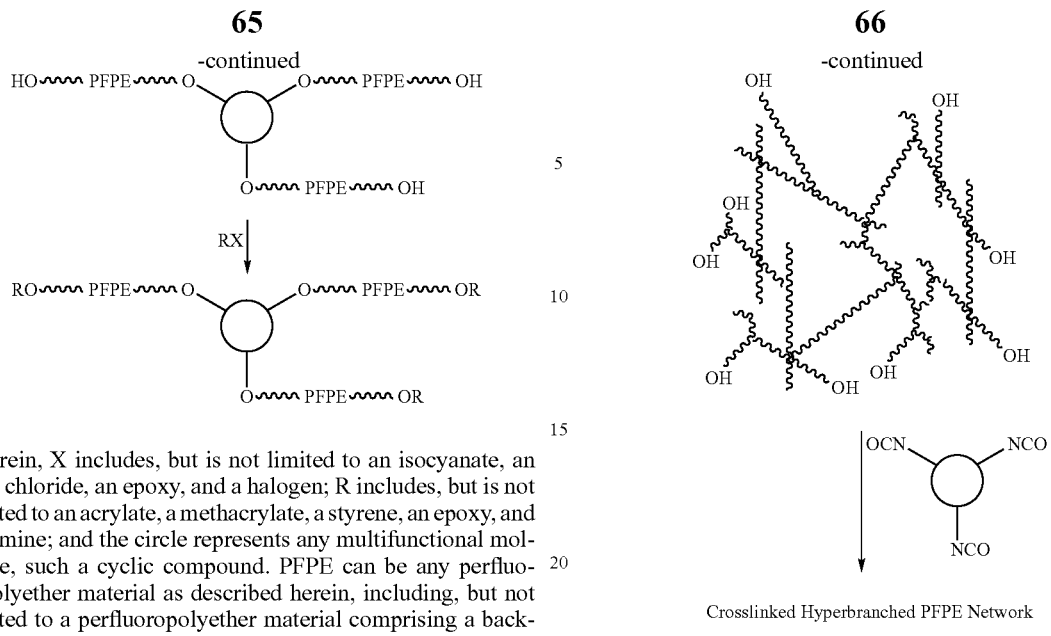

wherein, X includes, but is not limited to an isocyanate, an acid chloride, an epoxy, and a halogen; R includes, but is not limited to an acrylate, a methacrylate, a styrene, an epoxy, and an amine; and the circle represents any multifunctional molecule, such a cyclic compound. PFPE can be any perfluoropolyether material as described herein, including, but not limited to a perfluoropolyether material comprising a backbone structure as follows:

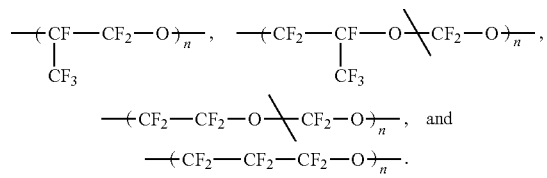

Example 7.6

Synthesis of a Hyperbranched PFPE Precursor

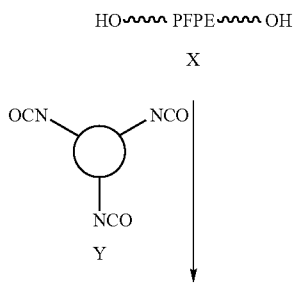

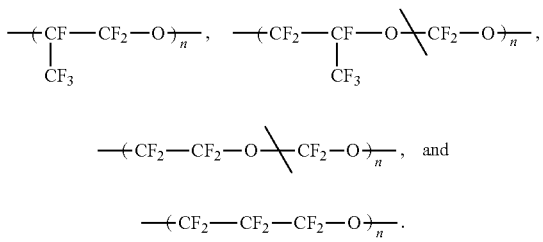

Crosslinked Hyperbranched PFPE Network

∿∿∿∿ = PFPE Chain

Hyperbranched PFPE precursor wherein, PFPE can be any perfluoropolyether material as described herein, including, but not limited to a perfluoropolyether material comprising a backbone structure as follows:

$$-\!\!\left(\!\text{CF}\!-\!\text{CF}_2\!-\!\text{O}\!\right)_{\!n}\!\!-,\quad -\!\!\left(\!\text{CF}_2\!-\!\text{CF}\!-\!\text{O}\!\right)\!\!\left(\!\text{CF}_2\!-\!\text{O}\!\right)_{\!n}\!\!-,$$
$$\phantom{-\!\!\left(\!\text{CF}\!-\right)}\text{CF}_3 \phantom{xxxxxxxxxx} \text{CF}_3$$

$$-\!\!\left(\!\text{CF}_2\!-\!\text{CF}_2\!-\!\text{O}\!\right)\!\!\left(\!\text{CF}_2\!-\!\text{O}\!\right)_{\!n}\!\!-,\quad \text{and}$$

$$-\!\!\left(\!\text{CF}_2\!-\!\text{CF}_2\!-\!\text{CF}_2\!-\!\text{O}\!\right)_{\!n}\!\!-.$$

It will be understood that various details of the presently disclosed subject matter can be changed without departing from the scope of the presently disclosed subject matter. Furthermore, the foregoing description is for the purpose of illustration only, and not for the purpose of limitation.

---

What is claimed is:

1. A method for forming a plurality of substantially uniform nanoparticles, the method comprising:
   (a) providing a patterned template and a first substrate, wherein at least one of said patterned template or said substrate has a non-wetting surface, and wherein the patterned template comprises a patterned template surface having a plurality of recessed areas formed therein;
   (b) disposing a volume of liquid material in or on at least one of:
      (i) the patterned template surface;
      (ii) the plurality of recessed areas; and
      (iii) said first substrate; and
   (c) forming said plurality of substantially uniform nanoparticles by:
      contacting the patterned template surface with the first substrate and treating the liquid material to form nanoparticles in the recessed areas of the patterned template wherein the nanoparticles are essentially free of a scum layer;
   (d) removing the first substrate from the patterned template; and
   (e) releasing the nanoparticles from the patterned template by applying the patterned template to a second substrate, wherein the second substrate has an affinity for the nanoparticles that is greater than the affinity of the nanoparticles for the patterned template, and wherein each of said nanoparticles substantially mimics the recessed areas.

2. The method of claim 1, wherein the patterned template comprises a solvent resistant, low surface energy polymeric material.

3. The method of claim 1, wherein the patterned template comprises a solvent resistant elastomeric material.

4. The method of claim 1, wherein at least one of the patterned template and first substrate comprises a material selected from the group consisting of a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

5. The method of claim 1, wherein at least one of the patterned template and the first substrate has a surface energy lower than 18 mN/m.

6. The method of claim 1, wherein at least one of the patterned template and the first substrate has a surface energy lower than 15 mN/m.

7. The method of claim 1, wherein the first substrate is selected from the group consisting of a polymer material, an inorganic material, a silicon material, a quartz material, a glass material, and surface treated variants thereof.

8. The method of claim 1, wherein the first substrate comprises a patterned area.

9. The method of claim 1, wherein the plurality of recessed areas comprise a plurality of cavities.

10. The method of claim 9, wherein the plurality of cavities comprise a plurality of structural features.

11. The method of claim 10, wherein the plurality of structural features have a dimension ranging from about 1,000 nm to about 100 nm in size.

12. The method of claim 10, wherein the plurality of structural features have a dimension ranging from about 100 nm to about 1 nm in size.

13. The method of claim 1, wherein the patterned template comprises a patterned template formed by a replica molding process.

14. The method of claim 13, wherein the replica molding process comprises:
   (a) providing a master template;
   (b) contacting a liquid material with the master template; and
   (c) curing the liquid material to form a patterned template.

15. The method of claim 14, wherein the master template is selected from the group consisting of:
   (a) a template formed from a lithography process;
   (b) a naturally occurring template; and
   (c) combinations thereof.

16. The method of claim 1, comprising modifying the patterned template surface by a surface modification step.

17. The method of claim 16, wherein the surface modification step is selected from the group consisting of a plasma treatment, a chemical treatment, and an adsorption process.

18. The method of claim 1, comprising positioning the patterned template and the first substrate in a spaced relationship to each other such that the patterned template surface and the first substrate face each other in a predetermined alignment.

19. The method of claim 1, wherein the liquid material is selected from the group consisting of a polymer, a solution, a monomer, a plurality of monomers, a polymerization initiator, a polymerization catalyst, an inorganic precursor, a metal precursor, a pharmaceutical agent, a tag, a magnetic material, a paramagnetic material, a superparamagnetic material, a ligand, a cell penetrating peptide, a porogen, a surfactant, a plurality of immiscible liquids, a solvent, and a charged species.

20. The method of claim 19, wherein the pharmaceutical agent is selected from the group consisting of a drug, a peptide, RNAi, and DNA.

21. The method of claim 19, wherein the tag is selected from the group consisting of a fluorescence tag, a radiolabeled tag, and a contrast agent.

22. The method of claim 19, wherein the ligand comprises a cell targeting peptide.

23. The method of claim 1, wherein the liquid material comprises a non-wetting agent.

24. The method of claim 1, wherein the disposing of the volume of liquid material is regulated by a spreading process.

25. The method of claim 24, wherein the spreading process comprises:
   (a) disposing a first volume of liquid material on the patterned template to form a layer of liquid material on the patterned template; and
   (b) drawing an implement across the layer of liquid material to:
      (i) remove a second volume of liquid material from the layer of liquid material on the patterned template; and
      (ii) leave a third volume of liquid material on the patterned template.

26. The method of claim 1, wherein the contacting of the patterned template surface with the first substrate displaces essentially all of the disposed liquid material from between the patterned template surface and the first substrate.

27. The method of claim 1, wherein the treating of the liquid material comprises a process selected from the group consisting of a thermal process, a photochemical process, and a chemical process.

28. The method of claim 1, further comprising, after (b) and before (c):

(b1) reducing the volume of the liquid material disposed in the plurality of recessed areas by one of:
  (i) applying a contact pressure to the patterned template surface; and
  (ii) allowing a second volume of the liquid to evaporate or permeate through the template;
(b2) removing the contact pressure applied to the patterned template surface; and
(b3) introducing gas within the recessed areas of the patterned template surface.

29. The method of claim 1, comprising harvesting or collecting the nanoparticles.

30. The method of claim 29, wherein the harvesting or collecting of the nanoparticles comprises a process selected from the group consisting of scraping with a medical scalpel, a brushing process, a dissolution process, an ultrasound process, a megasonics process, an electrostatic process, and a magnetic process.

31. The method of claim 1, wherein the method comprises a batch process.

32. The method of claim 31, wherein the batch process is selected from one of a semi-batch process and a continuous batch process.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Gly Arg Gly Asp Ser Pro
1               5